US011617724B2

(12) United States Patent
Sonti et al.

(10) Patent No.: US 11,617,724 B2
(45) Date of Patent: *Apr. 4, 2023

(54) TOPICAL PHARMACEUTICAL COMPOSITIONS

(71) Applicant: Dermavant Sciences GmbH, Basel (CH)

(72) Inventors: Sujatha D. Sonti, Research Triangle Park, NC (US); Joey Roger Thomas, Research Triangle Park, NC (US); Jon Lenn, Research Triangle Park, NC (US); Leandro Santos, Research Triangle Park, NC (US); Justin Whiteman, Raleigh, NC (US); Michael Quinn Doherty, Research Triangle Park, NC (US); Mary Bedard, Research Triangle Park, NC (US); Piyush Jain, Chester Springs, PA (US)

(73) Assignee: DERMAVANT SCIENCES GMBH, Basel (CH)

( * ) Notice: Subject to any disclaimer, the term of this patent is extended or adjusted under 35 U.S.C. 154(b) by 206 days.

This patent is subject to a terminal disclaimer.

(21) Appl. No.: 15/807,682

(22) Filed: Nov. 9, 2017

(65) Prior Publication Data

US 2018/0064656 A1 Mar. 8, 2018

Related U.S. Application Data

(63) Continuation-in-part of application No. 15/158,858, filed on May 19, 2016, now Pat. No. 10,195,160.

(60) Provisional application No. 62/420,856, filed on Nov. 11, 2016, provisional application No. 62/324,450, filed on Apr. 19, 2016, provisional application No. 62/165,097, filed on May 21, 2015.

(51) Int. Cl.
| | | |
|---|---|---|
| *A61K 9/107* | (2006.01) | |
| *A61K 9/06* | (2006.01) | |
| *A61K 9/00* | (2006.01) | |
| *A61K 47/26* | (2006.01) | |
| *A61K 47/06* | (2006.01) | |
| *A61K 47/14* | (2017.01) | |
| *A61K 9/10* | (2006.01) | |
| *A61K 31/05* | (2006.01) | |
| *A61K 47/10* | (2017.01) | |
| *A61K 9/113* | (2006.01) | |

(52) U.S. Cl.
CPC ............ *A61K 31/05* (2013.01); *A61K 9/0014* (2013.01); *A61K 9/06* (2013.01); *A61K 9/107* (2013.01); *A61K 9/113* (2013.01); *A61K 47/06* (2013.01); *A61K 47/10* (2013.01); *A61K 47/14* (2013.01); *A61K 47/26* (2013.01)

(58) Field of Classification Search
None
See application file for complete search history.

(56) References Cited

U.S. PATENT DOCUMENTS

| | | | | |
|---|---|---|---|---|
| 4,048,310 A | * | 9/1977 | Chen | A61K 9/0014 514/174 |
| 5,008,100 A | * | 4/1991 | Zecchino | A61Q 17/04 424/47 |
| 5,961,970 A | | 10/1999 | Lowell et al. | |
| 6,113,921 A | * | 9/2000 | Friedman | A61M 35/00 424/400 |
| 6,210,693 B1 | | 4/2001 | Inoue et al. | |
| 6,299,884 B1 | | 10/2001 | Van Nest et al. | |
| 6,325,995 B1 | * | 12/2001 | El-Nokaly | A61K 8/0295 424/64 |
| 6,689,922 B1 | | 2/2004 | Bernardon | |
| 7,321,050 B2 | | 1/2008 | Chen et al. | |
| 7,868,047 B2 | | 1/2011 | Chen et al. | |
| 8,487,009 B2 | | 7/2013 | Chen et al. | |
| 9,308,239 B2 | | 4/2016 | Thiboutot et al. | |
| 10,195,160 B2 | | 2/2019 | Sonti et al. | |
| 2002/0032171 A1 | | 3/2002 | Chen et al. | |
| 2002/0035182 A1 | | 3/2002 | L'Alloret et al. | |
| 2002/0054890 A1 | | 5/2002 | Gers-Barlag et al. | |
| 2003/0059470 A1 | | 3/2003 | Muller | |
| 2003/0073712 A1 | | 4/2003 | Wang et al. | |
| 2003/0171429 A1 | | 9/2003 | Chen et al. | |

(Continued)

FOREIGN PATENT DOCUMENTS

| | | | |
|---|---|---|---|
| CA | 2266763 A1 | | 10/1999 |
| CN | 101822638 A | * | 9/2010 |

(Continued)

OTHER PUBLICATIONS

English translation of CN-101822638-A obtained from WIPO and Google translate. (Year: 2019).*
Bissonnette et al., Efficacy and Safety of Topical WBI-1001 in Patients with Mild to Moderate Psoriasis: Results from a Randomized Double-Blind Placebo-Controlled, Phase II Trial, JEADV (2012); 26:1516-1521.
Bissonnette et al., Efficacy and Safety of Topical WBI-1001 in Patients with Mild to Severe Atopic Dermatitis: Results from a 12-week, Multicentre, Randomized, Placebo-Controlled Double-Blind Trial, British Association of Dermatologists (2012); 166:853-860.
Bissonnette et al., Efficacy and Safety of Topical WBI-1001 in the Treatment of Atopic Dermatitis: Results From a Phase 2A, Randomized, Placebo-Controlled Clinical Trial, (Reprinted) Arch Dermatol; 146(4); 446-449 (Apr. 2010).

(Continued)

*Primary Examiner* — Robert T. Crow
*Assistant Examiner* — John P Nguyen
(74) *Attorney, Agent, or Firm* — DLA Piper LLP (US)

(57) ABSTRACT

The present invention relates to topical pharmaceutical emulsion compositions comprising a therapeutically effective amount of 3,5-Dihydroxy-4-isopropyl-trans-stilbene or a pharmaceutically acceptable salt thereof, an oil phase, a water phase, a surfactant, and an antioxidant, and wherein the emulsion composition is homogeneous and/or the active is solubilized in the oil phase. The invention also relates to methods of treating a dermatological condition or disorder in a patient by administering the present compositions to the skin of the patient.

46 Claims, 11 Drawing Sheets

(56) References Cited

U.S. PATENT DOCUMENTS

| | | | |
|---|---|---|---|
| 2004/0018244 A1 | 1/2004 | Piterski | |
| 2004/0202634 A1 | 10/2004 | L'Alloret | |
| 2005/0059733 A1 | 3/2005 | Chen et al. | |
| 2006/0018861 A1 | 1/2006 | Chen et al. | |
| 2006/0246098 A1 | 11/2006 | Rao et al. | |
| 2007/0128260 A1 | 6/2007 | Lau et al. | |
| 2007/0264344 A1 | 11/2007 | Segura-Orsoni et al. | |
| 2008/0206155 A1 | 8/2008 | Tamarkin et al. | |
| 2009/0010863 A1 | 1/2009 | Barton et al. | |
| 2009/0269380 A1 | 10/2009 | Baker, Jr. et al. | |
| 2009/0324727 A1 | 12/2009 | Foguet Roca | |
| 2010/0221194 A1 | 9/2010 | Loupenok | |
| 2011/0165260 A1 | 7/2011 | Farber | |
| 2011/0212146 A1 | 9/2011 | Helland et al. | |
| 2012/0149748 A1* | 6/2012 | Shanler | A61P 17/00 514/401 |
| 2013/0028850 A1 | 1/2013 | Tamarkin et al. | |
| 2013/0224268 A1 | 8/2013 | Alam et al. | |
| 2013/0273172 A1 | 10/2013 | Roy et al. | |
| 2013/0303495 A1 | 11/2013 | Dhingra et al. | |
| 2014/0213564 A1 | 7/2014 | Hardas et al. | |
| 2016/0287531 A1 | 10/2016 | Vander Jagt et al. | |
| 2017/0360719 A1 | 12/2017 | Cote-Sierra et al. | |
| 2019/0144367 A1 | 5/2019 | Andrews et al. | |
| 2019/0151255 A1 | 5/2019 | Sonti et al. | |

FOREIGN PATENT DOCUMENTS

| | | |
|---|---|---|
| CN | 101822638 A | 9/2010 |
| CN | 102657602 B | 9/2012 |
| CN | 102657610 A | 9/2012 |
| CN | 103315958 B | 10/2014 |
| GB | 1465661 A | 2/1977 |
| JP | 58159410 A | 9/1983 |
| JP | 10072330 A | 3/1998 |
| WO | 1999044585 A1 | 9/1999 |
| WO | 99059561 A3 | 4/2000 |
| WO | WO 01/42231 A2 | 6/2001 |
| WO | 2005087195 A2 | 9/2005 |

OTHER PUBLICATIONS

Gao et al., Preparation of Chitosan Microspheres Loading of 3,5-dihydroxy-4-i-propylstilbene and In Vitro Release, J Polym Res. Jan. 6, 2011, 18:1501-1508.

Gessner, Neurodermitis-Sonnenblumenol hilft Steroid einsparen: Medical Tribune—Medizin und Gesundheit. Retrieved online at: <http://www.medical-tribune.de/medizin/fokus-medizin/artikeldetail/neurodermitis-sonnenblymenoel-hilft-steroid-einsparen.html>. (2011).

Kelhala et al., IL-17/Th17 pathway is activated in acne lesions. PLoS One. Aug. 25, 2014;9(8):e105238.

Ney, U.M., et al. "Anti-inflammatory effects of synthetic effects of synthetic retinoids may be related to their immunomodulatory action", Dermatologica, 175, Suppl. 1, 93-99, 1987.

Zhang, et al. "The preparation of 3,5-dihydroxy-4-isopropylstilbene nanoemulsion and in vitro release". International Journal of Nanomedicine, 6: 649-657 (2011).

Aromag, "Emulsifying Wax—How to Use Emulsifying Wax," Feb. 9, 2011 https://www.aromagregory.com/emulsifying-wax-how-to-use-emulsifying-wax/.

Zhao et al. "Randomized, double-blind, placebo-controlled, multiple-dose study of the safety, tolerability and pharmacokinetics of benvitimod, a candidate drug for the treatment of psoriasis" 2014, Journal of Clinical Pharmacy and Therapeutics 39:418-423.

Bowker, MJ et al., Drug solubilization with organi solvents, or using micellar solutions or other colloidal dispersed systems, Wermuth's The Practice of Medicinal Chemistry, Chapter 39, Academic Press, 2008, 786-812.

Joint COLIPA/EWF Recommendation; "Safety of Petrolatum as Raw Material For the Cosmetic Industry," Jul. 5, 2004.

Stubenrauch, C., Ed., Microemulsions—Background, New Concepts, Applications, Perspectives, Blackwell Publishing Ltd. 2009, chapter 9, 259-267.

Wikipedia entry for "Mineral oil," Apr. 20, 2015, available at https:en.wikipedia.org/w/index.php?title=mineral_oil&oldid=657255262.

EPO Communication of a Notice of Opposiiton in EP3297605, dated Feb. 8, 2023, 1-29.

* cited by examiner

| Lipid | Critical packing parameter $v/a_0 l_c$ | Critical packing shape | Structures formed |
|---|---|---|---|
| Single-chained lipids (surfactants) with large head-group areas: SDS in low salt | < 1/3 | Cone | Spherical micelles |
| Single-chained lipids with small head-group areas: SDS and CTAB in high salt, nonionics | 1/3–1/2 | Truncated cone | Cylindrical micelles |
| Double-chained lipids with large head-group areas, fluid chains: Phosphatidyl choline (lecithin), Phosphatidyl serine, Phosphatidyl glycerol, Phosphatidyl inositol, Phosphatidic acid, sphingomyelin, DGDG[a], dihexadecyl phosphate, dialkyl dimethyl ammonium salts | 1/2–1 | Truncated cone | Flexible bilayers, vesicles |
| Double-chained lipids with small head-group areas, anionic lipids in high salt, saturated frozen chains: phosphatidyl ethanolamine, phosphatidyl serine + $Ca^{2+}$ | ~1 | Cylinder | Planar bilayers |
| Double-chained lipids with small head-group areas, nonionic lipids, poly (cis) unsaturated chains, high T: unsat. phosphatidyl ethanolamine, cardiolipin + $Ca^{2+}$, phosphatidic acid + $Ca^{2+}$, cholesterol, MGDG[b] | >1 | Inverted truncated cone or wedge | Inverted micelles |

[a]DGDG, digalactosyl diglyceride, diglucosyl diglyceride.
[b]MGDG, monogalactosyl diglyceride, monoglucosyl diglyceride.

FIG. 2

TOPICAL PHARMACEUTICAL COMPOSITIONS

RELATED APPLICATIONS

This application claims the benefit of priority from U.S. Ser. No. 62/420,856, filed 11 Nov. 2016, and is a continuation-in-part application of U.S. Ser. No. 15/158,858, filed 19 May 2016, which claims the benefit of priority from provisional application U.S. Ser. No. 62/165,097, filed 21 May 2015, and U.S. Ser. No. 62/324,450, filed 19 Apr. 2016.

FIELD OF THE INVENTION

The present invention relates to topical pharmaceutical compositions.

BACKGROUND OF THE INVENTION

A challenge for the formulation chemist is to prepare a physically stable topical pharmaceutical composition where the active ingredient is also found to be chemically stable. Such pharmaceutical compositions should:
(i) not irritate the skin,
(ii) be specifically adapted to deliver the active ingredient onto or into the skin so as to treat a particular dermatological condition or disorder,
(iii) be cosmetically elegant to ensure that the patient complies with the prescribed treatment regimen,
(iv) provide penetration of the active ingredient to the appropriate layers of the skin and engage the desired target, and
(v) minimize systemic exposure while achieving local dermal/epidermal delivery.

One active ingredient of interest to be formulated in a physically and chemically stable topical composition is 3,5-Dihydroxy-4-isopropyl-trans-stilbene which has the following formula:

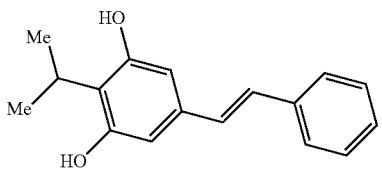 [SMILES: CC(C)c1c(O)cc(/C=C/c2ccccc2)cc1O]

This compound is also known as 5-[(E)-2-phenylethenyl]-2-(propan-2-yl)benzene-1,3-diol or 2-(1-Methyethyl)-5-[(1E)-2-phenylethenyl]-1,3-benzenediol.

3,5-Dihydroxy-4-isopropyl-trans-stilbene is believed to have been originally disclosed by Paul et al., *Journal of Chemical Ecology* 1981 7(3): 589-597 as an antibiotic. Li et al, *Applied and Environmental Microbiology* 1995 61(12): 4329-4333 also isolated the compound, but from a different bacterial strain and further demonstrated its fungicidal activity. The fungicidal activity of the compound was also described in WO 1995/003695 (Agro-Biotech Corporation). The compound is further described in WO 2001/042231 (Welichem Biotech Inc.) and in U.S. Pat. No. 7,868,047 and as being suitable for the treatment of various key dermatological conditions including psoriasis and inflammation. Example 3 of the U.S. Pat. No. 7,868,047 patent describes a cream formulation with an active ingredient being made in Galax Base. Applicants have been unable to ascertain any compendial notations or availability of a commercial cream base called "Galax" and therefore its composition remains unknown.

3,5-Dihydroxy-4-isopropyl-trans-stilbene is known to be sensitive to oxidation and photo degradation (see e.g. Gao et al., *Journal of Polymer Research* 2011 18: 1501-1508). Accordingly, there remains a need in the art for a topical composition comprising 3,5-Dihydroxy-4-isopropyl-trans-stilbene that is both chemically and physically stable, which delivers the active ingredient to the desired site of action in the epidermis and/or dermis, and which does not irritate the skin in use.

BRIEF DESCRIPTION OF THE DRAWINGS

FIG. 2 illustrates the mean dynamic packing shapes of lipids and the structures they form.

SUMMARY OF THE INVENTION

Figure 1:
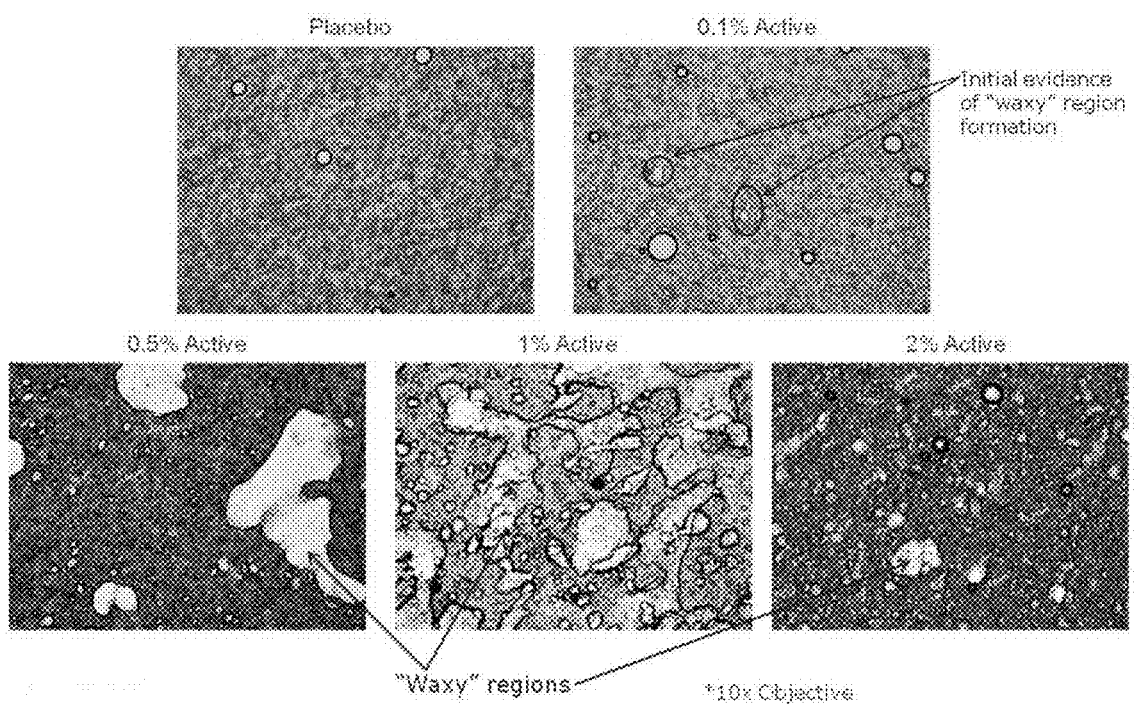
FIG. 1 illustrates the appearance of a non-uniform emulsion that was characteristic of Formulations 2-14.

In one embodiment, the present invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is homogeneous.

In one embodiment, the present invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is uniform.

In another embodiment, the active is solubilized in the oil phase of the emulsion composition. In another embodiment, the oil phase contains mineral oil and/or petrolatum. In another embodiment, if the oil phase contains mineral oil or petrolatum, then a second oil phase component is present, and if the oil phase contains both mineral oil and petrolatum than a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum at least a third oil phase component is present which is an ester or an ester of glycerin, suitably an ester of glycerin such as a medium chain triglyceride. In another embodiment, if the oil phase contains mineral oil then a second oil phase component is present which is an ester or an ester of glycerin, suitably an ester of glycerin such as a medium chain triglyceride.

In one embodiment, the present invention provides for a topical pharmaceutical emulsion composition comprising an effective amount of the active ingredient 3,5-Dihydroxy-4-isopropyl-trans-stilbene or a pharmaceutically acceptable salt thereof, an oil phase, a water phase, a surfactant, and an antioxidant, wherein the emulsion composition is homogeneous and the 3,5-Dihydroxy-4-isopropyl-trans-stilbene or pharmaceutically acceptable salt thereof is solubilized in the oil phase of the emulsion composition, and provided that if the oil phase contains mineral oil or petrolatum, then a second oil phase component is present, and if the oil phase contains both mineral oil and petrolatum then a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum at least a third oil phase component is present which is an ester and/or and ester of glycerin, suitably an ester of glycerin, such as a medium chain triglyceride. In another embodiment, if the oil phase contains mineral oil then a second oil phase component is present which is an ester and/or an ester of glycerin, suitably an ester of glycerin, such as a medium chain triglyceride.

In one embodiment, the present invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the active is solubilized in the oil phase of the emulsion composition. In another embodiment, the emulsion composition is homogeneous.

In another embodiment, the present invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is homogeneous and/or the active is solubilized in the oil phase of the emulsion composition.

In another embodiment, the present invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the average the average droplet size of the discontinuous phase is less than about 35 microns. In another embodiment, the average the average droplet size of the discontinuous phase is less than about 25 microns. In another embodiment, the average the average droplet size of the discontinuous phase is less than about 15 microns. In another embodiment, the average droplet size of the discontinuous phase is less than about 10 microns. In another embodiment, the average droplet size of the discontinuous phase is less than about 5 microns. In another embodiment, the average droplet size of the discontinuous phase is about or is less than about 1 micron. In another embodiment, the average droplet size of the discontinuous phase is from about 0.05 to about 1 micron. In another embodiment, the average droplet size of the discontinuous phase is from about 0.1 to about 0.75 microns. In another embodiment, the average droplet size of the discontinuous phase is about 0.5 microns.

In another embodiment, the present invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the average particle size of the oil phase is less than about 10 microns, and the emulsion composition is homogeneous and/or the active is solubilized in the oil phase of the emulsion composition.

In another embodiment, the invention provides a method of treating a dermatological condition or disorder in a patient in need thereof, the method comprising administering to said patient a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is homogeneous.

In another embodiment, the invention provides a method of treating a dermatological condition or disorder in a patient in need thereof, the method comprising administering to said patient a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is uniform.

In another embodiment, the active is solubilized in the oil phase of the emulsion composition. In another embodiment, the oil phase contains mineral oil and/or petrolatum. In another embodiment, if the oil phase contains mineral oil or petrolatum, then a second oil phase component is present, and if the oil phase contains both mineral oil and petrolatum than a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum at least a third oil phase component is present which is an ester or an ester of glycerin, suitably an ester of glycerin such as a medium chain triglyceride. In another embodiment, if the oil phase contains mineral oil then a second oil phase component is present which is an ester or an ester of glycerin, suitably an ester of glycerin such as a medium chain triglyceride.

In another embodiment, the invention provides a method of treating a dermatological condition or disorder in a patient in need thereof, the method comprising administering to said patient a topical pharmaceutical emulsion composition comprising an effective amount of the active ingredient 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and provided that if the oil phase contains mineral oil or petrolatum, then a second oil phase component is present, and if the oil phase contains both mineral oil and petrolatum than a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum then at least a third oil phase component is present which comprises an ester and/or an ester of glycerin, suitably an ester of glycerin, such as a medium chain triglyceride. In another embodiment, if the oil phase contains mineral oil then a second oil phase component is present which is an ester and/or an ester of glycerin, suitably an ester of glycerin, such as a medium chain triglyceride. In one embodiment, the dermatological condition or disorder is an inflammatory dermatological condition or disorder. In another embodiment, the inflammatory dermatological condition or disorder is atopic dermatitis and/or psoriasis, and/or acne.

In another embodiment, the invention relates to the use of a topical pharmaceutical emulsion composition comprising an effective amount of the active ingredient 3,5-Dihydroxy-4-isopropyl-trans-stilbene or a pharmaceutically acceptable salt thereof, an oil phase, a water phase, a surfactant, and an antioxidant, and wherein the emulsion is homogenous, for use in the treatment or prophylaxis of a dermatological condition or disorder in a human patient.

In another embodiment, the invention relates to the use of a topical pharmaceutical emulsion composition comprising an effective amount of the active ingredient 3,5-Dihydroxy-4-isopropyl-trans-stilbene or a pharmaceutically acceptable salt thereof; an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and provided that if the oil phase comprises mineral oil or petrolatum, then a second oil phase component is present, and if the oil phase contains both mineral oil and petrolatum than a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum at least a third oil phase component is present which is an ester and/or an ester of glycerin, suitably an ester of glycerin such as a medium chain triglyceride. In another embodiment, if the oil phase contains mineral oil then a second oil phase component is present which is an ester and/or an ester of glycerin, suitably an ester of glycerin, such as a medium chain triglyceride.

In another embodiment, the invention relates to a topical pharmaceutical emulsion composition comprising an effective amount of the active ingredient 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and provided that if the oil phase contains mineral oil or petrolatum, then a second oil phase component is present, and if the oil phase contains both mineral oil and petrolatum than a third oil phase component is present for use in the treatment or prophylaxis of a dermatological condition or disorder in a human patient. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum at least a third oil phase component is present which is an ester and/or an ester of glycerin, suitably an ester of glycerin such as a medium chain triglyceride. In another embodiment, if the oil phase contains mineral oil then a second oil phase component is present which is an ester and/or and ester of glycerin, suitably an ester of glycerin, such as a medium chain triglyceride.

In another embodiment, the invention relates to a method of reducing irritancy in a topical pharmaceutical emulsion composition containing the active ingredient 3,5-Dihydroxy-4-isopropyl-trans-stilbene or a pharmaceutically acceptable salt thereof in use in a patient in need thereof, the method comprising administering to the patient a pharmaceutical emulsion composition comprising an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and provided that if the oil phase contains mineral oil or petrolatum, then a second oil phase component is present, and if the oil phase contains both mineral oil and petrolatum than a third oil phase component is present. In one embodiment, the oil phase is substantially free from petrolatum. In another embodiment the oil phase contains ≤3%, or ≤2%, or ≤1% petrolatum. In another embodiment, if the oil phase contains both mineral oil and petrolatum at least a third oil phase component is present which is an ester and/or an ester of glycerin, suitably an ester of glycerin, such as a medium chain triglyceride. In another embodiment, if the oil phase contains mineral oil then a second oil phase component is present which is an ester and/or an ester of glycerin, suitably an ester of glycerin such as a medium chain triglyceride.

In one embodiment, the emulsion composition of the instant invention is compared to that of Formulation 1 or 12 (with comparable % w/w active).

In another embodiment, the invention relates to a method of improving the residency time of the active ingredient 3,5-Dihydroxy-4-isopropyl-trans-stilbene or a pharmaceutically acceptable salt thereof in the skin of a patient in need thereof, the method comprising administering to said patient a pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the emulsion composition is homogenous.

In another embodiment, the invention relates to a method of improving the residency time of the active ingredient 3,5-Dihydroxy-4-isopropyl-trans-stilbene or a pharmaceutically acceptable salt thereof in the skin of a patient in need thereof, the method comprising administering to said patient a pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and provided that if the oil phase contains mineral oil or petrolatum, then a second oil phase component is present, and if the oil phase contains both mineral oil and petrolatum than a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum at least a third oil phase component is present which is an ester and/or an ester of glycerin, suitably an ester of glycerin such as a medium chain triglyceride. In another embodiment, if the oil phase contains mineral oil then a second oil phase component is present which is which is an ester and/or an ester of glycerin, suitably an ester of glycerin such as a medium chain triglyceride. In one embodiment, the emulsion composition of the instant invention is compared to that of the Formulation 1 or 12 (with comparable % w/w of active ingredient).

In another embodiment, the invention relates to a method of improving the residency time of the active ingredient 3,5-Dihydroxy-4-isopropyl-trans-stilbene or a pharmaceutically acceptable salt thereof in the skin of a patient in need thereof, the method comprising administering to said patient a pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, and wherein the emulsion is homogeneous and/or the active is solubilized in the oil phase. In another embodiment, the average droplet size of the discontinuous phase is about 5 microns or less. In another embodiment, the average droplet size of the discontinuous phase is about 1 micron or less.

In another embodiment, the invention relates to a method of reducing side effects in a patient who is administered a composition containing 3,5-Dihydroxy-4-isopropyl-trans-stilbene or a pharmaceutically acceptable salt thereof, the method comprising administering to the patient a pharmaceutical emulsion composition comprising an oil phase, a water phase, a surfactant, and an antioxidant, and wherein the emulsion is homogenous and/or the active is solubilized in the oil phase. In another embodiment, the average droplet size of the discontinuous phase is about 5 microns or less. In another embodiment, the average droplet size of the discontinuous phase is about 1 micron or less.

In another embodiment, the invention relates to a method of reducing side effects in a patient who is administered a composition containing 3,5-Dihydroxy-4-isopropyl-trans-stilbene or a pharmaceutically acceptable salt thereof, the method comprising administering to the patient a pharmaceutical emulsion composition comprising an oil phase, a water phase, a surfactant, and an antioxidant, and wherein the 3,5-Dihydroxy-4-isopropyl-trans-stilbene or pharmaceutically acceptable salt thereof is solubilized in the oil phase of the emulsion composition, and provided that if the oil phase contains mineral oil or petrolatum, then a second oil phase component is present, and if the oil phase contains both mineral oil and petrolatum than a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum at least a third oil phase component is present which is an ester and/or and ester of glycerin, suitably an ester of glycerin such as a medium chain triglyceride. In another embodiment, if the oil phase contains mineral oil then a second oil phase component is present which is an ester and/or and ester of glycerin, suitably an ester of glycerin such as a medium chain triglyceride. In one embodiment, the emulsion composition of the instant invention is compared to that of Formulation 1 or 12, or a similar formulation with equivalent active ingredient present.

In one embodiment, the present invention provides for a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition. In one embodiment, the oil phase contains mineral oil and/or petrolatum. In another embodiment, if the oil phase contains mineral oil, then a second oil phase component other than petrolatum is present in the composition. In another embodiment, if the oil phase contains petrolatum, then a second oil phase component other than mineral oil is present in the composition. In any of these embodiments it is preferable that the resulting emulsion does not contain non-uniform areas or waxy regions upon storage.

In one embodiment, the present invention provides for a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and wherein if the oil phase contains mineral oil, then a second oil phase component other than petrolatum is present in the composition.

In an embodiment, the invention provides for a topical pharmaceutical emulsion composition comprising 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and wherein if the oil phase contains mineral oil then a second oil phase component other than petrolatum is present in the composition, or if the oil phase contains both mineral oil and petrolatum at least a third oil phase component is present. In another embodiment, the oil phase is substantially free from mineral oil and/or petrolatum.

In one embodiment, the present invention provides for a topical pharmaceutical 0/W emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and the composition is formulated as a cream or lotion. In another embodiment, the cream or lotion is homogenous and uniform in appearance.

DETAILED DESCRIPTION OF THE INVENTION

In addition to creating a physically and chemically stable pharmaceutical formulation, the present invention also provides for a pharmaceutical formulation which is non-irritating to the skin upon application and use, or is one which is less irritating than any previous formulations used in the development of the active ingredient to date. Another aspect of the invention is a formulation that not only has superior skin penetration and target engagement of the appropriate receptors, but also has significant non-systemic exposure of the active ingredient to the patient upon application and use.

The active ingredient 3,5-Dihydroxy-4-isopropyl-trans-stilbene has caused a number of issues with respect to formulating the compound in a topical formulation. Many formulations exhibited "waxy" regions, seen only in the presence of the active ingredient, and which further were dependent upon the concentration of the active ingredient in the formulation. Waxy regions may also be referred to herein as non-uniform emulsions. In one embodiment, the uniform emulsion includes none, or less than 1% of the active ingredient in crystalline form. As consistency and manufacturability are necessary for commercial batches, a final product with container/tube content homogeneity under higher temperatures and storage is needed.

Various approaches to correct these problems have been investigated. One approach is disclosed in a patent application to GlaxoSmithKline Intellectual Property Development Limited, Sonti et al., PCT/IB2016/052955 and U.S. application Ser. No. 15/158,858 both filed May 19, 2016, whose disclosures are incorporated by reference herein. In these applications, one approach was taken to decrease the amount of mineral oil and/or petrolatum present, in the formulation (if at all present to start with), and to use as an oil phase component, suitably an ester and/or an ester of glycerin, such as a medium chain triglyceride which would assist in solubilizing the active ingredient. This approach produced a uniform and homogenous emulsion.

However, it is also possible to eliminate the waxy regions, without affecting penetration and release profiles by other modifications to the formulation as further described herein.

The active ingredient was believed to cause the emulsion destabilization by perhaps interacting at the surfactant interface (liquid crystals). As can be seen in the formulations shown in FIG. 1 the presence of the active ingredient appears to be altering the system in some manner. The non-uniform emulsions illustrated in FIG. 1 were determined to be dependent on the concentration of the active ingredient. Thus, one approach to correcting the waxy regions is to optimize the surfactant system rather than to change the oil phase components as described in Sonti et al. supra above.

The surfactant molecular geometry model can be used to generally explain emulsion stabilization. In FIG. 2 the Mean (Dynamic Packing Shapes of Lipids and the Structures they form are graphically shown.

Figure 11:
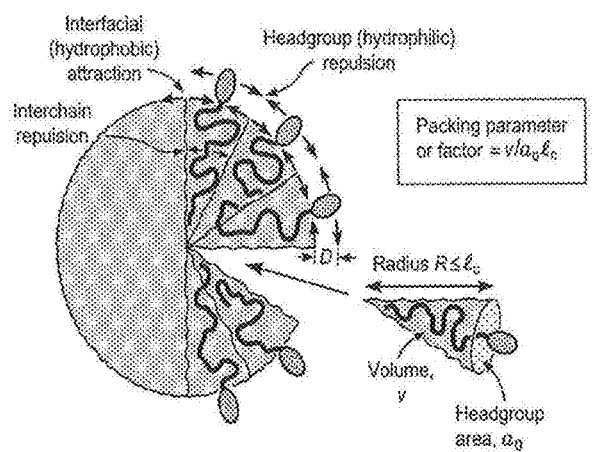
FIG. 11 illustrates a visualization of packing parameters.

Using this model, it can be seen that different surfactants have produced different shapes. Based upon the structure of the surfactant molecule, a packing parameter can be estimated. See FIG. 11 for a visualization of the packing parameter. Molecules with different packing parameters will form different supramolecular structures, i.e. micelles, or bilayers in water, etc.

The present invention starts with an oil-in-water emulsion system. Using the idea of packing parameters of the surfactants it was possible to look at which surfactants might stabilize and o/w emulsion versus that of a w/o emulsion. When you use a mixture of surfactants, you need to estimate the average packing parameter from the molar quantities of the different surfactants. It was hypothesized that the active ingredient can act as a surfactant and affect the average packing parameter leading to change in micellar size and structure. Hence, optimization of choice and ratio of surfactants in the presence of differing active ingredient concentration can result in a homogenous emulsion.

Looking at the components in Formulation 1 for instance, you have 4 surfactants present. Steareth 2, Steareth 20, Non-emulsifying wax and polysorbate 80. It is believed that Steareth-2 would produce (as shown in FIG. 2) an inverted micelle; Steareth –20 would produce a spherical micelle, polysorbate –80 would produce a cyclical micelle. Too much of a material that has a similar packing parameter is hypothesized as changing the curvature of the droplet based upon experimentation shown herein.

In an embodiment, the invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is homogenous.

In an embodiment, the invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is homogenous or uniform, upon ICH storage conditions.

In an embodiment, the invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is homogenous. In one embodiment, the 3,5-Dihydroxy-4-isopropyl-trans-stilbene or pharmaceutically acceptable salt thereof is solubilized in the oil phase of the emulsion composition. In another embodiment, if the oil phase contains mineral oil or petrolatum, then a second oil phase component is present, and if the oil phase contains both mineral oil and petrolatum than a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum then at least a third oil phase component is present which is an ester and/or an ester of glycerin, suitably an ester of glycerin, such as a medium chain triglyceride. In another embodiment, if the oil phase contains mineral oil, then a second oil phase component is present which is an ester and/or an ester of glycerin, suitably an ester of glycerin, such as a medium chain triglyceride. The second oil phase component and the third oil phase component are used as co-solvents for the active ingredient in the oil phase of the emulsion composition. That is, the second and third oil phase components act as oil miscible co-solvents.

In one embodiment, the amount of the active ingredient solubilized in the oil phase of the emulsion composition is present in an amount of ≥50% w/w, or ≥60% w/w, or ≥70% w/w, or ≥80% w/w, or ≥90% w/w or ≥95% w/w or ≥98% w/w, based on the percent by weight of the active ingredient. In a preferred embodiment ≥95% or ≥98% w/w of the active ingredient is solubilized in the oil phase of the emulsion, producing a homogenous composition.

In an alternative embodiment, the 3,5-Dihydroxy-4-isopropyl-trans-stilbene or a pharmaceutically acceptable salt thereof is solubilized in the water phase of the emulsion composition. Since 3,5-Dihydroxy-4-isopropyl-trans-stilbene is not soluble in water, a water miscible organic solvent (i.e. a water miscible co-solvent may used to solublize the active ingredient in the water phase of the emulsion). Suitably, the active ingredient solubilized in the water phase of the emulsion composition is present in an amount ≥10% w/w, or ≥20% w/w, or ≥30% w/w, or ≥40% w/w, or ≥50% w/w, or ≥60% w/w, or ≥70% w/w, or ≥80% w/w, or ≥90% w/w or ≥95% w/w, based on the percent by weight of the active ingredient. In one embodiment, a water miscible co-solvent is selected from Propylene glycol, Transcutol, or PEG 400, or combinations or mixtures thereof.

When used herein, the term "D90" refers to the oil droplet size diameter of which 90% of the droplets are less than a particular size. Alternatively, the term "D90" is defined as the size in microns below which 90 percent of the oil droplets reside on a volume basis. In an embodiment, the D90 of the average droplet size of the discontinuous phase in the composition is less than 15 microns. In another embodiment, the average droplet size of the discontinuous phase according to the present invention have a D90 of less than 5 microns. In another embodiment, the D90 of the average droplet size of the discontinuous phase in the composition is between about 0.1 and about 5 microns. In another embodiment. In another embodiment, the D90 of the average droplet size of the discontinuous phase in the composition is between about 0.5 and 1 micron. In another embodiment, the D90 of the average droplet size of the discontinuous phase in the composition is between about 0.1 and 5 microns.

When used herein, the term "D50" refers to the median or $50^{th}$ percentile of which the droplets are less than a particular size. Alternatively, the term "D50" is defined as the size in microns below which 50 percent of the oil droplets reside on a volume basis. In an embodiment, the D50 of the average droplet size of the discontinuous phase (oil phase) in the composition is less than 5 microns. In another embodiment, the average droplet size of the discontinuous phase according to the present invention have a D50 of less than 1 micron. In another embodiment, the D50 of the average droplet size of the discontinuous phase in the composition is between about 0.1 and about 5 microns. In another embodiment. In another embodiment, the D50 of the average droplet size of the discontinuous phase in the composition is between about 0.5 and 1 micron. In another embodiment, the D50 of the average droplet size of the discontinuous phase in the composition is between about 0.1 and 5 microns.

When used herein, the term "D10" refers to the oil droplet size diameter of which 10% of the droplets are less than a particular size. Alternatively, the term "D10" is defined as the size in microns below which 10 percent of the oil droplets reside on a volume basis.

Methods for measuring oil droplet size distribution are well known in the art. In one embodiment, oil droplet size diameter distribution oil droplet size in the composition according to the present invention may be measured using a laser diffraction techniques. Suitable laser diffraction apparatus includes, for example, the Sympatec HELOS/QUIXEL, or the Malvern Laser Diffractonamer obtainable from Malvern Instruments, Malvern, UK as well as others.

In one embodiment, the present invention provides for a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the average droplet size of the discontinuous phase is less than about 35 microns. In another embodiment, the average droplet size of the discontinuous phase is less than about 25 microns. In another embodiment, the average droplet size of the discontinuous phase is less than about 15 microns. In another embodiment, the average droplet size of the discontinuous phase is less than about 10 microns. In another embodiment, the average droplet size of the discontinuous phase is less than about 5 microns. In another embodiment, the average droplet size of the discontinuous phase is about or is less than about 1 micron. In another embodiment, the average droplet size of the discontinuous phase is from about 0.05 to about 35 microns. In another embodiment, the average droplet size of the discontinuous phase is from about 0.05 to about 5 micron. In another embodiment, the average droplet size of the discontinuous phase is from about 0.05 to about 1 micron. In another embodiment, the average droplet size of the discontinuous phase is from about 0.1 to about 0.75 microns.

In another embodiment, the D50 of the discontinuous phase is from about 0.05 to about 5 microns.

In another embodiment, the D90 of the discontinuous phase is from about 0.05 to about 1 micron.

In another embodiment, the D90 of the discontinuous phase is from about 0.1 to about 0.75 micron.

In another embodiment, the average droplet size of the discontinuous phase is from about 0.5 to about 1 micron.

In another embodiment, the average droplet size of the discontinuous phase is from about 0.1 to about 5 microns.

In another embodiment, the average droplet size of the discontinuous phase is from about 0.1 to about 1 micron.

In one embodiment, at least 90% of the droplets in the oil phase of the oil-in-water emulsion (e.g. the discontinuous phase) have a droplet size of about or less than 1 micron. In another embodiment, at least 95, 97, 98, or 99% of the droplets are about or less than 1 micron. In one embodiment, at least 90% of the droplets in the oil phase of the oil-in-water emulsion (e.g. the discontinuous phase) have a droplet size of about or less than 1 micron to about 0.1 microns. In another embodiment, at least 95, 97, 98, or 99% of the droplets are about or less than 1 micron to about 0.1 microns.

Alternatively, or at least in addition to, at least about 75%, or at least about 85%, or at least about 90%, of the droplet size of the discontinuous phase oil in the oil-in-water emulsion have a size of less about 10 microns, or less that about 5 microns or less than about 1 micron, or less than about 0.75 microns. Alternatively, or at least in addition to, at least about 75%, or at least about 85%, or at least about 90%, of the droplet size of the discontinuous phase oil in the oil-in-water emulsion have a size of less about 10 microns, or less that about 5 microns or less than about 1 micron, or less than about 0.75 microns, or less than 0.5 microns to about 0.1 microns. Any combination of the above percentages and droplet sizes may be used to define oil droplets in a composition of the present invention.

In one embodiment, the emulsion composition of the present invention suitably have at least one of the following characteristics: a D50 of mean droplet diameter of less than 1 micron when measured at 2-8 degrees ° C.; and/or when measured at 25 degrees ° C. and 60% RH, and/or when measured at 30 degrees ° C. at 6 months; or both a D50 mean droplet diameter of less than 1 micron when measured at 30 degrees ° C. at 6 months.

In another embodiment, a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the average droplet size of the oil phase is less than about 5 microns and optionally the emulsion is homogenous. In another embodiment, the active is solubilized in the oil phase.

In another embodiment, a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the average droplet size of the oil phase is less than about 5 microns to about 0.1 microns; and wherein the emulsion is homogenous, and the active is solubilized in the oil phase.

In another embodiment, a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the average droplet size of the oil phase is less than about 1 micron and optionally the emulsion is homogenous. In another embodiment, the active is solubilized in the oil phase.

In another embodiment, a topical pharmaceutical emulsion composition comprising the active ingredient 3,5-Dihydroxy-4-isopropyl-trans-stilbene or a pharmaceutically acceptable salt thereof, an oil phase, a water phase, a surfactant, and an antioxidant, and wherein the average droplet size of the oil phase is less than about 1 micron to about 0.1 microns; and the emulsion is homogenous, and the active is solubilized in the oil phase.

The terms "emulsion" and "oil-in-water emulsion" as used herein, and unless otherwise stated or understood from the context used, refers to a colloidal dispersion system in which liquid oil is dispersed as droplets (the discrete phase, also referred to as "the discontinuous non-aqueous phase" or "the discontinuous phase") in a continuous aqueous medium (the continuous phase, also referred to as "the continuous aqueous phase" or "the continuous phase"). In some embodiments, at least 50% of the active ingredient (w/w) is dissolved and remains in the emulsion. In some embodiments, at least 75% of the active ingredient (w/w) is dissolved and remains in the emulsion. In certain embodiments, as is further described herein, greater than 85% of the active ingredient is present in the discontinuous phase.

3,5-Dihydroxy-4-isopropyl-trans-stilbene

In an embodiment, the 3,5-Dihydroxy-4-isopropyl-trans-stilbene or a pharmaceutically acceptable salt thereof is present in the emulsion composition in an amount from about 0.01% to about 5% by weight, such as from about 0.05% to about 2% by weight, based on the total weight of the composition. In another embodiment, the 3,5-Dihydroxy-4-isopropyl-trans-stilbene or a pharmaceutically acceptable salt thereof is present in an amount from about 0.1% to about 1.0% by weight, based on the total weight of the composition. In an embodiment, the 3,5-Dihydroxy-4-isopropyl-trans-stilbene or a pharmaceutically acceptable salt thereof is present in an amount of about 0.25%, 0.30%, 0.40%, 0.50%, 0.75%, 1% or 2% by weight, based on the total weight of the composition. In one embodiment, the 3,5-Dihydroxy-4-isopropyl-trans-stilbene or a pharmaceutically acceptable salt thereof is present in an amount of about 0.25% to about 0.50% by weight.

Oil Phase

The present topical pharmaceutical emulsion compositions comprise an oil phase. Suitably, the oil phase comprises one or more oils and/or fats.

Exemplary oils and fats include fatty acids, esters, esters of glycerin, fatty alcohols, waxes, sterols, unsaponifiables, siloxanes, silanes, lanolin, hydrocarbons, essential oils, vegetable oils, mineral oils, animal oils and edible oils, and mixtures thereof.

In an embodiment, the oil and/or fat is selected from the group consisting of an ester and an ester of glycerin, and mixtures thereof. In another embodiment, the oil and/or fat is at least an ester of glycerin.

In an embodiment, the oil phase comprises a fatty acid. Exemplary fatty acids include, but are not limited to, isostearic acid, oleic acid, stearic acid, linoleic acid, linolenic acid, myristic acid, palmitic acid, ricinoleic acid and arachidic acid, and mixtures thereof.

In an embodiment, the oil phase comprises an ester. Exemplary esters include, but are not limited to, cocoaprylate/caprate, diethyl sebacate, diisopropyl adipate, diisopropyl dilinoleate, ethyl oleate, ethylhexyl hydroxystearate, glycol distearate, glycol stearate, hydroxyoctacosanyl hydroxystearate, isopropyl isostearate, isopropyl myristate, isopropyl palmitate, isopropyl stearate, methyl glucose sesquistearate, methyl laurate, methyl salicylate, methyl stearate, myristyl lactate, octyl salicylate, oleyl oleate, PPG-20 methyl glucose ether distearate, propylene glycol diacetate, propylene glycol dicaprylate, propylene glycol monolaurate, propylene glycol monopalmitostearate, propylene glycol ricinoleate, triacetin and sucrose distearate, and mixtures thereof. In one embodiment, the ester is diethyl sebacate or diisopropyl adipate.

In an embodiment, the oil phase comprises an ester of glycerin. Exemplary esters of glycerin include, but are not limited to, caprylic/capric glycerides, caprylic/capric triglyceride, caprylic/capric/succinic triglyceride, capryl glucoside, cetearyl glucoside, cocoglycerides, decyl glucoside, lauryl glucoside, glyceryl citrate, glyceryl isostearate, glyceryl laurate, glyceryl monostearate, glyceryl oleate, glyceryl palmitate, glyceryl ricinoleate, glyceryl stearate, mono and diglyceride, PEG-12 glyceryl laurate, PEG-120 glyceryl stearate, polyglyceryl-3 oleate, polyoxyl glyceryl stearate, tallow glycerides and medium chain triglycerides (MCT), and mixtures thereof. In one embodiment, the oil phase of the emulsion comprises medium chain triglycerides. In one embodiment, the medium chain triglyceride carbon length is from C6 to C12. In another embodiment, the medium chain triglyceride carbon length is from C6 to C8.

In an embodiment, the oil phase comprises a fatty alcohol. Exemplary fatty alcohols include, but are not limited to, caprylic alcohol, decyl alcohol, lauryl alcohol, myristyl alcohol, behenyl alcohol, lanolin alcohol, arachidyl alcohol, oleyl alcohol, palm alcohol, isocetyl alcohol, cetyl alcohol and stearyl alcohol, mixtures thereof. In one embodiment, the fatty alcohol is a mixture of cetyl alcohol and stearyl alcohol. Suitably, the ratio of cetyl alcohol to stearyl alcohol is about 2:1 to about 1:9.

In an embodiment, the oil phase comprises a wax. Exemplary waxes include, but are not limited to, beeswax, carnauba wax, dimethicone PEG-1 beeswax, dimethiconol beeswax, lanolin wax, microcrystalline wax, white wax, candelilla wax, paraffin wax, emulsifying wax, PEG-8 beeswax, yellow wax, cetyl esters wax, shellac wax and synthetic beeswax, and mixtures thereof.

In an embodiment, the oil phase comprises a sterol. Exemplary sterols include, but are not limited to, *Brassica Campestris* sterols, $C_{10}$-$C_{30}$ cholesterol/lanosterol esters, canola sterols, cholesterol, lanolin cholesterols, *Glycine soja* sterols, PEG-20 phytosterol and phytosterols, and mixtures thereof.

In an embodiment, the oil phase comprises a siloxane and/or silane. Exemplary siloxanes and silanes include, but are not limited to, dimethicone, cyclomethicone, simethicone, phenyl dimethicone, cyclopentasiloxane, cyclotetrasiloxane, dimethyl siloxane and dimethicone cross polymer, and mixtures thereof.

In an embodiment, the oil phase comprises a hydrocarbon. Exemplary hydrocarbons include, but are not limited to, dodecane, petrolatum, squalane, squalene and paraffin, and mixtures thereof.

In an embodiment, the oil phase comprises an essential oil. Exemplary essential oils include, but are not limited to, primrose oil, rose oil, *eucalyptus* oil, borage oil, bergamot oil, chamomile oil, citronella oil, lavender oil, peppermint oil, pine oil, pine needle oil, spearmint oil, tea tree oil and wintergreen oil, and mixtures thereof.

In an embodiment, the oil phase comprises a vegetable oil. Exemplary vegetable oils include, but are not limited to, almond oil, aniseed oil, canola oil, castor oil, coconut oil, corn oil, avocado oil, cottonseed oil, olive oil, palm kernel oil, peanut oil, sunflower oil, safflower oil and soybean oil, and mixtures thereof.

In an embodiment, the oil phase may comprise a mineral oil. Exemplary mineral oils include, but are not limited to, mineral oil and light mineral oil. If the oil phase comprises mineral oil, there is another oil phase component present in the formulation. In one embodiment, the second oil phase component will not be petrolatum. In one embodiment, the second oil phase component will not be a petrolatum derivative. In one embodiment, the emulsion composition comprises an oil phase that is substantially free from mineral oil. In another embodiment, the oil phase is substantially free from petrolatum. In another embodiment, the oil phase is substantially free from a petrolatum derivative. In another embodiment, the emulsion composition comprises an oil phase that is substantially free from mineral oil and petrolatum. In another embodiment, the emulsion composition comprises an oil phase that is substantially free from mineral oil, petrolatum and a petrolatum derivative.

In an embodiment, the oil phase comprises an edible oil. Exemplary edible oils include, but are not limited to, cinnamon oil, clove oil, lemon oil and peppermint oil, and mixtures thereof.

In one embodiment, the oil phase of the emulsion comprises an ester of glycerin which is a medium chain triglycerides (MCT). Suitably, the MCT is present in an amount from about 2% to about 30% by weight, based on the total weight of the composition, such as about 2%, about 5%, about 10%, about 15%, about 20%, about 25% or about 30% by weight, based on the total weight of the composition. In another embodiment, the oil phase of the emulsion comprises MCT in an amount from about 5% to about 30% by weight, based on the total weight of the composition. In another embodiment, the oil phase of the emulsion comprises MCT in an amount from about 5% to about 20% by weight, based on the total weight of the composition. In another embodiment, the MCT is present in an amount of about 10% by weight, based on the total weight of the composition.

In one embodiment, the oil phase comprises an oil and/or fat in an amount from about 5% to about 45% by weight, such as from about 5% to about 35% by weight, based on the total weight of the composition. In another embodiment, the oil phase comprises an oil and/or fat in an amount from about 5% to about 25% by weight, based on the total weight of the composition. In yet another embodiment, the oil phase comprises an oil and/or fat in an amount from about 5% to about 15% by weight, based on the total weight of the composition.

Water Phase

The present topical pharmaceutical emulsion compositions comprise an aqueous or water phase comprising water. In one embodiment, the aqueous phase consists of water alone. In another embodiment, the aqueous phase includes one or more water miscible co-solvents. Suitably, the water phase is present in the composition in an amount from about 25% to about 85% by weight, based on the total weight of the composition. In an embodiment, the water phase is present in the composition in an amount from about 30% to about 80% by weight, based on the total weight of the composition. In another embodiment, the water phase is present in an amount from about 55% to about 75% by weight, based on the total weight of the composition.

In yet another embodiment, the 'water phase' is composed not of water but of aprotic solvents e.g. polar, leading to anhydrous formulations.

In one embodiment, the present invention provides for a topical pharmaceutical O/W emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition, and composition contains less than 15% w/w short chain, lower molecular weight alcohols, such as a $C_{1-4}$ alcohol. A short chain alcohol includes, ethanol, methanol, i-propanol, 1,2-propanediol, and n-butanol. his includes, one embodiment, the amount of alcohol present in the composition is less than 10% w/w. In another embodiment, the amount of alcohol present in the composition is less than 5% w/w. In another embodiment, the amount of alcohol present in the composition is less than 2% w/w. In another embodiment, the amount of alcohol present in the composition is less than 1% w/w. In another embodiment, the composition is free from alcohol. In another embodiment, the composition is formulated as a cream or lotion.

Surfactant

The topical pharmaceutical emulsion compositions comprise a surfactant. In an embodiment, the surfactant is a mixture of two or more surfactants. As used herein, a surfactant is a compound that lowers the surface tension between two liquids or between a liquid and a solid. Surfactants may also act as detergents, wetting agents, emulsifiers, foaming agents, and dispersants. As further used herein, an emulsifier is equivalent to a surfactant.

Suitably, the surfactant is present in the composition in an amount from about 1% to about 20% by weight, such as from about 5% to about 15% by weight, based on the total weight of the composition.

A surfactant's hydrophilic/lipophilic balance (HLB) describes the surfactant's affinity toward water or oil. The HLB scale ranges from 1 (totally lipophilic) to 20 (totally hydrophilic), with 10 representing an equal balance of both characteristics. Lipophilic surfactants tend to form water-in-oil (w/o) emulsions, and hydrophilic surfactants tend to form oil-in-water (o/w) emulsions. The HLB of a blend of two surfactants equals the weight fraction of surfactant "A" times its HLB value plus the weight fraction of surfactant B times its HLB value (weighted average).

In one embodiment, the surfactant comprises one or more non-ionic surfactants. In another embodiment, the surfactant comprises two or more non-ionic surfactants and the weighted average of the HLB values of the two or more non-ionic surfactants is from about 10 to about 20. In yet another embodiment, the surfactant comprises two or more non-ionic surfactants and the weighted average of the HLB values of the two or more non-ionic surfactants is from about 1 to about 10.

Suitable non-ionic surfactants according to the invention include, but are not limited to, ethoxylated fatty alcohol ethers, PEG castor oils, PEG esters, propylene glycol esters, glyceryl esters and derivatives, polymeric ethers, sorbitan derivatives, fatty alcohols, emulsifying waxes, and mixtures thereof. In one embodiment, non-ionic surfactants include, ethoxylated fatty alcohol ethers, PEG esters, propylene glycol esters, glyceryl esters and derivatives, polymeric ethers, sorbitan derivatives, fatty alcohols, emulsifying waxes, and mixtures thereof. In another embodiment, non-ionic surfactants include, ethoxylated fatty alcohol ethers, propylene glycol esters, glyceryl esters and derivatives, polymeric ethers, sorbitan derivatives, fatty alcohols, emulsifying waxes, and mixtures thereof.

In an embodiment, the non-ionic surfactant is an ethoxylated fatty alcohol ether. Exemplary ethoxylated fatty alcohol ethers include, but are not limited to, steareth-2, steareth-10, steareth-20, steareth-21, steareth-40, steareth-100, beheneth-10, ceteareth-2, ceteareth-3, ceteareth-5, ceteareth-6, ceteareth-10, ceteareth-12, ceteareth-15, ceteareth-20, ceteareth-21, ceteareth-22, ceteareth-25, ceteareth-30, ceteareth-31, ceteareth-32, ceteareth-33, ceteth-2, ceteth-10, ceteth-20, ceteth-23, choleth-24, isoceteth-20, laureth-2, laureth-3, laureth-4, laureth-5, laureth-9, laureth-10, laureth- 12, laureth-15, laureth-20, laureth-21, laureth-22, laureth-23, nonoxynol-9, nonoxynol-15, octoxynol-1, octoxynol-9, oleth-2, oleth-5, oleth-10, oleth-20, C20-40 pareth-24 and trideceth-10, and mixtures thereof.

In an embodiment, the non-ionic surfactant is a PEG castor oil. Exemplary PEG castor oils include, but are not limited to, PEG-7 hydrogenated castor oil, PEG-25 hydrogenated castor oil, PEG-30 castor oil, PEG-33 castor oil, PEG-35 castor oil, PEG-36 castor oil, PEG-40 castor oil, PEG-40 hydrogenated castor oil, PEG-50 castor oil, PEG-54 hydrogenated castor oil, PEG-60 castor oil and PEG-60 hydrogenated castor oil, and mixtures thereof.

In an embodiment, the non-ionic surfactant is a PEG ester. Exemplary PEG esters include, but are not limited to, PEG-4 dilaurate, PEG-150 distearate, PEG-12 glyceryl laurate, PEG-120 glyceryl stearate, PEG-6 isostearate, PEG-4 laurate, PEG-8 laurate, PEG-20 methyl glucose sesquistearate, PEG-5 oleate, PEG-6 oleate, PEG-10 oleate, PEG-25 propylene glycol stearate, PEG-2 stearate, PEG-6 stearate, PEG-6-32 stearate, PEG-8 stearate, PEG-9 stearate, PEG-20 stearate, PEG-40 stearate, PEG-45 stearate, PEG-50 stearate and PEG-100 stearate, and mixtures thereof.

In an embodiment, the non-ionic surfactant is a propylene glycol ester. Exemplary propylene glycol esters include, but are not limited to, propylene glycol laurate, propylene glycol palmitostearate, propylene glycol ricinoleate and propylene glycol stearate, and mixtures thereof.

In an embodiment, the non-ionic surfactant is a glyceryl ester or derivative. Exemplary glyceryl esters and derivatives include, but are not limited to, glyceryl behenate, glyceryl dibehenate, glyceryl dioleate, glyceryl distearate, glyceryl isostearate, glyceryl laurate, glyceryl linoleate, glyceryl monostearate, glyceryl oleate, glyceryl palmitate, glyceryl ricinoleate, glyceryl stearate, PEG-23 glyceryl cocoate, PEG-6 caprylic/capric glycerides, PEG-7 glyceryl cocoate, polyglyceryl-10 diisostearate, polyglyceryl-2 diisostearate, polyglyceryl-3 diisostearate and polyglyceryl-6 diisostearate, PEG-12 glyceryl laurate, PEG-120 glyceryl stearate, and mixtures thereof.

In an embodiment, the non-ionic surfactant is a polymeric ether. Exemplary polymeric ethers include, but are not limited to, poloxamer 124, poloxamer 181, poloxamer 182, poloxamer 184, poloxamer 188, poloxamer 237, poloxamer 331, poloxamer 338 and poloxamer 407, and mixtures thereof.

In an embodiment, the non-ionic surfactant is a sorbitan derivative. Exemplary sorbitan derivatives include, but are not limited to, polysorbate 20, polysorbate 40, polysorbate 60, polysorbate 65, polysorbate 80, sorbitan isostearate, sorbitan monolaurate, sorbitan monooleate, sorbitan monopalmitate, sorbitan monostearate, sorbitan sesquioleate, sorbitan trioleate and sorbitan tristearate, and mixtures thereof.

In an embodiment, the non-ionic surfactant is a fatty alcohol. Exemplary fatty alcohols include, but are not limited to, isostearyl alcohol, caprylyl alcohol, decyl alcohol, lauryl alcohol, myristyl alcohol, behenyl alcohol, lanolin alcohol, arachidyl alcohol, oleyl alcohol, palm alcohol, isocetyl alcohol, cetyl alcohol, stearyl alcohol and cetearyl alcohol, and mixtures thereof. In one embodiment, the fatty alcohol is a mixture of cetyl alcohol and stearyl alcohol, known as cetearyl alcohol (also known as cetostearyl alcohol).

In an embodiment, the non-ionic surfactant is an emulsifying wax, e.g. a non-ionic emulsifying wax also known as emulsifying wax NF, or emulsifying wax BP. In an embodiment, the emulsifying wax is a mixture of cetearyl alcohol and polysorbate 60. In another embodiment, the emulsifying wax is a proprietary blend known as POLAWAX NF (Croda Inc, Edison, N.J., USA).

In one embodiment, the surfactant comprises one or more ethoxylated fatty alcohol ethers. In another embodiment, the ethoxylated fatty alcohol ether is a mixture of steareth-2 and steareth-20.

In one embodiment, the surfactant comprises a mixture of an ethoxylated fatty alcohol ether and a sorbitan derivative. In another embodiment, the mixture of an ethoxylated fatty alcohol ether and a sorbitan derivative is a mixture of steareth-2, steareth-20 and polysorbate 80.

In one embodiment, when there are 2 surfactants present in the formulation, each surfactant is present in an amount from about 0.5% to about 5% by weight, based on the total weight of the composition. In another embodiment, when there are 3 surfactants present in the formulation, each surfactant is present in an amount from about 0.5% to about 5% by weight, based on the total weight of the composition. Similarly, if there are 4 or more surfactants present they are each present in an amount from about 0.5% to about 5% by weight, based on the total weight of the composition.

In one embodiment, the surfactant comprises a mixture of an ethoxylated fatty alcohol ether and an emulsifying wax. In another embodiment, the surfactant comprises a mixture of an ethoxylated fatty alcohol ether, a sorbitan derivative and an emulsifying wax. Suitably, the mixture of an ethoxylated fatty alcohol ether and an emulsifying wax is a mixture of steareth-2, steareth-20, and POLAWAX NF. Suitably, the mixture of an ethoxylated fatty alcohol ether, a sorbitan derivative and an emulsifying wax is a mixture of steareth-2, steareth-20, polysorbate 80 and POLAWAX NF. In an alternative embodiment, the surfactant comprises a mixture of an ethoxylated fatty alcohol ether and a fatty alcohol. Suitably, the mixture of an ethoxylated fatty alcohol ether and a fatty alcohol is a mixture of steareth-2, steareth-20, and cetearyl alcohol.

In another embodiment, the surfactant comprises a mixture of an ethoxylated fatty alcohol ether, a sorbitan derivative and a fatty alcohol. Suitably, the mixture of an ethoxylated fatty alcohol ether, a sorbitan derivative and a fatty alcohol is a mixture of steareth-2, steareth-20, polysorbate 80 and cetearyl alcohol.

Antioxidant

The present topical pharmaceutical emulsion compositions comprise an antioxidant. In an embodiment, the antioxidant is a mixture of two or more antioxidants.

Exemplary antioxidants include, but are not limited to, butylated hydroxytoluene (BHT), butylated hydroxyanisole (BHA), tocopherol, propyl gallate, vitamin E TPGS and tert-Butylhydroquinone (TBHQ), and mixtures thereof. In an embodiment, the antioxidant is selected from the group consisting of butylated hydroxytoluene, propyl gallate and tocopherol, and mixtures thereof.

In one embodiment, the antioxidant is butylated hydroxytoluene. In another embodiment, the antioxidant is propyl gallate. In yet another embodiment, the antioxidant is a mixture of butylated hydroxytoluene and propyl gallate.

In an embodiment, the antioxidant is used in conjunction with a chelating agent to prevent or minimize metal-catalyzed reactions, such as reactions catalyzed by iron, nickel, copper, magnesium, calcium, zinc or aluminum ions.

Suitably, the antioxidant is present in the composition in an amount from about 0.001% to about 5% by weight, based on the total weight of the composition. In an embodiment, the antioxidant is present in an amount from about 0.01% to 1% by weight, such as about 0.05% by weight or about 0.1% by weight, based on the total weight of the composition.

Dermatologically Acceptable Excipients

The present topical pharmaceutical emulsion compositions may further comprise one or more additional dermatologically acceptable excipients. Exemplary additional dermatologically acceptable excipients include, but are not limited to, a pH adjusting agent, a chelating agent, a preservative, a co-solvent, a penetration enhancer, a humectant, a thickening or gelling or viscosity building agent, a fragrance, a colorant, and mixtures thereof.

In one embodiment, the additional dermatologically acceptable excipient is a preservative. In one embodiment, the additional dermatologically acceptable excipient is at least one co-solvent. In one embodiment, the additional dermatologically acceptable excipient is selected from the group consisting of a pH adjusting agent, a chelating agent, a preservative and a co-solvent, and mixtures thereof. In another embodiment, the additional dermatologically acceptable excipient comprises a mixture of a pH adjusting agent, a chelating agent, a preservative and a co-solvent.

In an embodiment, the emulsion is an oil-in-water emulsion. In another embodiment, the emulsion is a water-in-oil emulsion.

Suitably, the emulsion may be formulated as a cream. The cream may be an oil-in-water cream or a water-in-oil cream. In one particular embodiment, the cream is an oil-in-water cream.

In another embodiment, the emulsion may be formulated as a lotion. The lotion may be an oil-in-water lotion or a water-in-oil lotion.

pH Adjusting Agent

The present topical pharmaceutical emulsion compositions may further comprise a pH adjusting agent.

In an embodiment, the pH adjusting agent is an acid, an acid salt, or a mixture thereof. Suitably, the acid is selected from the group consisting of lactic acid, acetic acid, maleic acid, succinic acid, citric acid, benzoic acid, boric acid, sorbic acid, tartaric acid, edetic acid, phosphoric acid, nitric acid, sulphuric acid and hydrochloric acid, and mixtures thereof.

In another embodiment, the pH adjusting agent is a buffer. Suitably, the buffer is selected from the group consisting of citrate/citric acid, acetate/acetic acid, phosphate/phosphoric acid, propionate/propionic acid, lactate/lactic acid, ammonium/ammonia and edetate/edetic acid. In one embodiment, the pH adjusting agent is a buffer which is citrate/citric acid.

Suitably, the pH adjusting agent is present in the composition in an amount from about 0.01% to about 10% by weight, based on the total weight of the composition. In an embodiment, the pH of the composition is adjusted with a pH adjusting agent to a pH of from about 4 to about 7, such as from about 4.5 to about 6.5.

Chelating Agents

The present topical pharmaceutical emulsion compositions may further comprise a chelating agent. In an embodiment, the chelating agent is a mixture of two or more chelating agents. As described herein, the compositions of the invention may comprise a mixture of a chelating agent and an antioxidant, where both excipients act to prevent or minimize oxidative degradation reactions in the composition.

Exemplary chelating agents include, but are not limited to, citric acid, glucuronic acid, sodium hexametaphosphate, zinc hexametaphosphate, ethylene diamine tetraacetic acid (EDTA), phosphonates, salts thereof, and mixtures thereof. Ethylene diamine tetraacetic acid is also known as edetic acid.

In one embodiment, the chelating agent is EDTA or a salt thereof, such as potassium, sodium or calcium salts of EDTA. In an embodiment, the EDTA or a salt thereof is disodium EDTA. In another embodiment, the chelating agent is citric acid. In yet another embodiment, the compositions of the invention comprise a mixture of a chelating agent and an antioxidant which is a mixture of EDTA or a salt thereof and propyl gallate. In a further embodiment, the compositions of the invention comprise a mixture of a chelating agent and an antioxidant which is a mixture of EDTA or a salt thereof and BHT. In one embodiment, the compositions of the invention comprise a mixture of a chelating agent and an antioxidant which is a mixture of disodium EDTA and BHT.

In yet a further embodiment, the compositions comprise a mixture of a chelating agent and an antioxidant which is a mixture of citric acid and propyl gallate. In an embodiment, the compositions of the invention comprise a mixture of a chelating agent and an antioxidant which is a mixture of citric acid and BHT.

Suitably, the chelating agent is present in the composition in an amount from about 0.01% to about 1% by weight, based on the total weight of the composition. In one embodiment, the chelating agent is present in the composition in an amount of about 0.1% by weight, based on the total weight of the composition.

Preservatives

The present topical pharmaceutical emulsion compositions may further comprise a preservative. In an embodiment, the preservative is a mixture of two or more preservatives.

Exemplary preservatives include, but are not limited to, benzyl alcohol, imidazolidinyl urea, diazolidinyl urea, di chlorobenzyl alcohol, chloroxylenol, methyl paraben, ethyl paraben, propyl paraben, butyl paraben, phenoxyethanol, sorbic acid, benzoic acid, salts thereof, and mixtures thereof.

In an embodiment, the preservative is selected from the group consisting of benzyl alcohol, phenoxyethanol and benzoic acid, and mixtures thereof.

In one embodiment, the preservative is benzyl alcohol. In another embodiment, the preservative is phenoxyethanol. In yet another embodiment, the preservative is benzoic acid.

Suitably, the preservative is present in the composition in an amount from about 0.01% to about 2% by weight, based on the total weight of the composition. In one embodiment, the preservative is present in the composition in an amount of about 0.25% by weight, based on the total weight of the composition.

Co-Solvent

The topical pharmaceutical emulsion compositions may further comprise a co-solvent. The function of the co-solvent is to help solubilize the 3,5-Dihydroxy-4-isopropyl-trans-stilbene or a pharmaceutically acceptable salt thereof in the oil phase and/or the water phase of the emulsion composition, as desired. An oil miscible co-solvent may be used to help solubilize the active ingredient in oil phase, and a water miscible co-solvent may be used to help solubilize the active ingredient in the water phase. In one embodiment, the co-solvent is used to help solublize in the oil phase of the composition. In another embodiment, the co-solvent is used to help solublize the 3,5-Dihydroxy-4-isopropyl-trans-stilbene or a pharmaceutically acceptable salt thereof in the water phase of the composition.

In an embodiment, the co-solvent is a mixture of two or more co-solvents.

Exemplary co-solvents include, but are not limited to, alcohols such as ethanol, including absolute ethanol, isopropanol, t-butyl alcohol, amyl alcohol, benzyl alcohol, cyclohexanedimethanol, diacetone alcohol, hexyl alcohol, tetrahydrofurfuryl alcohol and diethylene glycol monoethyl ether (also referred to as ethoxy diglycol, and sold under the tradename Transcutol; carboxylic acids such as acetic acid or multi carboxylic acid; diols such as 1,2-hexanediol, butylene glycol, diethylene glycol, dipropylene glycol, ethyl hexanediol, ethylene glycol, hexylene glycol, pentylene glycol, propylene glycol, propylene glycol monolaurate, tetraethylene glycol, triethylene glycol, tripropylene glycol and polyethylene glycol; polyols such as butanetriol, glycerol and 1,2,6-hexanetriol; esters such as butyl stearate, C12-15 alkyl benzoate, C12-15 alkyl lactate, caprylic/capric triglyceride, cetearyl ethylhexanoate, cetearyl isononanoate, cetyl octanoate, cetyl palmitate, coco-caprylate/caprate, cocoglycerides, decyl oleate, dibutyl adipate, dicaprylyl carbonate, diethylhexyl adipate, di-ethylhexyl succinate, diisopropyl adipate, dioctyl malate, di-PPG-2 myreth-10 adipate, di-PPG-3 myristyl ether adipate, ethyl oleate, ethylhexyl cocoate, ethylhexyl hydroxystearate, ethylhexyl palmitate, ethylhexyl pelargonate, ethylhexyl stearate, hexyl laurate, hexyldecyl laurate, hexyldecyl stearate, isocetyl stearate, isocetyl stearoyl stearate, isodecyl oleate, isopropyl myristate, isopropyl palmitate, isostearyl neopentanoate, isotridecyl isononanoate, lauryl lactate, myristyl lactate, myristyl myristate, octyldodecyl stearoyl stearate, oleyl erucate, oleyl oleate, pentaerythrityl tetracaprylate/caprate, pentaerythrityl tetraisostearate, PPG-2 myristyl ether propionate, propylene glycol dicaprylate/dicaprate, propylene glycol isostearate, propyl heptyl caprylate, stearyl octanoate dimethyl isosorbide and propylene carbonate, macrogol-15-hydroxystearate, sold under the name "Solutol HS15" by BASF hydrogenated castor oil, PEG 40, sold under the name "Cremophor RH40" by BASF, PPG-15 stearyl ether, sold under the name "Arlamol E" by Uniquema, oleyl macrogol 6 glycerides, sold under the name "Labrafil M1944CS" by the Gattefosse, octyldodecanol, sold under the name "Eutanol G N-methyl-2-pyrrolidone, sold under the name "Pharmasolve", and mixtures thereof.

The one or more solvent or co-solvent agents are generally present in the composition sof the invention in an amount that is, firstly, sufficient to obtain the required solubility of the active ingredient to be formulated and, secondly, compatible with the need to preserve sustained chemical stability of this same active ingredient.

In one embodiment, the co-solvent is propylene glycol. In another embodiment, the co-solvent is a mixture of propylene glycol and diethylene glycol monoethyl ether.

In another embodiment, the co-solvent is PEG-400. In another embodiment, the co-solvent is a mixture of one or more of propylene glycol, transcutol, PEG 400, and glycerine.

While not definitive, in general water soluble co-solvents include, but are not limited to, alcohols such as ethanol, isopropanol, t-butyl alcohol, amyl alcohol, benzyl alcohol, cyclohexanedimethanol, diacetone alcohol, hexyl alcohol, tetrahydrofurfuryl alcohol and diethylene glycol monoethyl ether; carboxylic acids such as acetic acid or multi carboxylic acids; diols such as 1,2-hexanediol, butylene glycol, diethylene glycol, dipropylene glycol, ethyl hexanediol, ethylene glycol, hexylene glycol, pentylene glycol, propylene glycol, tetraethylene glycol, triethylene glycol, tripropylene glycol and polyethylene glycol; polyols such as butanetriol, glycerol, 1,2,6-hexanetriol, macrogol-15-hydroxystearate, sold under the name "Solutol HS15" by BASF, PEG 40, sold under the name "Cremophor RH40" by BASF, oleyl macrogol 6 glycerides, sold under the name "Labrafil M1944CS" by the Gattefosse, N-methyl-2-pyrrolidone, sold under the name "Pharmasolve", and combinations and mixtures thereof.

While not definitive, in general, oil soluble co-solvents include, but are not limited to propylene glycol monolaurate, esters such as butyl stearate, C12-15 alkyl benzoate, C12-15 alkyl lactate, caprylic/capric triglyceride, cetearyl ethylhexanoate, cetearyl isononanoate, cetyl octanoate, cetyl palmitate, coco-caprylate/caprate, cocoglycerides, decyl oleate, dibutyl adipate, dicaprylyl carbonate, diethylhexyl adipate, di-ethylhexyl succinate, diisopropyl adipate, dioctyl malate, di-PPG-2 myreth-10 adipate, di-PPG-3 myristyl ether adipate, ethyl oleate, ethylhexyl cocoate, ethylhexyl hydroxystearate, ethylhexyl palmitate, ethylhexyl pelargonate, ethylhexyl stearate, hexyl laurate, hexyldecyl laurate, hexyldecyl stearate, isocetyl stearate, isocetyl stearoyl stearate, isodecyl oleate, isopropyl myristate, isopropyl palmitate, isostearyl neopentanoate, isotridecyl isononanoate, lauryl lactate, myristyl lactate, myristyl myristate, octyldodecyl stearoyl stearate, oleyl erucate, oleyl oleate, pentaerythrityl tetracaprylate/caprate, pentaerythrityl tetraisostearate, PPG-2 myristyl ether propionate, propylene glycol dicaprylate/dicaprate, propylene glycol isostearate, propylheptyl caprylate, and stearyl octanoatedimethyl isosorbide, propylene carbonate, hydrogenated castor oil, PPG-15 stearyl ether, sold under the name "Arlamol E" by Uniquema, octyldodecanol, sold under the name "Eutanol G and combinations and mixtures thereof.

Suitably, the one or more co-solvent is present in the composition in an amount from about 1% to about 30% by weight, such as from about 5% to about 20% by weight, based on the total weight of the composition.

Penetration Enhancer

The present topical pharmaceutical emulsion compositions may further comprise a penetration enhancer. In an embodiment, the penetration enhancer is a mixture of two or more penetration enhancers. The co-solvent or mixture of two or more co-solvents described herein may function as a penetration enhancer.

Exemplary penetration enhancers include, but are not limited to, fatty acids, fatty acid esters, fatty alcohols, pyrrolidones, sulfoxides, alcohols, diols and polyols, and mixtures thereof.

Exemplary fatty acids include, but are not limited to, oleic acid, capric acid, hexanoic acid, lauric acid, linoleic acid, linolenic acid, propionic acid and vaccenic acid, and mixtures thereof.

Exemplary fatty acid esters include, but are not limited to, glycerol monolaurate, glycerol monooleate, glycerol monolinoleate, isopropyl isostearate, isopropyl palmitate, isopropyl myristate, diethylsebacate, sorbitan monopalmitate, sorbitan oleate, sorbitan dilaurate, sorbitan trioleate, propylene glycol monolaurate and sucrose monolaurate, and mixtures thereof.

Exemplary fatty alcohols include, but are not limited to, cetyl alcohol, stearyl alcohol, decanol, tridecanol, lauryl alcohol, linolenyl alcohol and oleyl alcohol, and mixtures thereof.

Exemplary pyrrolidones include, but are not limited to, N-methyl pyrrolidone, 2-pyrrolidone and N-cyclohexyl-2-pyrrolidone, and mixtures thereof.

Exemplary sulfoxides include, but are not limited to, dimethyl sulfoxide and decylmethyl sulfoxide, and mixtures thereof.

Exemplary alcohols include, but are not limited to, lower ($C_1$-$C_6$) alcohols and diethylene glycol monoethyl ether, and mixtures thereof.

Exemplary diols include, but are not limited to, 1,2-hexanediol, butylene glycol, diethylene glycol, dipropylene glycol, ethyl hexanediol, ethylene glycol, hexylene glycol, pentylene glycol, propylene glycol, propylene glycol monolaurate, tetraethylene glycol, triethylene glycol, tripropylene glycol, polyethylene glycol and polypropylene glycol, and mixtures thereof.

Exemplary polyols include, but are not limited to, butanetriol, glycerol and 1,2,6-hexanetriol, and mixtures thereof.

Suitably, the penetration enhancer is present in the composition in an amount from about 0.5% to about 40% by weight, such as from about 1% to about 20% by weight or from about 5% to about 15% by weight, based on the total weight of the composition.

Gelling Agent

The present topical pharmaceutical compositions may further comprise a gelling agent. In an embodiment, the gelling agent is a mixture of two or more gelling agents.

Exemplary gelling agents include, but are not limited to, agar, alginate, arabinoxylan, carrageenan, carboxymethylcellulose, hydroxyethyl cellulose, hydroxypropylcellulose, hydroxypropyl methylcellulose, cellulose, curdlan, gelatin, gellan, β-glucan, tragacanth gum, guar gum, gum arabic, locust bean gum, pectin, starch, a carbomer, acrylate copolymers, silica, xanthan gum, salts thereof, or a combination or mixture thereof.

Suitably, the gelling agent is present in the composition in an amount from about 0.1% to about 2% by weight, based on the total weight of the composition. In one embodiment, the gelling agent is present in the composition in an amount from about 0.2% to about 1% by weight, based on the total weight of the composition.

The 3,5-Dihydroxy-4-isopropyl-trans-stilbene or pharmaceutically acceptable salt thereof is applied to the patient for a dermatological disease or disorder in a dermatologically acceptable formulation. These formulations include any of the various known excipients which may be applied topically and which will permit even spreading of the active ingredient over the affected area, rapid drying, and/or increased penetration. Examples of suitable formulations will include solutions, milks, creams, ointments, gels, lotions, sprays, aerosols, foam, or suspensions.

Aqueous Solution

In one embodiment, the dermatologically acceptable formulation is an aqueous solution. In this embodiment, the pharmaceutical composition comprises water in an amount from about 50% to about 99.9% by weight, or from about 70% to about 99.9% by weight. Suitably, the pH of the composition is adjusted to a pH of between about 2 to about 6, but preferably to about 4 to about 6, such as about 4.5 to about 5.5. The topical aqueous solution may also comprise one or more of a co-solvent, a humectant, a chelating agent, an antioxidant, a preservative, a fragrance, a colorant or a penetration enhancer as described herein.

Aqueous Gel

In one embodiment, the dermatologically acceptable formulation is an aqueous gel. In this embodiment, the pharmaceutical composition comprises water in an amount from about 50% to about 99% by weight, such as from about 70% to about 99% by weight. Suitably, the pH of the composition is adjusted to a pH of between about 2 to about 6, but more particularly to about 4 to about 6, or about 4.5 to about 5.5. Furthermore, in this embodiment, the pharmaceutical composition will also comprise a suitable gelling agent. The composition may further comprise a co-solvent, a humectant, a chelating agent, an antioxidant, a preservative, a fragrance, a colorant or a penetration enhancer, or a combination or mixture thereof.

Hydroalcoholic Gel

In one embodiment, the dermatologically acceptable formulation is a hydroalcoholic gel. The hydroalcoholic solution of the invention may be thickened with a gelling agent to form a hydroalcoholic gel.

In one embodiment, the hydroalcoholic gel comprises water, a lower alcohol and a suitable gelling agent. The composition may further comprise one or more of a co-solvent, a pH adjusting agent, a humectant, a chelating agent, an antioxidant, a preservative, a fragrance, a colorant or a penetration enhancer.

Anhydrous Solution

In one embodiment, the dermatologically acceptable formulation is an anhydrous solution, that is, a solution that is substantially free or is free of water. In one embodiment, the anhydrous solution is free of water. In another embodiment, the anhydrous solution is substantially free of water.

In one embodiment, the anhydrous solution comprises an anhydrous vehicle. This is generally referred to as an aprotic or polar solvent.

In an embodiment, the anhydrous vehicle comprises one or more solvents. In another embodiment, the anhydrous vehicle is selected from one or more of a lower ($C_1$-$C_6$) alcohol, a diol and a polyol.

Suitably, the lower alcohol is selected from the group consisting of ethanol, propanol, isopropanol, n-butyl alcohol and t-butyl alcohol, and mixtures thereof. In one embodiment, the lower alcohol is ethanol. In another embodiment, the lower alcohol is a mixture of ethanol and one or more other lower alcohols.

Suitably, the diol is selected from the group consisting of 1,2-hexanediol, butylene glycol, diethylene glycol, dipropylene glycol, ethyl hexanediol, ethylene glycol, hexylene glycol, pentylene glycol, propylene glycol, propylene glycol monolaurate, tetraethylene glycol, triethylene glycol, tripropylene glycol and polyethylene glycol.

Suitably, the polyol is selected from the group consisting of butanetriol, glycerol and 1,2,6-hexanetriol.

In one embodiment, the anhydrous vehicle comprises a mixture of ethanol and propylene glycol. In another embodiment, the anhydrous vehicle comprises a mixture of ethanol, propylene glycol and polyethylene glycol. In yet another embodiment, the anhydrous vehicle is ethanol. The ethanol can optionally be an absolute ethanol.

Suitably, the anhydrous vehicle is present in the composition in an amount from about 50% to about 99.5% by weight.

The anhydrous solution may further comprise additional co-solvents, a humectant, a chelating agent, an antioxidant, a preservative, a fragrance, a colorant or a penetration enhancer, or a combination or mixture thereof.

Anhydrous Gel

In one embodiment, the dermatologically acceptable formulation is an anhydrous solution. The anhydrous solution may be thickened with a gelling agent to form an anhydrous gel. In one embodiment, the anhydrous gel comprises an anhydrous vehicle and a gelling agent. The anhydrous gel may further comprise a similar group of at least one dermatologically acceptable excipients, such as a co-solvent, a humectant, a chelating agent, an antioxidant, a preservative, a fragrance, a colorant or a penetration enhancer, or a combination or mixture thereof.

Oleaginous Solution

In one embodiment, the dermatologically acceptable formulation is formulated as oleaginous solutions. The oleaginous solutions are comprised of an oil and/or fat as described herein.

In one embodiment, the oil and/or fat is present in an amount from about 70% to about 99.9% by weight. In another embodiment, the oil and/or fat is present in an amount from about 80% to about 99% by weight.

The oleaginous solution may further comprise at least one dermatologically acceptable excipients such as a co-solvent, a humectant, a chelating agent, an antioxidant, a preservative, a fragrance, a colorant or a penetration enhancer, or a combination or mixture thereof.

Oleaginous Gel

In another embodiment, the oleaginous solutions are thickened with a gelling agent to form oleaginous gels.

In one embodiment, the oleaginous gel comprises an oil and/or fat and a gelling agent. Suitably, the oil and/or fat is present in an amount from about 70% to about 99.9% by weight, such as about 80% to about 99% by weight. The oleaginous gel may further comprise at least one dermatologically acceptable excipients such as a co-solvent, a humectant, a chelating agent, an antioxidant, a preservative, a fragrance, a colorant or a penetration enhancer, or a combination or mixture thereof.

Ointment

In one embodiment, the dermatologically acceptable formulation is an ointment. In one embodiment, it may be an oleaginous ointment, an emulsifiable ointment base, and emulsion ointment base and a water-soluble ointment base.

The ointments all comprise an oil and/or fat as described herein. Suitably, the oil and/or fat is present in an amount from about 80% to about 99.9% by weight, such as about 80% to about 99% by weight.

In one embodiment, the oleaginous ointment comprises predominantly petroleum jelly and/or liquid paraffin's, although other oil or fat constituents of the ointment may include oils of mineral, animal, vegetable or synthetic origin; thickeners such as waxes, of mineral, vegetable and animal origin; butters such as shea, cocoa, karite, or copra butter; lanolin and its derivatives, or mixtures thereof.

In one embodiment, the oleaginous ointment comprises petroleum jelly, a liquid fatty substance and a butter. Suitably the active ingredient is solubilized in one or more solvents or co-solvents, such as those described herein or solubilized in another oil component, such an ester of glycerin, e.g., a caprylic/capric triglyceride. Other solvents, co-solvents include PEG-400, the glycols, such as propylene glycol, and other such as diisopropyl adipate, isopropyl palmitate, isopropyl myristate, octyl dodecyl myristate and the medium-chain fatty acid triglycerides.

An absorbent ointment base denotes a water-absorbing or emulsifying property to the base. These bases are also referred to as emulsifiable ointment bases. They are generally anhydrous substances that have the property of absorbing (e.g. emulsifying) water but retaining their ointment like-consistency. They do not contain water as a component of their basic formulation but if it is incorporated a w/o emulsion will result. Anhydrous lanolin is one such product that falls under this definition as well as hydrophilic petrolatum.

Emulsion ointment bases are actually w/o and o/w type of products. They both permit the incorporation of some additional amounts of water without reducing the consistency of the base below that of a soft cream. A w/o emulsion can be diluted with oils.

Lastly, water soluble ointment bases are prepared from various higher ethylene glycol polymers (PEG). These polymers are marketed under the trademark of Carbowax. They have a wide range of molecular weight. Those at 200-700 are liquids, those about 1000 are wax-like solids. The polymers are waters-soluble, non-volatile. Use of mixtures of PEG's are often used.

Polyethylene glycols, polyoxyl 40 stearate, polysorbates and polyethylene glycol 400 monostearate are all useful components for this type of base. In one embodiment, the water-soluble ointment comprises a liquid fatty component, such as PEG 400.

The ointments may also comprise at least one dermatologically acceptable excipient such as a co-solvent, a humectant, a chelating agent, an antioxidant, a preservative, a fragrance, a colorant or a penetration enhancer, or a combination or mixture thereof.

In one embodiment, the ointments comprise petroleum jelly and a combination of additional oils and fats (also referred to as emollients) comprising at least one liquid fatty substance and at least one butter.

Liquid fatty components can be present in amounts ranging from about 0.01% to about 40% w/w, or from 0.01% to 15%, or from 0.01% to 10%, or from 0.01% to 5%. In one embodiment, the liquid fatty component is selected from a mineral oil, PEG 400, sunflower oil, almond oil, sesame oil, soya oil, or palm oil, or mixtures or combinations thereof.

Cream

In one embodiment, the dermatologically acceptable formulation is a cream. In one embodiment, the cream is an oil-in-water cream. Suitably, the oil-in-water cream comprises an oil phase, a water phase, a surfactant and an antioxidant.

In one embodiment, the pH of the composition is adjusted to a pH of between about 2 to about 6, such as about 4 to about 6. In another embodiment, the pH of the composition is adjusted to a pH of between about 4.5 to about 5.5.

The composition may further comprise a co-solvent, a humectant, a chelating agent, a preservative, a fragrance, a colorant or a penetration enhancer, or a combination or mixture thereof.

In one embodiment, the present invention provides a topical pharmaceutical emulsion composition comprising 3,5-Dihydroxy-4-isopropyl-trans-stilbene or a pharmaceutically acceptable salt thereof, an oil phase comprising an oil and/or fat in an amount from about 5% to about 45% by weight, a water phase comprising water in an amount from about 25% to about 85% by weight, a surfactant in an amount from about 1% to about 20% by weight, and an antioxidant in an amount from about 0.001% to about 5% by weight, wherein the emulsion composition is homogenous, and wherein all percentages are based on the percent by weight of the final composition, and all totals equal 100% by weight.

In one embodiment, the 3,5-Dihydroxy-4-isopropyl-trans-stilbene or pharmaceutically acceptable salt thereof is solubilized in the oil phase of the emulsion composition. In another embodiment, if the oil phase contains mineral oil or petrolatum, then a second oil phase component is present, and if the oil phase contains both mineral oil and petrolatum then a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum then at least a third oil phase component is present which is an ester and/or an ester of glycerin, suitably an ester of glycerin, such as a medium chain triglyceride.

In one embodiment, the present invention provides a topical pharmaceutical emulsion composition comprising 3,5-Dihydroxy-4-isopropyl-trans-stilbene or a pharmaceutically acceptable salt thereof, an oil phase comprising an oil and/or fat in an amount from about 5% to about 35% by weight, a water phase comprising water in an amount from about 25% to about 85% by weight, a surfactant in an amount from about 1% to about 20% by weight, and an antioxidant in an amount from amount from about 0.001% to about 5% by weight, wherein the emulsion composition is homogenous and the 3,5-Dihydroxy-4-isopropyl-trans-stilbene or pharmaceutically acceptable salt thereof is solubilized in the oil phase of the emulsion composition, and wherein all percentages are based on the percent by weight of the final composition, and all totals equal 100% by weight.

In another embodiment, the present invention provides a topical pharmaceutical emulsion composition comprising 3,5-Dihydroxy-4-isopropyl-trans-stilbene or a pharmaceutically acceptable salt thereof, an oil phase comprising an oil and/or fat in an amount from about 5% to about 35% by weight, a water phase comprising water in an amount from about 30% to about 80% by weight, a surfactant in an amount from about 5% to about 15% by weight, and an antioxidant in an from amount from about 0.001% to about 5% by weight, wherein the emulsion composition is homogenous, and wherein all percentages are based on the percent by weight of the final composition, and all totals equal 100% by weight. In another embodiment, the 3,5-Dihydroxy-4-isopropyl-trans-stilbene or pharmaceutically acceptable salt thereof is solubilized in the oil phase of the emulsion composition.

In one embodiment, the composition may further comprise one or more co-solvents in the composition present in an amount from about 1% to about 30% by weight, based on the total weight of the composition. In another embodiment, the composition may comprise a preservative present in an amount from about 0.01% to about 2% by weight, based on the total weight of the composition. In another embodiment, the composition may further comprise a chelating agent present in an amount from about 0.01% to about 1% by weight, based on the total weight of the composition. In another embodiment, the composition may further comprise a pH adjusting agent present in an amount from about 0.01% to about 10% by weight, based on the total weight of the composition. In another embodiment, the oil phase comprises an ester and/or an ester of glycerin, suitably an ester of glycerin which is a medium chain triglycerides (MCT) present in an amount from about 2% to about 30% by weight, based on the total weight of the composition.

In another embodiment the present invention provides a topical pharmaceutical emulsion composition comprising 3,5-Dihydroxy-4-isopropyl-trans-stilbene or a pharmaceutically acceptable salt thereof, an oil phase comprising an oil and/or fat in an amount from about 5% to about 35% by weight, a water phase comprising water in an amount from about 30% to about 80% by weight, a surfactant in an amount from about 5% to about 15% by weight, an antioxidant in an amount from amount from about 0.001% to about 5% by weight, a pH adjusting agent in an amount from about 0.01% to about 10% by weight, wherein the emulsion composition is homogenous, and wherein all percentages are based on the percent by weight of the final composition, and all totals equal 100% by weight. In another embodiment, the water is present in an amount from about 55% to about 75% by weight, based on the total weight of the composition. In another embodiment, the oil and/or fat is present in an amount from about 5% to about 25% by weight, based on the total weight of the composition. In another embodiment, the oil and/or fat is present in an amount from about 5% to about 15% by weight, based on the total weight of the composition. In one embodiment, the 3,5-Dihydroxy-4-isopropyl-trans-stilbene or pharmaceutically acceptable salt thereof is solubilized in the oil phase of the emulsion composition. In one embodiment, the composition may further comprise one or more co-solvents in the composition present in an amount from about 1% to about 30% by weight, based on the total weight of the composition.

The present invention also provides for a pharmaceutical product comprising a combination of therapeutic agents, for simultaneous, separate or sequential use in the treatment of conditions for which administration of 3,5-Dihydroxy-4-isopropyl-trans-stilbene or a pharmaceutically acceptable salt thereof is indicated.

In the context of this specification, the term "simultaneously" when referring to simultaneous administration of the relevant drugs means at exactly the same time, as would be the case, for example in embodiments where the drugs are combined in a single preparation. In other embodiments, "simultaneously" can mean one drug is administered a short duration after another, wherein "a short duration" means a duration which allows the drugs to have their intended synergistic effect.

In light of the foregoing, the present invention also relates to combination therapy, which may be a comprised of a simultaneous or co-administration, or serial administration of a combination of compounds or pharmaceutical compositions of the present invention with other active drug or therapeutic agents, and where such administration also is determined by one of ordinary skill in the art.

In such an aforementioned combination composition, the dosage form of the present invention, each of the active drug components are contained in effective dosage amounts.

In another aspect, the present invention relates to a combination therapy, where the second therapeutic agent may be administered before, concurrent with or after administration of the 3,5-Dihydroxy-4-isopropyl-trans-stilbene or a pharmaceutically acceptable salt thereof whether in the same formulation or in a separate formulation and whether or not the second therapeutic agent is administered by the same topical route, e.g. it may be given orally, intravenously, intramuscularly, opthalmically, vaginally, rectally, etc.

In other words, the 3,5-Dihydroxy-4-isopropyl-trans-stilbene or a pharmaceutically acceptable salt thereof may be administered together, contemporaneously or sequentially in either order to the site of administration, or to a desired site of action. The order of administration is not deemed necessary, provided that if topically administered they are in contact at some point together at the site of administration or desired site of action. If both are present in the same vehicle they provide ease of administration to the patient, and perhaps increased compliance, but it is not required for the invention herein.

In another embodiment, the topical pharmaceutical compositions have greater than 90% of the original concentration of 3,5-Dihydroxy-4-isopropyl-trans-stilbene or a pharmaceutically acceptable salt thereof remaining after storage of the composition for 3 months at 40° C.

In one embodiment, the present invention provides a topical pharmaceutical emulsion composition comprising 3,5-Dihydroxy-4-isopropyl-trans-stilbene or a pharmaceutically acceptable salt thereof, an oil phase, a water phase, a surfactant, and an antioxidant, and wherein the emulsion is homogenous. In another embodiment, the 3,5-Dihydroxy-4-isopropyl-trans-stilbene or pharmaceutically acceptable salt thereof is solubilized in the oil phase of the emulsion composition. In another embodiment, the composition is an oil-in-water cream.

In one embodiment, the present invention provides a topical pharmaceutical emulsion composition comprising 3,5-Dihydroxy-4-isopropyl-trans-stilbene or a pharmaceutically acceptable salt thereof, an oil phase, a water phase, a surfactant, an antioxidant and a preservative, and wherein the emulsion composition is homogenous. In another embodiment, the 3,5-Dihydroxy-4-isopropyl-trans-stilbene or pharmaceutically acceptable salt thereof is solubilized in the oil phase of the emulsion composition. In another embodiment, the composition is an oil-in-water cream.

In one embodiment, the present invention provides a topical pharmaceutical emulsion composition comprising 3,5-Dihydroxy-4-isopropyl-trans-stilbene or a pharmaceutically acceptable salt thereof, an oil phase, a water phase, a surfactant, an antioxidant, a preservative and a co-solvent, and wherein the emulsion composition is homogenous. In another embodiment, the 3,5-Dihydroxy-4-isopropyl-trans-stilbene or pharmaceutically acceptable salt thereof is solubilized in the oil phase of the emulsion composition. In another embodiment, the composition is an oil-in-water cream.

In one embodiment, the present invention provides a topical pharmaceutical emulsion composition comprising 3,5-Dihydroxy-4-isopropyl-trans-stilbene or a pharmaceutically acceptable salt thereof, an oil phase, a water phase, a surfactant, an antioxidant, a preservative, a co-solvent and a pH adjusting agent, and wherein the emulsion is homogenous. In another embodiment, the 3,5-Dihydroxy-4-isopropyl-trans-stilbene or pharmaceutically acceptable salt thereof is solubilized in the oil phase of the emulsion composition. In another embodiment, the composition is an oil-in-water cream.

In another embodiment, the present invention provides a topical pharmaceutical emulsion composition comprising:
i) 3,5-Dihydroxy-4-isopropyl-trans-stilbene or a pharmaceutically acceptable salt thereof;
i) an oil phase comprising an oil and/or fat;
iii) a water phase, comprising water;
iv) a surfactant;
v) an antioxidant;
vi) a pH adjusting agent;
vii) a chelating agent;
viii) a preservative; and
ix) a co-solvent, and wherein the emulsion is homogenous.

Suitably, the 3,5-Dihydroxy-4-isopropyl-trans-stilbene or a pharmaceutically acceptable salt thereof is solubilized in the oil phase of the emulsion composition, and suitably the composition is an oil-in-water cream.

In one embodiment, if the oil phase contains mineral oil or petrolatum, then a second oil phase component is present, and if the oil phase contains both mineral oil and petrolatum than a third oil phase component is also present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum than at least a third oil phase component is present which is an ester and/or an ester of glycerin, suitably an ester of glycerin such as as medium chain triglyceride. In another embodiment, if the oil phase comprises mineral oil then a second oil phase component is present which is an ester and/or an ester of glycerin, suitably an ester of glycerin, such as a medium chain triglyceride.

In another embodiment, the present invention provides a topical pharmaceutical emulsion composition comprising:
3,5-Dihydroxy-4-isopropyl-trans-stilbene or a pharmaceutically acceptable salt thereof,
an oil phase comprising an oil and/or fat,
a water phase comprising water,
a surfactant comprising an ethoxylated fatty alcohol ether; and wherein the emulsion is homogenous.

In another embodiment, the present invention provides a topical pharmaceutical emulsion composition comprising:
3,5-Dihydroxy-4-isopropyl-trans-stilbene or a pharmaceutically acceptable salt thereof,
an oil phase comprising an oil and/or fat,
a water phase comprising water,
a surfactant comprising an ethoxylated fatty alcohol ether,
an antioxidant selected from the group consisting of butylated hydroxytoluene, propyl gallate and tocopherol, and mixtures thereof; and wherein the emulsion is homogenous.

In another embodiment, the present invention provides a topical pharmaceutical emulsion composition comprising:
3,5-Dihydroxy-4-isopropyl-trans-stilbene or a pharmaceutically acceptable salt thereof,
an oil phase comprising an oil and/or fat,
a water phase comprising water,
a surfactant comprising an ethoxylated fatty alcohol ether,
an antioxidant selected from the group consisting of butylated hydroxytoluene, propyl gallate and tocopherol, and mixtures thereof, and
a chelating agent, and wherein the emulsion is homogenous.

In another embodiment, the present invention provides a topical pharmaceutical emulsion composition comprising:
i) 3,5-Dihydroxy-4-isopropyl-trans-stilbene or a pharmaceutically acceptable salt thereof,
ii) an oil phase comprising an oil and/or fat,
iii) a water phase comprising water,
iv) a surfactant comprising an ethoxylated fatty alcohol ether,
v) an antioxidant selected from the group consisting of butylated hydroxytoluene, propyl gallate and tocopherol, and mixtures thereof,
vi) a chelating agent,
vii) a preservative selected from the group consisting of benzyl alcohol, phenoxyethanol and benzoic acid, and mixtures thereof, and wherein the emulsion is homogenous.

In another embodiment, the present invention provides a topical pharmaceutical emulsion composition comprising:
i) 3,5-Dihydroxy-4-isopropyl-trans-stilbene or a pharmaceutically acceptable salt thereof,
ii) an oil phase comprising an oil and/or fat,
iii) a water phase comprising water,
iv) a surfactant comprising an ethoxylated fatty alcohol ether,
v) an antioxidant selected from the group consisting of butylated hydroxytoluene, propyl gallate and tocopherol, and mixtures thereof,
vi) a chelating agent,
vii) a preservative selected from the group consisting of benzyl alcohol, phenoxyethanol and benzoic acid, and mixtures thereof, viii) a co-solvent, and
ix) a pH adjusting agent, and wherein the emulsion is homogenous.

Suitably, the 3,5-Dihydroxy-4-isopropyl-trans-stilbene or pharmaceutically acceptable salt thereof is solubilized in the oil phase of the emulsion composition. Suitably, the composition is an oil-in-water cream. In one embodiment, if the oil phase comprises mineral oil or petrolatum, then a second oil phase component is present, and if the oil phase contains both mineral oil and petrolatum then a third oil phase component is present. In one embodiment, the oil phase is substantially free from petrolatum. In another embodiment, the oil phase contains ≤3%, or ≤2%, or ≤1% petrolatum. In another embodiment, if the oil phase contains both mineral oil and petrolatum at least a third oil phase component is present which is an ester and/or an ester of glycerin, suitably an ester of glycerin such as a medium chain triglyceride. In another embodiment, if the oil phase contains mineral oil then a second oil phase component is present which is an ester and/or an ester of glycerin, suitably an ester of glycerin such as a medium chain triglyceride.

In another embodiment, the present invention provides a topical pharmaceutical emulsion composition comprising:
3,5-Dihydroxy-4-isopropyl-trans-stilbene or a pharmaceutically acceptable salt thereof,
an oil phase comprising an oil and/or fat which is medium chained triglycerides,
a water phase comprising water,
a surfactant comprising an ethoxylated fatty alcohol ether,
an antioxidant which is butylated hydroxytoluene,
a chelating agent which is EDTA or a salt thereof,
a preservative which is benzoic acid,
a co-solvent comprising a mixture of propylene glycol and diethylene glycol monoethyl ether, and
a pH adjusting agent which is a citrate/citric acid buffer, and wherein the pH of the composition is adjusted to a pH of from about 4.5 to about 6.5, and wherein the emulsion is homogenous.

Suitably, the 3,5-Dihydroxy-4-isopropyl-trans-stilbene or pharmaceutically acceptable salt thereof is solubilized in the oil phase of the emulsion composition. Suitably, the composition is an oil-in-water cream.

In all of the compositions described herein, the amount of 3,5-Dihydroxy-4-isopropyl-trans-stilbene or a pharmaceutically acceptable salt thereof which may be present in a composition may range from about 0.25% to about 2% by weight of composition. In one embodiment, the amount may be 0.25%, 0.3%, 0.4%, 0.5%, 0.75%, 1.0%, 1.25%, 1.5%, 1.75% or 2.0% by weight, based on the total weight of the composition. In another embodiment, the amount is about 0.25% to about 0.50% by weight, based on the total weight of the composition. In another embodiment, the amount is about 0.25% by weight, based on the total weight of the composition. In another embodiment, the amount is about 0.50% by weight, based on the total weight of the composition. In another embodiment, the amount is about 0.75% by weight, based on the total weight of the composition. In another embodiment, the amount is about 1.0% by weight, based on the total weight of the composition.

In yet another embodiment of the invention there is a topical pharmaceutical emulsion composition comprising (a) an oil phase; (b) an aqueous/water phase; (c) at least one co-solvents; (d) at least one surfactant; (e) an antioxidant, and (f) the active ingredient 3,5-Dihydroxy-4-isopropyl-trans-stilbene or a pharmaceutically acceptable salt thereof. In one embodiment, the oil phase contains mineral oil. In another the oil phase contains petrolatum. In another embodiment, the oil phase contains both mineral oil and petrolatum. In another embodiment, the oil phase contains mineral oil and/or petrolatum each independently present in amounts greater than 3% w/w. In another embodiment, the oil phase contains mineral oil and/or petrolatum each independently present in amounts greater than 5% w/w. In another embodiment, the oil phase contains mineral oil and/or petrolatum each independently present in amounts greater than 10% w/w. In another embodiment, the oil phase contains mineral oil and/or petrolatum each independently present in amounts greater than 15% w/w. In another embodiment, the oil phase contains mineral oil and/or petrolatum present in amounts greater than 5% w/w in any combination. In another embodiment, the oil phase contains mineral oil and/or petrolatum present in amounts greater than 10% w/w in any combination. In another embodiment, the oil phase contains mineral oil and/or petrolatum present in amounts greater than 15% w/w in any combination. In another embodiment, the oil phase contains mineral oil and/or petrolatum present in amounts greater than 20% w/w in any combination. In another embodiment, the oil phase contains mineral oil and/or petrolatum present in amounts greater than 25% w/w in any combination.

While not wishing to be limited to this explanation it is believed that when the oil phase contains components that the active ingredient is not soluble in, such as mineral oil and/or petrolatum as exemplified herein by Formulations 1, 12 and 41-42 the active ingredient is solubilized in the co-solvents, such as but not limited to propylene glycol and/or diethylene glycol monoethyl ether. Subsequently, when the aqueous phase is added to the oil phase, the active ingredient might be soluble in both the aqueous and/or the oil phase depending on where and how much of the co-solvent(s) partition into the system.

In another embodiment, the present invention provides a topical pharmaceutical emulsion composition comprising:
i) 3,5-Dihydroxy-4-isopropyl-trans-stilbene or a pharmaceutically acceptable salt thereof;
ii) an oil phase comprising at least one oil and/or fat which is mineral oil or petrolatum;
iii) an aqueous phase comprising water;
iv) at least one co-solvent; and
v) a surfactant, and optionally, in this embodiment, the pharmaceutical composition may also comprise a suitable gelling agent, a humectant, a pH adjusting agent, a chelating agent, a preservative, a fragrance, a colorant or a penetration enhancer, or a combination or mixture thereof; and wherein all percentages are based on the percent by weight of the final composition, and all totals equal 100% by weight.

Suitably the composition is an oil-in-water cream. In one embodiment, the surfactant comprises an ethoxylated fatty alcohol ether. In another embodiment, the co-solvent comprises a mixture of propylene glycol and diethylene glycol monoethyl ether.

In another embodiment, the present invention provides a topical pharmaceutical emulsion composition comprising:
i) 3,5-Dihydroxy-4-isopropyl-trans-stilbene or a pharmaceutically acceptable salt thereof;
ii) an oil phase comprising at least one oil and/or fat which is mineral oil or petrolatum in an amount from about 5% to about 45% by weight,
iii) an aqueous phase comprising water in an amount from about 50% to about 99.9% by weight,
iv) at least one co-solvent in an amount from about 1% to about 30% by weight;

v) a surfactant in an amount from about 1% to about 20% by weight;

vi) an antioxidant in an amount from amount from about 0.001% to about 5% by weight, and optionally, a gelling agent, a humectant, a pH adjusting agent, a chelating agent, a preservative, a fragrance, a colorant or a penetration enhancer, or a combination or mixture thereof; and wherein all percentages are based on the percent by weight of the final composition, and all totals equal 100% by weight In one embodiment, the surfactant comprises an ethoxylated fatty alcohol ether. In another embodiment, the co-solvent comprises a mixture of propylene glycol and diethylene glycol monoethyl ether.

In another embodiment, the antioxidant is selected from the group consisting of butylated hydroxytoluene, propyl gallate and tocopherol, and mixtures thereof.

In another embodiment, the co-solvent comprises a mixture of propylene glycol and diethylene glycol monoethyl ether.

In another embodiment, the present invention provides a topical pharmaceutical emulsion composition comprising:
  i) 3,5-Dihydroxy-4-isopropyl-trans-stilbene or a pharmaceutically acceptable salt thereof;
  ii) an oil phase comprising at least one oil and/or fat which is mineral oil or petrolatum;
  iii) an aqueous phase comprising water;
  iv) at least one co-solvent;
  v) a surfactant;
  vi) an antioxidant; and
  vii) a chelating agent, and optionally, a gelling agent, a humectant, a pH adjusting agent, a preservative, a fragrance, a colorant or a penetration enhancer, or a combination or mixture thereof, and wherein all percentages are based on the percent by weight of the final composition, and all totals equal 100% by weight.

In another embodiment, the co-solvent comprises a mixture of propylene glycol and diethylene glycol monoethyl ether.

In one embodiment, the surfactant comprises an ethoxylated fatty alcohol ether.

In another embodiment, the antioxidant is selected from the group consisting of butylated hydroxytoluene, propyl gallate and tocopherol, and mixtures thereof.

In another embodiment, the composition may further comprise a chelating agent present in an amount from about 0.01% to about 1% by weight, based on the total weight of the composition. In an embodiment, the chelating agent is a mixture of two or more chelating agents.

In another embodiment, the present invention provides a topical pharmaceutical emulsion composition comprising:
  i) 3,5-Dihydroxy-4-isopropyl-trans-stilbene or a pharmaceutically acceptable salt thereof,
  ii) an oil phase comprising at least one oil and/or fat which is mineral oil or petrolatum;
  iii) an aqueous phase comprising water;
  iv) at least one co-solvent;
  v) a surfactant;
  vi) an antioxidant,
  vii) a chelating agent, and
  viii) a preservative, and optionally, a gelling agent, a humectant, a pH adjusting agent, a preservative, a fragrance, a colorant or a penetration enhancer, or a combination or mixture thereof; and wherein all percentages are based on the percent by weight of the final composition, and all totals equal 100% by weight.

In one embodiment, the surfactant comprises an ethoxylated fatty alcohol ether. In another embodiment, there are 2 surfactants present in the formulation. Suitably, when there are 2 surfactants present, each surfactant is present in an amount from about 0.5% to about 5% by weight, based on the total weight of the composition. In another embodiment, there are 3 surfactants present in the formulation. Suitably, when there are 3 surfactants present, each surfactant is present in an amount from about 0.5% to about 5% by weight, based on the total weight of the composition. Similarly, if there are 4 or more surfactants present they are each present in an amount from about 0.5% to about 5% by weight, based on the total weight of the composition.

In another embodiment, the antioxidant is selected from the group consisting of butylated hydroxytoluene, propyl gallate and tocopherol, and mixtures thereof.

In another embodiment, the co-solvent comprises a mixture of propylene glycol and diethylene glycol monoethyl ether.

In one embodiment, the chelating agent is EDTA or a salt thereof.

In another embodiment, the preservative is benzoic acid.

In another embodiment, the present invention provides a topical pharmaceutical emulsion composition comprising:
  i) 3,5-Dihydroxy-4-isopropyl-trans-stilbene or a pharmaceutically acceptable salt thereof,
  ii) an oil phase comprising at least one oil and/or fat which is mineral oil or petrolatum,
  iii) a water phase comprising water,
  iv) a surfactant comprising an ethoxylated fatty alcohol ether,
  v) an antioxidant,
  vi) a chelating agent,
  vii) a preservative,
  viii) a co-solvent, and
  ix) a pH adjusting agent, and optionally, a gelling agent, a humectant, a preservative, a fragrance, a colorant or a penetration enhancer, or a combination or mixture thereof; and wherein all percentages are based on the percent by weight of the final composition, and all totals equal 100% by weight.

In one embodiment, the surfactant comprises an ethoxylated fatty alcohol ether.

In another embodiment, the antioxidant is selected from the group consisting of butylated hydroxytoluene, propyl gallate and tocopherol, and mixtures thereof.

In another embodiment, the preservative selected from the group consisting of benzyl alcohol, phenoxyethanol and benzoic acid, and mixtures thereof, In another embodiment, the co-solvent comprises a mixture of propylene glycol and diethylene glycol monoethyl ether.

In one embodiment, the chelating agent is EDTA or a salt thereof.

In another embodiment, the preservative is benzoic acid,

In another embodiment, the pH adjusting agent is a citrate/citric acid buffer.

Alternatively, when discussed in a biological function, the term applied dose may be used. As used herein, applied dose is defined as the amount of drug product applied per body surface area, denoted in mg/cm' units. The amount of active ingredient delivered to the skin layers (epidermis or dermis) may be denoted in nanograms (ng) or micrograms (μg) per skin section or per cm'. Alternatively, the amount of active ingredient delivered to epidermis or dermis may be denoted as % of the applied dose. The amount of active ingredient delivered to the receiving fluid may be denoted as cumulative amount in ng or ng/cm$^2$.

In an embodiment, the emulsion composition comprises 3,5-Dihydroxy-4-isopropyl-trans-stilbene or a pharmaceutically acceptable salt thereof in a composition that has a human skin penetration measured in vitro of at least 0.01-10% of the applied dose of the active ingredient into the epidermis over a period of about 1 to about 72 hours. In another embodiment, the time period is from about 2 to about 24 hours. In another embodiment, the time period is about 1 to about 15 hours. The % of applied dose of the active ingredient may be from 0.01-10%, 0.01-5%, 0.01-3%, 0.4-2.3% w/w.

In one embodiment, the emulsion composition comprises the 3,5-Dihydroxy-4-isopropyl-trans-stilbene or a pharmaceutically acceptable salt thereof in a composition that has human skin penetration measured in vitro of at least 0.01-10% of the applied dose of the active ingredient into the dermis over a period of about 1 to about 72 hours. In another embodiment, the time period is from about 2 to about 24 hours. In another embodiment, the time period is about 6 to about 15 hours. The % of applied dose of the active ingredient may be from 0.01-7.5%, 0.01-5%, 0.01-3%, 0.3-1.7%. In an alternative embodiment, the applied dose measured in an amount of 1-2 µg/cm$^2$, e.g. 0.5% w/v.

Figure 4:
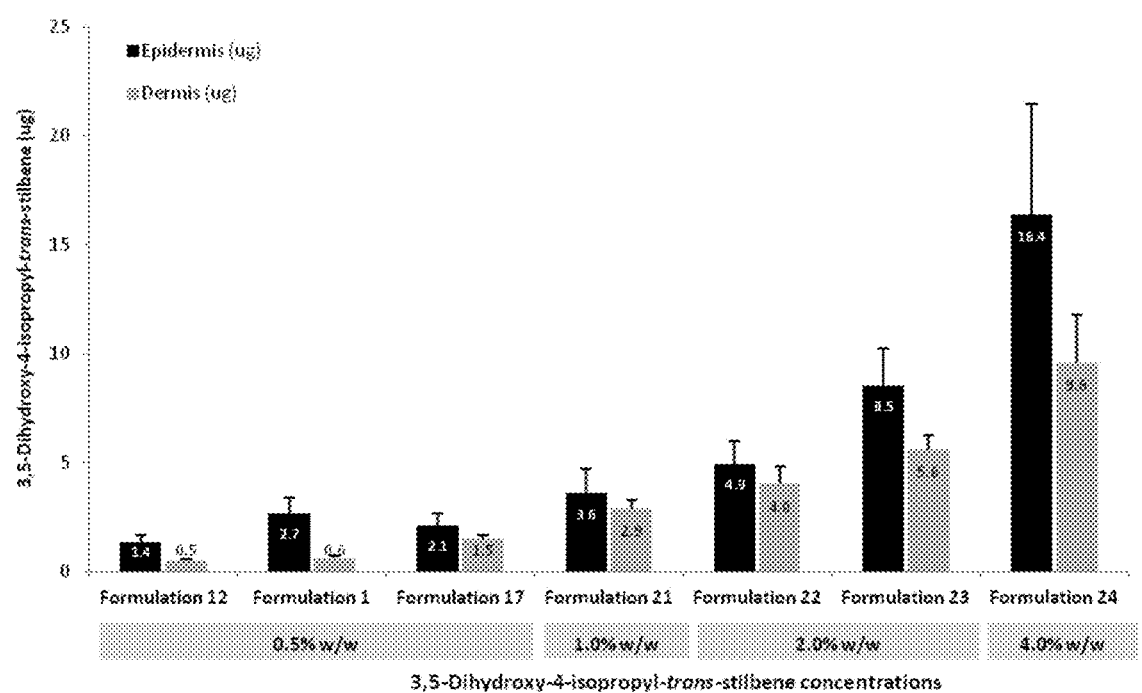
FIG. 4 illustrates the amount of 3,5-Dihydroxy-4-isopropyl-trans-stilbene delivered into the epidermis and dermis from Formulations 1, 12, 17 and 21-24.
Figure 5:
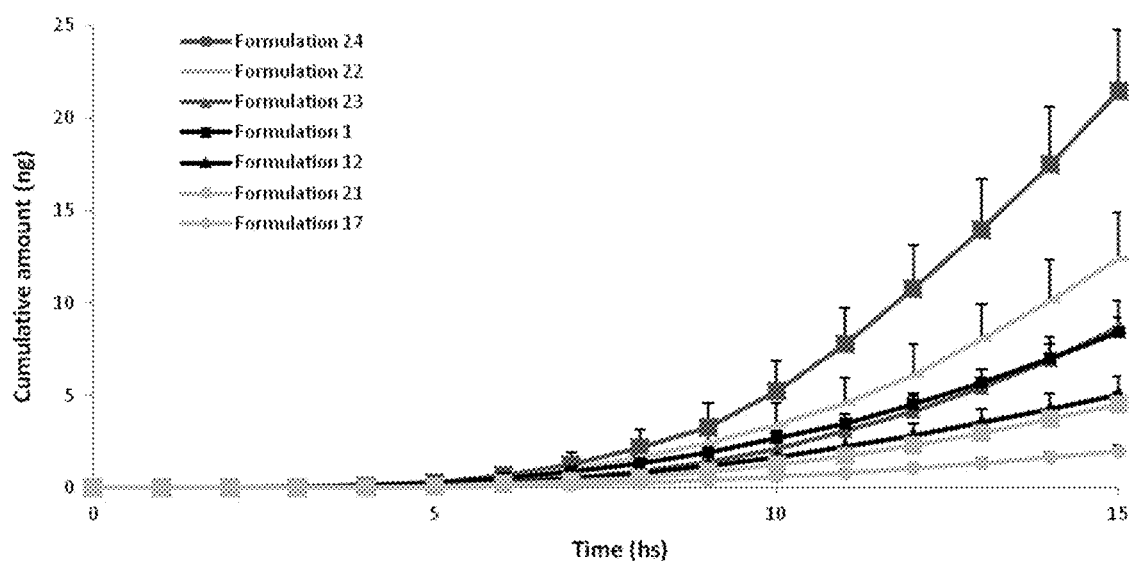
FIG. 5 illustrates the amount of 3,5-Dihydroxy-4-isopropyl-trans-stilbene delivered into the receiving fluid over 15 hours from Formulations 1, 12, 17, and 21-24.

As illustrated in FIG. 4, Formulation 17 delivers a higher relative amount of the active ingredient into the dermis compared with Formulations 1 and 12. Conversely, Formulation 17 delivered comparatively less into the receiving fluid, as illustrated in FIG. 5. Formulations 1 and 12 were very comparable, with minor changes in buffer composition and preservative (Tables 1 and 4, respectively). The in vitro human skin flux and dermal deposition results confirmed such similarities and enabled the extrapolation of further data comparison of any other formulation with Formulation 12 and, therefore with Formulation 1.

Figure 6:
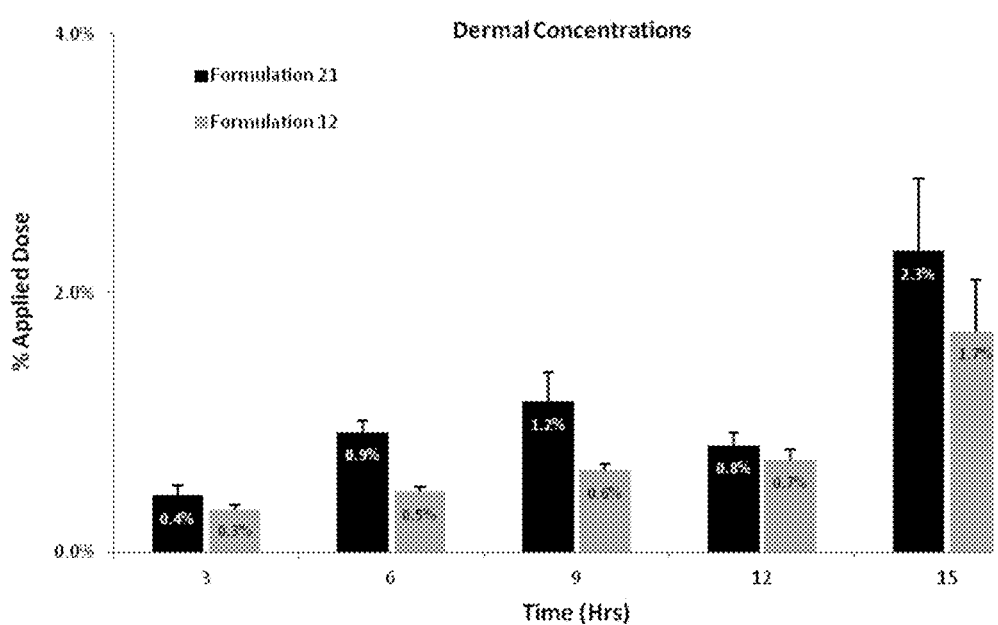
FIG. 6 illustrates the amount of 3,5-Dihydroxy-4-isopropyl-trans-stilbene delivered into the dermis at 3, 6, 9, 12 and 15 hours from Formulations 12 and 21.
Figure 7:
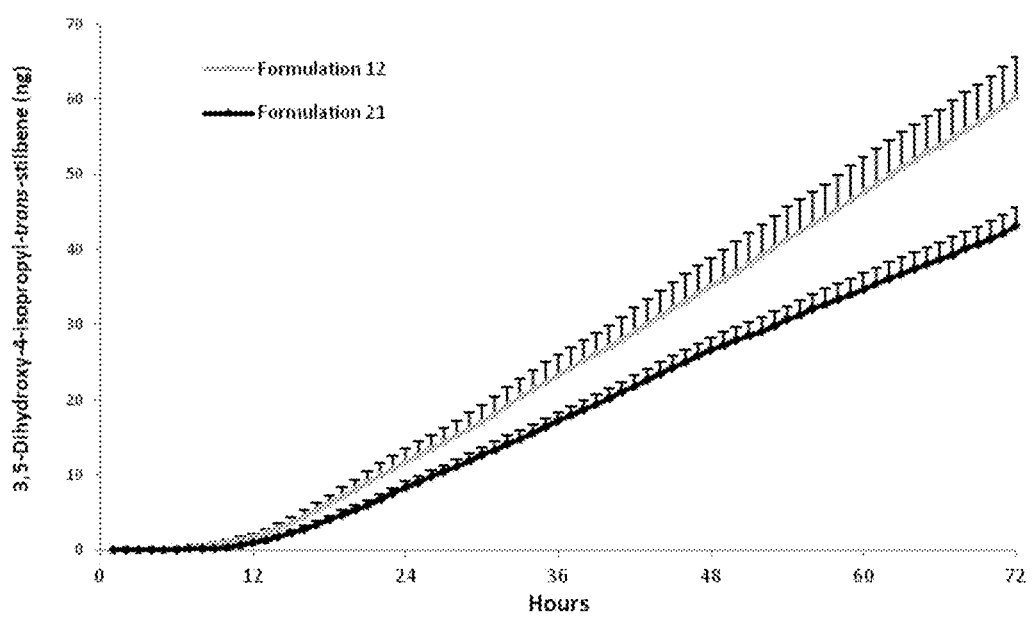
FIG. 7 illustrates the amount of 3,5-Dihydroxy-4-isopropyl-trans-stilbene delivered into the receiving fluid over 72 hours from Formulations 12 and 21.
Figure 8:
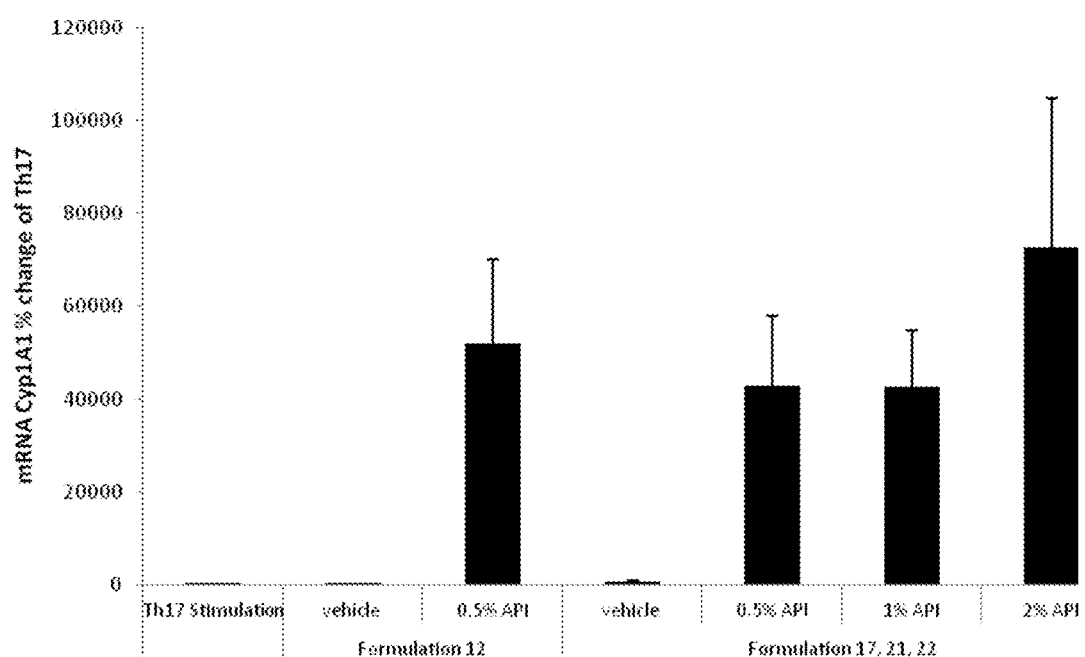
FIG. 8 illustrates the percent change of mRNA Cyp1A1 in human ex vivo skin after Th17 stimulation from Formulations 12, 17, 21 and 22.
Figure 9:
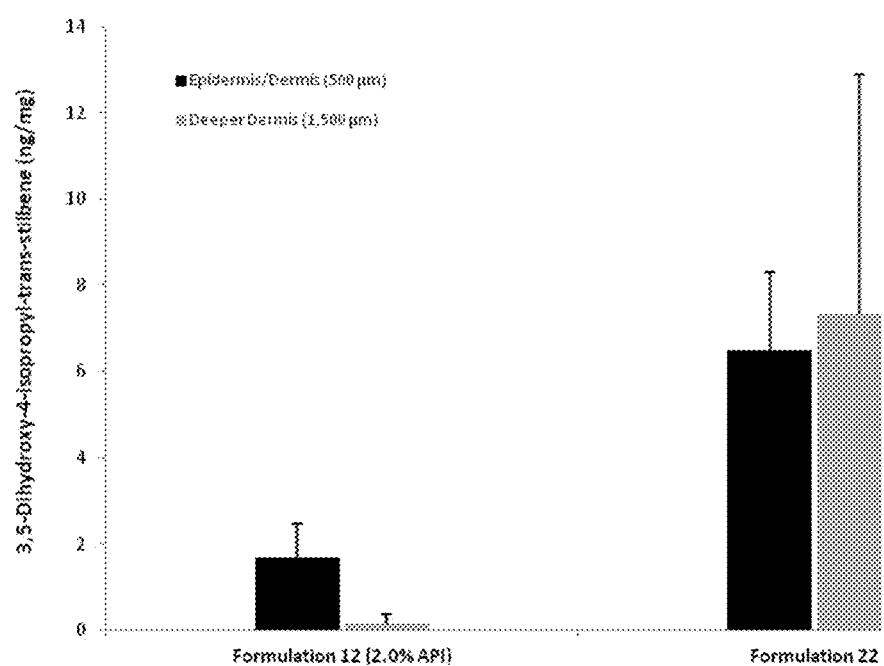
FIG. 9 illustrates the amount of 3,5-Dihydroxy-4-isopropyl-trans-stilbene delivered into skin of Gottingen minipigs after 7 days of repeat dosing.
Figure 10:
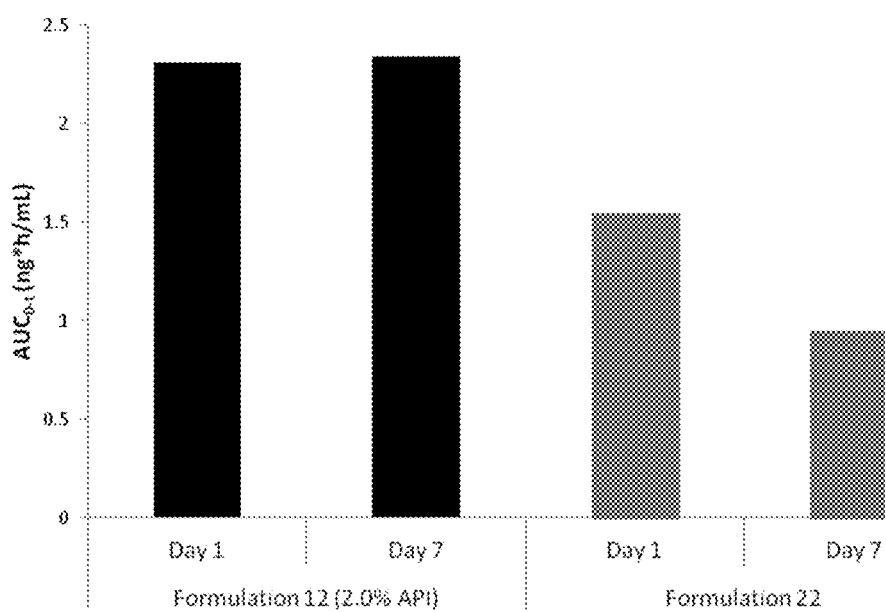
FIG. 10 illustrates the amount of 3,5-Dihydroxy-4-isopropyl-trans-stilbene in the plasma of Gottingen minipigs after 7 days of repeat dosing. As noted herein, "Formulation 12 (2.0%)" as used throughout, including FIGS. 9 and 10 corresponds to Formulation 14.

Although the two formulations shown in FIGS. 6 and 7 have differing amounts of active ingredient (Formulation 12 is 0.5% and Formulation 21 is 1%), the same conclusions can be reached when normalization is applied, e.g. Formulation 21 also shows a higher relative amount in the dermis as compared to the receiving fluid, which is measured as skin flux values and cumulative amounts, as normalized for applied dose. The cumulative amount represents how much active ingredient penetrates through the skin (500+100 µm), reaching the receiving fluid, over a specific period of time. The skin flux represents the slope of the cumulative amount curve, characterized as a linear phase and also referred as steady state ($R^2 \geq 0.99$), observed during the course of the experiment.

By converting the dermis amount from each time point (FIG. 6) from % of applied dose to ng of the active ingredient and dividing this value by the respective cumulative amount in ng (FIG. 7) at 3, 6, 9, 12 and 15 hours, it was demonstrated that Formulation 21 promoted a targeted delivery to the dermis, resulting in less active ingredient penetrating the receiving fluid (unbound active ingredient penetrating deeper than 500±100 µm). The ratios dermis/cumulative amount in the receiving fluid (ng/ng) for Formulation 21 ranged from 9038.0 and 12937 at 3 hours and 6 hours, respectively, to 909.3 and 1044.0 at 12 hours and 15 hours, respectively. Formulation 12 showed a significantly different profile, with its ratios ranging from 7870.2 and 1428.7 at 3 hours and 6 hours, respectively, to 215.7 and 233.93 at 12 hours and 15 hours, respectively. Since Formulation 21 showed good dose proportionality at different active ingredient strengths ranging from 0.5% (Formulation 17) to 2.0% (Formulation 22) as observed in FIGS. 4 and 5, the ratio of dermis/cumulative amount explained above is valid to demonstrate the superiority of Formulation 21 over 12, despite their different strength (1.0% and 0.5%, respectively).

The lag phase for the active ingredient in the formulations ranged from 8 to 12 hours post-dosing—after this period of time the active ingredient reached its steady state and demonstrated a constant skin flux. The ratio dermis (ng)/skin flux (ng*cm$^2$/hr) was used as an additional parameter to characterize the targeted delivery to the dermis observed for Formulation 21 in comparison to Formulation 12. From data shown on FIG. 7 the derived skin flux (slope with a $R^2 \geq 0.99$) for Formulations 21 and 12 are, respectively, 0.7251 ng*cm$^2$/hr and 0.9935 ng*cm$^2$/hr. Considering the different strengths of Formulations 21 and 12 (1.0% and 0.5%, respectively), the normalized skin flux values (skin flux divided by active ingredient strength) were 0.7251 ng*cm$^2$/hr and 1.987 ng*cm$^2$/hr, respectively. Using these normalized skin flux values and the dermis amounts converted to ng (from FIG. 7) covering the steady state region (after 8 hours), the ratios dermis (ng)/normalized skin flux (ng*cm$^2$/hr) were calculated. Formulation 21 demonstrated a selective delivery of the active ingredient to the dermis, with ratios of 1599.5, 1132.6 and 3200.7 at 9 hours, 12 hours and 15 hours, respectively. Formulation 12 showed a significantly different delivery profile, with ratios of 213.25, 108.57 and 117.73 at 9 hours, 12 hours and 15 hours, respectively.

One embodiment of the invention is a topical pharmaceutical emulsion composition comprising a therapeutically effective amount of 3,5-Dihydroxy-4-isopropyl-trans-stilbene or a pharmaceutically acceptable salt thereof, an oil phase, a water phase, a surfactant and an antioxidant, wherein the emulsion is homogenous, and wherein the composition administered in an in vitro system results in a ratio of dermis amounts (ng) measured at steady state to normalized (by active strength) skin flux (ng*cm$^2$/hr) from 1000 to 5000, using freshly excised abdominal human skin. In one embodiment, the 3,5-Dihydroxy-4-isopropyl-trans-stilbene or pharmaceutically acceptable salt thereof is solubilized in the oil phase of the emulsion composition.

In another embodiment of the invention there is a homogenous topical pharmaceutical emulsion composition comprising an effective amount of 3,5-Dihydroxy-4-isopropyl-trans-stilbene or a pharmaceutically acceptable salt thereof, an oil phase, a water phase, a surfactant and an antioxidant, wherein the composition produces an area under the curve (AUC) AUC(0-tau) of less than 30 ng*h/mL, or less than 23.5 ng*h/mL or less than 16 ng*h/mL in a human upon administration to the skin in an amount not exceeding 35% Body Surface Area (BSA). In another embodiment, the amount is not exceeding 30% BSA.

In one embodiment, the AUC is at steady state. In another embodiment, the amount of body surface area (BSA) for which the drug is applied to is less than 50%, in another embodiment the amount is less than 35%, in another embodiment the amount is less than 30%. It is recognized that if the BSA is >10% than the AUC may be increased accordingly.

As used herein, the term "AUC(0-last)" means the area under the plasma concentration versus time curve, from time 0 to the last measurable concentration as calculated by the log-linear trapezoidal method.

As used herein, the term "AUC(0-12)" means the area under the plasma concentration versus time curve, from time 0 to the 12-hour time point, as calculated by the log-linear trapezoidal method.

As used herein, the term "AUC(0-tau)" means the area under the plasma concentration versus time curve from time 0 to end of the dosing interval, as calculated by the log-linear trapezoidal method.

In another embodiment of the invention there is a homogenous topical pharmaceutical emulsion composition comprising an effective amount of 3,5-Dihydroxy-4-isopropyl-trans-stilbene or a pharmaceutically acceptable salt thereof, an oil phase, a water phase, a surfactant and an antioxidant, wherein the composition produces a $C_{max}$ (maximum plasma level of drug) at steady state, and the amount of body surface area (BSA) for which the active ingredient (1% strength) is applied to is 15-35% and produces a $C_{max}$ below 4 ng/ml and an AUC (0-8h) of no more than 16 ng.h/mL.

In patients with atopic dermatitis, when the active ingredient (0.5% strength) is applied once daily within the indicated BSA, 5-35% of patients produce plasma concentrations ranging from 40.8 ng/mL to 4170 ng/mL.

In patients with atopic dermatitis, when the active ingredient (0.5% strength) is applied twice daily within the indicated BSA, 5-35% of patients produce plasma concentrations ranging from 40.7 ng/mL to 10800 ng/mL.

In patients with atopic dermatitis, when the active ingredient (1% strength) is applied once daily within the indicated BSA, 5-35% of patients produce plasma concentrations ranging from 40.6 ng/mL to 1510 ng/mL.

In patients with atopic dermatitis, when the active ingredient (1% strength) is applied twice daily within the indicated BSA, 5-35% of patients produce plasma concentrations ranging from 41.4 ng/mL to 181000 ng/mL.

In one embodiment, there is a pharmaceutical composition for topical administration comprising the active ingredient 3,5-Dihydroxy-4-isopropyl-trans-stilbene present in an amount of about 1% w/w, or a pharmaceutically acceptable salt thereof, an oil phase, a water phase, a surfactant, and an antioxidant, and wherein the composition is homogenous, and produces a plasma concentration ranging from about 40.6 ng/mL to about 1510 ng/mL in a human upon administration to the skin once daily.

In one embodiment, there is a pharmaceutical composition for topical administration comprising the active ingredient 3,5-Dihydroxy-4-isopropyl-trans-stilbene present in an amount of about 1% w/w, or a pharmaceutically acceptable salt thereof, an oil phase, a water phase, a surfactant, and an antioxidant, and wherein the composition is homogenous, and produces a plasma concentration ranging from about 41.4 ng/mL to about 181000 ng/mL in a human upon administration to the skin twice daily.

In one embodiment, there is a pharmaceutical composition for topical administration comprising the active ingredient 3,5-Dihydroxy-4-isopropyl-trans-stilbene present in an amount of about 0.5% w/w, or a pharmaceutically acceptable salt thereof, an oil phase, a water phase, a surfactant, and an antioxidant, and wherein the composition is homogenous, and produces a plasma concentration ranging from about 40.8 ng/mL to about 4170 ng/mL in a human upon administration to the skin once daily.

In one embodiment, there is a pharmaceutical composition for topical administration comprising the active ingredient 3,5-Dihydroxy-4-isopropyl-trans-stilbene present in an amount of about 0.5% w/w, or a pharmaceutically acceptable salt thereof, an oil phase, a water phase, a surfactant, and an antioxidant, and wherein the composition is homogenous, and produces a plasma concentration ranging from about 40.6 ng/mL to about 1510 ng/mL in a human upon administration to the skin once daily.

| Study | | |
|---|---|---|
| Formulation | Formulation 1a | Formulation 21 |
| Age | 18-65 y | 18-65 y |
| Disease duration | ≥6 months diagnosis of AD | ≥6 months diagnosis of AD |
| Affected area | 1-10% BSA, excluding face, groin, scalp, genitals | 15-35% BSA, excluding scalp |
| IGA (0-5) | 2-3 (mild-moderate) | ≥3 (moderate-severe) |
| Average % BSA treated | 2.7% (1-7%) | 19.8% (15-33%) |
| Study duration | 28 day | 21 day |
| Study treatment | Vehicle, 0.5%, 1% BID | 1%, 2% BID (no vehicle control) |
| Subject numbers | N = 12/10/12 (completed) | N = 6/2 (completed) |
| PK sampling scheme | Pre-dose, 1, 2, 4, 6, 8 h post-dose | Pre-dose, 1, 2, 4, 8, 10, 12, 24 h post-dose |
| LLOQ | 0.1 ng/mL = 100 pg/mL | 40 pg/mL |
| 1% BID cohort data only | | |
| N | 12 | 6 |
| Day 1 Cmax (ng/mL) | 0.46 (0-3.32) | 1.23 (0.2-3.96) |
| Day 1 AUC (0-8) (ng · h/mL) | 1.22 (0-8.61) | 5.56 (1.05-15.14) |
| IGA score change from baseline at Day 21 | 42% (0%-100%) | 55% (33%-75%) |
| BSA affected change from baseline at Day 21 | 52% (−21%-100%) | 77% (56%-94%) |

Atopic Dermatitis is evaluated clinically and is based on historical features, morphology, distribution of skin lesions and associated clinical signs. Many formal sets of criteria have been developed to aid in classification. For measurement of disease severity, at least 28 different scales exist. Most commonly used include SCORAD index, the Eczema Area and Severity Index (EASI), the Investigators Global Assessment (IGA) and the Six area, Six sign Atopic Dermatitis (SASSAD) severity score. For purposes herein, the IGA scale or EASI scale will be referenced.

IGA is a static 5-point morphological assessment of overall disease severity, as determined by the physician, using the clinical characteristics of erythema, infiltration, papulation, oozing, and crusting as guidelines. The IGA is made without reference to the previous IGA scores.

IGA allows investigators to assess overall disease severity at one given time point, and it consists of a 5-point severity scale from clear to very severe disease (0=clear, 1=almost clear, 2=mild disease, 3=moderate disease, 4=severe disease). Some studies may use a 6-point scale of 5=very severe disease). IGA uses clinical characteristics of erythema, infiltration, papulation, oozing and crusting as guidelines for the overall severity assessment. While it appears that IGA has not been validated as an outcome measure, IGA has been used to validate other outcome scales as one "gold standard." While the combined use of IGA with another validated scale does not make IGA itself a stand-alone, validated instrument, IGA appears to correlate well with the EASI and is considered an instrument with reasonable face validity.

The EASI scoring system is a clinical tool for assessing the severity of AD that takes into account the overall severity of erythema, infiltration/papulation, excoriation, and lichenification, as well as the extent of BSA affected with AD. The 4 clinical signs are each graded on a 4-point scale (0 to 3) for each of the 4 specified body regions (head and neck, upper extremities, lower extremities, and trunk). EASI is also a static assessment made without reference to previous scores.

One embodiment of the invention is a method of treatment of atopic dermatitis (AD) in a patient in need thereof comprising administering to said patient a topical pharmaceutical emulsion composition comprising an effective amount of active 3,5-Dihydroxy-4-isopropyl-trans-stilbene or a pharmaceutically acceptable salt thereof, an oil phase, a water phase, a surfactant, and an antioxidant, wherein the emulsion composition is homogenous, and wherein the dosing is until the patient achieves a IGA score of clear (0) or almost clear (1) is reached or the patient has a 2-point improvement in the IGA score. In one embodiment, the active is solubilized in the oil phase of the composition.

In one embodiment, the patient achieves an IGA score of clear (0) or almost clear (1) from baseline. In another embodiment, the patient achieves a 2-point improvement from baseline on the IGA score. As a degree of measurement of severity, the patient will have started with an IGA score of ≥2 at baseline for purposes herein. In another embodiment, the patient will have started with an IGA score of ≥3 at baseline.

In one embodiment, the time the patient maintains without relapse, e.g. post treatment is 2 weeks or greater; 1 month or greater; or 2 months or greater, or 3 months or greater up to 12 months or greater. In one embodiment, the course of treatment is 52 weeks or less in duration of treatment, or is 28 weeks or less in duration of treatment, or is 21 weeks or less in duration of treatment, or is 16 weeks or less in duration of treatment, or is 12 weeks or less, or is 8 weeks or less, or is 4 weeks or less. In one embodiment of the invention the time to relapse is not influenced by the duration of treatment.

In another embodiment, there is a method of improving the % body surface area (BSA) of a person affected with atopic dermatitis (AD), the method comprising administering to said person a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the emulsion composition is homogenous, and wherein the % BSA improvement seen in the patient is from about ≥10-29%, or is >≥ than 30-49% or is ≥50-69% or is ≥70-89%, or is 90-100%.

Pruritus is the most frequent symptom of AD and potentially has the greatest effect on quality of life. In another embodiment, there is a method of reducing pruritus in a person with atopic dermatitis (AD) comprising administering to said person a topical pharmaceutical emulsion composition comprising an effective amount of 3,5-Di hydroxy-4-isopropyl-trans-stilbene or a pharmaceutically acceptable salt thereof, an oil phase, a water phase, a surfactant, and an antioxidant, and wherein the emulsion composition is homogenous, and the time to reduction of pruritus, and/or the % BSA affected with pruritus is reduced from a baseline measurement. In one embodiment, the formulations of the present invention may be compared to formulation 1 or 12.

Sleep disturbance is also considered to be a frequent symptom of AD and significantly impacts the quality of life for the patient and their associated family. In another embodiment there is a method of improving quality of sleep in a person with atopic dermatitis (AD), as measured by standard sleep assessments (such as by MOS-6), comprising administering to said person a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition and/or is homogenous, and whereby sleep is improved.

Caregivers of subjects with AD have a significantly impacted quality of life. In another embodiment there is a method of improving quality of life for caregivers of a person with atopic dermatitis (AD) such as measured by the WPAI or other suitable endpoints, comprising administering to said person a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition and/or is homogenous.

School-aged children with AD also experience substantial appearance and emotional distress as the result of the outward appearance of their skin and it significantly impacts the quality of life for the patient and their associated family. In another embodiment there is a method of improving quality emotional function in a school-aged person with atopic dermatitis (AD) as measured by emotional function (PED-QL) comprising administering to said person a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition and/or is homogenous.

Reduction in overall mental and physical function is also considered to be a frequent symptom of AD and significantly impacts the quality of life for the patient and their associated family. In another embodiment there is a method of improving overall quality of life in a person with atopic dermatitis (AD) as measured by standard mental and physical assessments (such as by SF-36) comprising administering to said person a topical pharmaceutical emulsion composition comprising an effective amount of 3,5-Dihydroxy-4-isopropyltrans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition and/or is homogenous.

One embodiment of the invention is a method of obtaining optimal dosing for the treatment of atopic dermatitis in a patient in need thereof, the method comprising administering to said patient a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, and wherein the emulsion is homogenous, and dosing continues until the patient achieves a IGA score of clear or almost clear is reached or a 2 point reduction of IGA score is achieved. In one embodiment, the patient achieves an IGA score of clear or almost clear. In one embodiment, the course of treatment is 28 weeks or less in duration of treatment, or is 21 weeks or less, or is 16 weeks or less in duration of treatment, or is 12 weeks or less in duration of treatment. In one embodiment, the time to relapse post treatment is 3 months or greater. In another embodiment, the time to relapse post treatment is 1 month or greater. In another embodiment, the time to relapse post treatment is 3 months or greater. In another embodiment, the time to relapse post treatment is 6 months or greater. In one embodiment of the invention the time to relapse is not influenced by the duration of treatment.

Another embodiment of the invention is a method for reducing the time to achieving a >50% improvement in IGA scores of clear or almost clear or a 2-point reduction in IGA score in a patient with atopic dermatitis in need thereof, the method comprising administering to said patient a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the emulsion composition is homogenous. A suitable comparator formulation would be formulation 1/1a or 12 (of similar % w/w active). In one embodiment, the time to achievement of the 50% reduction is at 12 weeks. In another embodiment, the time to achievement of the 50% reduction is at 8 weeks.

In one embodiment, the amount of 3,5-Dihydroxy-4-isopropyl-trans-stilbene or a pharmaceutically acceptable salt thereof, administered daily is from 10 mg to 100 mg. In another embodiment, the daily amount administered is from 10 mg to 50 mg.

In a similar manner, psoriasis can be assessed. Of the many psoriasis assessment tools currently available, the Psoriasis Area and Severity Index (PAST) and Physician Global Assessment (PGA) tools are most used. A PASI score is used to measure the severity and extent of psoriasis.

PASI examines four body regions: i) the head and neck, ii) the hands and arms, iii) the chest, abdomen and back (trunk) and iv) the buttocks, thighs and legs. Each region is given a score to show how much of the region is affected by psoriasis (area) and a score to record how bad the psoriasis is (severity). The area score can range from 0 (no psoriasis) to 6 (all of the skin affected). The severity score for each region is reached by adding scores for redness, thickness and scale, each of which is graded from 0 to 4, giving a maximum of 12. A PASI score of >10 is generally used to indicate a patient with moderate to severe plaque psoriasis.

The PGA scale in its typical use, is a 7-point scale ranging from clear to severe.

| | |
|---|---|
| Severe | Very marked plaque elevation, scaling, and/or erythema |
| Moderate to Severe | Marked plaque elevation, scaling, and/or erythema |
| Moderate | Moderate plaque elevation, scaling, and/or erythema |
| Mild to moderate | Intermediate between moderate and mild |
| Mild | Slight plaque elevation, scaling, and/or erythema |
| Almost clear | Intermediate between mild and clear |
| Clear | No signs of psoriasis |

One embodiment of the invention is a percent of patients achieving a 50% or a 75% reduction in PASI score (PASI 50 or PASI 75) achieved by using a topical emulsion composition as described herein. This may be a standalone clinical endpoint, or may be used in combination with the patient also reaching a PGA score of 0 or 1 (clear or almost clear) at a defined time point, such as at 8, 12 weeks, 16 weeks, 20, or 24 weeks, or greater than 24 weeks of treatment. As a degree of measurement of severity, the patient will most likely have started with a PGA score of ≥4 at baseline for purposes herein, e.g. one with moderate to severe plaque psoriasis.

One embodiment of the invention is a method of obtaining optimal dosing for the treatment of psoriasis in a patient in need thereof, the method comprising administering to said patient a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the emulsion composition is homogenous, and wherein the dosing continues until the patient achieves a PGA score of clear or almost clear is reached. In one embodiment, the course of treatment is 28 weeks or less in duration of treatment, or is 21 weeks or less, or is 16 weeks or less in duration of treatment, or is 12 weeks or less in duration of treatment. In one embodiment, the time to relapse post treatment is 3 months or greater. In another embodiment, the time to relapse post treatment is 6 months or greater. In one embodiment of the invention the time to relapse is not influenced by the duration of treatment.

Another embodiment of the invention is a method for reducing the time to achieving a >50% improvement in PGA scores of clear or almost clear or a 2-point reduction in PGA score in a patient with psoriasis in need thereof, the method comprising administering to said patient a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, and wherein the emulsion composition is homogenous. In one embodiment, the time to achievement of the 50% reduction is at 12 weeks. In another embodiment, the time to achievement of the 50% reduction is at 8 weeks. In one embodiment, the reduction of time may be compared to administration of a suitable comparator such as formulation 1/1a or 12 (of comparable % w/w active).

Alternatively, there is method is achieving a 50% or 75% reduction in PASI score in a patient with psoriasis in need thereof, the method comprising administering to said patient a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, and wherein the emulsion composition is homogenous.

In one embodiment, the course of treatment is 52 weeks or less in duration of treatment, or is 28 weeks or less in duration of treatment, or is 21 weeks or less, or is 16 weeks or less in duration of treatment, or is 12 weeks or less in duration of treatment, or is 2 months or less. In one embodiment, the time the patient maintains without replase, e.g. post treatment (also stated as time to relapse) is 2 weeks or greater, or 1 month or greater, or 2 months or greater or is 3 months or greater up to 12 months or greater. In another embodiment, the time to relapse post treatment is 6 months or greater. In one embodiment of the invention the time to relapse is not influenced by the duration of treatment. One suitable comparator formulation would be formulation 1 or 1a. In one embodiment, the time to achievement of the 50% reduction is at 12 weeks. In another embodiment, the time to achievement of the 50% reduction is at 8 weeks.

In another embodiment there is a method for reducing the time to achieving a >50% improvement in PGA scores of clear or almost clear or a 2-point reduction in PGA score and a PASI 50 or PASI 75 reduction in a patient with psoriasis in need thereof, comprising administering to said patient a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, and wherein the emulsion composition is homogenous. In one embodiment, the PASI score is a PAST 75. In another embodiment, the patient achieves a PGA score of clear or almost clear.

In another embodiment, there is a method of improving the time to reaching a PAST 50 or PAST 75 score in a person affected in a person with psoriasis, the method comprising administering to said person a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, and wherein emulsion composition is homogenous. In one embodiment, the time to reach a PASI 50 is at 16 weeks, or 12 weeks, or at 8 weeks. In another embodiment, the time to reach a PASI 70 is at 16 weeks, or 12 weeks, or at 8 weeks. A suitable comparator formulation would be formulation 1/1a or 12 (of comparable % w/w active).

Reduction in overall mental and physical function is also considered to be a frequent symptom of PSO and significantly impacts the quality of life for the patient and their associated family. In another embodiment there is a method of improving overall quality of life in a person with atopic dermatitis (PSO) as measured by standard mental and physical assessments (such as by SF-36) comprising administering to said person a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition and/or is homogenous.

Caregivers of subjects with AD have a significantly impacted quality of life. In another embodiment there is a method of improving quality of life for caregivers of a person with atopic dermatitis (AD) such as measured by WPAI scoring, comprising administering to said person a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, wherein the 3,5-Dihydroxy-4-isopropyl-trans-stilbene or pharmaceutically acceptable salt thereof is solubilized in the oil phase of the emulsion composition and/or is homogenous.

According to an embodiment, the invention provides a method of treating a dermatological condition or disorder in a patient in need thereof, the method comprising administering to said patient a topical pharmaceutical emulsion composition comprising an effective amount of 3,5-Dihydroxy-4-isopropyl-trans-stilbene or a pharmaceutically acceptable salt thereof, an oil phase, a water phase, a surfactant, and an antioxidant, and wherein the emulsion composition is homogenous. In another embodiment, the 3,5-Dihydroxy-4-isopropyl-trans-stilbene or pharmaceutically acceptable salt thereof is solubilized in the oil phase of the emulsion composition. In another embodiment, the oil phase comprises mineral oil or petrolatum. In another embodiment, if the oil phase comprises mineral oil or petrolatum, then a second oil phase component is present, and if the oil phase contains both mineral oil and petrolatum then a third oil phase component is present.

Another aspect of the invention is the use of a topical pharmaceutical emulsion composition comprising an effective amount of the active ingredient 3,5-Dihydroxy-4-isopropyl-trans-stilbene or a pharmaceutically acceptable salt thereof, an oil phase, a water phase, a surfactant, and an antioxidant, and wherein the emulsion composition is homogenous, in the manufacture of a medicament for the treatment of inflammatory skin diseases or disorders in a patient. In one embodiment, the active ingredient is solubilized in the oil phase of the emulsion composition. In another embodiment, the oil phase comprises mineral oil or petrolatum. In another embodiment, if the oil phase comprises mineral oil or petrolatum, then a second oil phase component is present, and if the oil phase contains both mineral oil and petrolatum then a third oil phase component is present. In one embodiment, the disease or disorder is atopic dermatitis, psoriasis or acne.

The compositions of the present invention may be used in a veterinary setting or in a medical setting, topically. It is recognized that the patient or subject may be an animal, a domestic animal, such as a mammal, including horses, cows, pigs, sheep, poultry, fish, cats, dogs and zoo animals. In one embodiment, the patient is an animal. In another embodiment, the patient is a mammal. In another embodiment, the mammal is a human. In another embodiment, the human is an adult, or a pediatric patient. In one embodiment, the pediatric patient is a child. In another embodiment, the pediatric patient is 3 months to 2 years of age and older.

In one embodiment, the dermatological condition or disorder for which treatment is sought is an inflammatory skin disease (e.g., a chronic inflammatory skin disease such as dermatitis (e.g., atopic dermatitis, contact dermatitis, eczematous dermatitis, or seborrhoic dermatitis), acne, psoriasis, rosacea, or aging skin.

In some aspects, the dermatological condition or disorder is selected from the group for the treatment of a skin disease, wherein the skin disease comprises a skin disorder of persistent inflammation, cell kinetics, and differentiation (e.g., psoriasis, psoriatic arthritis, exfoliative dermatitis, *Pityriasis rosea*, lichen planus, lichen nitidus, or porokeratosis); a skin disorder of epidermal cohesion, vesicular and bullous disorders (e.g., pemphigus, bulluous pemphigoi, epidermamolysis bullosa acquisita, or pustular eruptions of the palms or soles); a skin disorder of epidermal appendages and related disorders (e.g., hair disorders, nails, rosacea, perioral dermatitis, or follicular syndromes); a skin disorder such as an epidermal and appendageal tumors (e.g., squamous cell carcinoma, basal cell carcinoma, keratoacanthoma, benign epithelial tumors, or merkel cell carcinoma); a disorder of melanocytes (e.g., pigmentary disorders, albinism, hypomelanoses and hypermelanoses, melanocytic nevi, or melanoma); a skin disorder of inflammatory and neoplastic disorders of the dermis (e.g., erythema elavatum diutinum, eosinophils, granuloma facilae, pyoderma gangrenosum, malignant atrophic papulosis, fibrous lesions of dermis and soft tissue, or Kaposi sarcoma); a disorder of the subcutaneous tissue (e.g., panninculitis or lipodystrophy); a skin disorder involving cutaneous changes of altered reactivity (e.g., urticaria, angiodererma, graft-vs-host, allergic contact dermatitis, autosensitization dermatitis, atopic dermatitis, or seborrheic dermatitis); a skin change due to mechanical and physical factors (e.g., thermal injury, radiation dermatitis, corns, or calluses); photodamage (e.g., acute and chronic UV radiation, or photosensitization); or a skin disorder due to microbial agents (e.g., leprosy, lyme borreliosis, onychomycosis, tinea pedra, rubella, measles, herpes simplex, EBV (Epstein—Barr virus), HPV (Human papillomavirus) (e.g., HPV6 &7), warts, or prions).

In one embodiment, the inflammatory disorder is selected from the group consisting of psoriasis, and atopic dermatitis and acne. In an embodiment, the dermatological condition or disorder is psoriasis. In another embodiment, the dermatological condition or disorder is atopic dermatitis. In another embodiment, the dermatological condition or disorder is acne.

Definitions

The phrase "therapeutically effective amount" or "effective amount" is used herein to refer to an amount of the active ingredient sufficient to have a therapeutic effect upon administration, e.g. that amount which will cause an improvement or change in the condition for which it is applied when applied to the affected area repeatedly over a period of time. Effective amounts will vary with the particular condition being treated, the severity of the condition, the duration of the treatment, the stage of advancement of the condition, the body surface area affected with the clinical condition, and the specific components of the composition. An effective amount of the active ingredient for treatment of a condition or disorder can be determined by standard clinical techniques. Appropriate amounts in any given instance will be readily apparent to those skilled in the art or capable of determination by routine experimentation. The compositions are generally applied in topical manner to the affected area, i.e. localized application to the skin region where the clinical abnormality is manifest.

Concentrations, amounts, solubilities, and other numerical data may be presented herein in a range format. It is to be understood that such range format is used merely for convenience and brevity and should be interpreted flexibly to include not only the numerical values explicitly recited as the limit of the range, but also to include all the individual numerical values or sub-ranges encompassed within that range as if each numerical value and sub-range is explicitly recited. All numbers expressing quantities, percentages or proportions, and other numerical values used in the specification, are to be understood as being modified in all instances by the term "about".

For example, a concentration range of 0.1 to 5 ng/ml should be interpreted to include not only the explicitly recited concentration limits of 0.1 ng/ml and 5 ng/ml but also to include individual concentrations such as 0.2 ng/ml, 0.8 ng/ml, 1.0 ng/ml 2.2 ng/ml, 3.6 ng/mol, and sub-ranges such as 0.3-2.5 ng/ml, 1.8-3.2 ng/ml, etc. This interpretation should apply regardless of the breadth of the range or the characteristic being described.

The terms "administering" and "administration" are used herein to mean any method which in sound medical practice delivers the pharmaceutical emulsion composition to a patient in such a manner as to provide the desired therapeutic effect.

As used herein, "topical" administration of the pharmaceutical emulsion composition refers to application to and diffusion through the stratum corneum, including application to psoriatic lesions and broken skin.

As used herein, in the in vitro skin penetration studies the term "epidermis" includes the stratum corneum and tissue or layers down to the basement membrane, as isolated by heat separation treatment.

As used herein, in the in vitro skin penetration studies with ex-vivo human abdominal skin dermatomed at a thickness of 500 microns (+/−100 microns); the terms "epidermis" is the top/superficial layer obtained by heat separation procedure, and the term "dermis" is the underlying layer (after a washing/tape striping procedure).

The terms "treatment" or "treating" of a dermatological condition or disorder encompasses alleviation of at least one symptom thereof, a reduction in the severity thereof, or the delay, prevention or inhibition of the progression thereof. Treatment need not mean that the condition or disorder is totally cured. A useful pharmaceutical emulsion composition herein need only to reduce the severity of the condition or disorder, reduce the severity of symptoms associated therewith, provide improvement to a patient's quality of life, or delay, prevent or inhibit the onset of the condition or disorder. A treatment need not be effective in every member of a population, e.g. a population of patients with atopic dermatitis, to have clinical utility, as is recognized in the medical and pharmaceutical arts.

The term "pharmaceutically acceptable salt thereof" refers to salts that are safe and effective for topical use in the patient and possess the desired pharmaceutical activity. Such salts include salts formed when an acidic proton is replaced with a metal ion (e.g. alkali metal ion, alkaline earth metal ion, or aluminum ion).

The terms "pharmaceutically acceptable" and "dermatologically acceptable" mean approvable by a regulatory agency or listed in a Pharmacopeia or other generally recognized guide for use in animals, and more particularly in humans.

As used herein, the term "skin penetration" refers to the diffusion of the 3,5-Dihydroxy-4-isopropyl-trans-stilbene or a pharmaceutically acceptable salt thereof through the stratum corneum and into the epidermis and/or dermis of the skin.

As used herein, "patients" includes human patients, including adult, teens and children (e.g. pediatric patients). A pediatric patient can include teenagers under the age of 18. A child for purposes herein is under the age of 12.

As used herein, "solublize" means dissolved in a particular phase in an amount ≥50% w/w, or ≥60% w/w, or ≥70% w/w, or ≥80% w/w, or ≥90% w/w or ≥95% w/w, based on the percent by weight of the final composition prepared.

As used herein, "homogenous" means a uniform dispersal of one phase within the other. In the instance of an o/w emulsion it is the uniform dispersal of the oil phase within the water phase.

Any concentration range, percentage range or ratio range recited herein is to be understood to include concentrations, percentages or ratios of any integer within that range and fractions thereof, such as one tenth and one hundredth of an integer, unless otherwise indicated.

Unless otherwise indicated, all percentages are based on the percent by weight of the final composition prepared, and all totals equal 100% by weight.

It should be understood that the terms "a" and "an" as used herein refer to "one or more" of the recited components. It will be clear to one of ordinary skill in the art that the use of the singular includes the plural unless specifically stated otherwise.

Throughout the application, descriptions of various embodiments use "comprising" language, however in some specific instances, an embodiment can alternatively be described using the language "consisting essentially of" or "consisting of".

"Substantially free" of a specified component refers to a composition with less than about 1% by weight of the specified component. "Free" of a specified component refers to a composition where the specified component is absent.

As the biological profile, or the pK/pD of 3,5-Dihydroxy-4-isopropyl-trans-stilbene or a pharmaceutically acceptable salt, depends on the absence of degradation products and delivery of the active ingredient to the appropriate layers of the skin in efficacious amounts, compositions such as described herein offer patients a novel therapeutic treatment option for various inflammatory skin conditions.

Other terms used herein are intended to be defined by their well-known meanings in the art. The examples set forth below are illustrative of the present invention and are not intended to limit, in any way, the scope of the present invention. The following examples illustrate the invention. These examples are not intended to limit the scope of the present invention, but rather to provide guidance to the skilled artisan to prepare and use the compounds, compositions, and methods of the present invention.

While particular embodiments of the present invention are described, the skilled artisan will appreciate that various changes and modifications can be made without departing from the spirit and scope of the invention.

EXAMPLES

Example 1—Preparation of a Cream Comprising 0.5 w/w 3,5-Dihydroxy-4-Isopropyl-Trans-Stilbene The following cream composition was prepared:

TABLE 1

| | Formulation Number | |
|---|---|---|
| Ingredient | 1 % w/w | 1 (a) % w/w |
| Active Phase | | |
| Active ingredient | 0.50 | 1.00 |
| Propylene glycol | 10.00 | 10.00 |
| Diethylene glycol monoethyl ether | 2.00 | 2.00 |
| Polysorbate 80 | 1.00 | 1.00 |
| Water Phase | | |
| Purified water | 53.09 | 52.59 |
| Sodium acetate | 0.51 | 0.51 |
| Glacial acetic acid | 0.10 | 0.10 |
| Methylparaben | 0.18 | 0.18 |
| Propylparaben | 0.02 | 0.02 |

TABLE 1-continued

| | Formulation Number | |
|---|---|---|
| Ingredient | 1 % w/w | 1 (a) % w/w |
| Oil phase | | |
| Emulsifying Wax, BP | 7.20 | 7.20 |
| White petrolatum | 17.00 | 17.00 |
| Mineral oil | 6.00 | 6.00 |
| Steareth 2 | 1.50 | 1.50 |
| Steareth 20 | 0.90 | 0.90 |
| | 100.00 | 100.00 |

Due to chemical degradation of the active ingredient observed upon stability testing of this formulation, alternative formulations were then prepared where an antioxidant was added, and alternative preservative and buffer systems were used. Also, alternatively CRODEX can be replaced with POLAWAX. See Examples 2-4 below.

Example 2—Preparation of Cream Compositions Comprising 0.5% w/w 3,5-Dihydroxy-4-Isopropyl-Trans-Stilbene The following cream compositions were subsequently prepared

TABLE 2

| | Formulation Number | | | |
|---|---|---|---|---|
| Ingredient | 2 % w/w | 3 % w/w | 4 % w/w | 5 % w/w |
| Active Phase | | | | |
| Active ingredient | 0.50 | 0.50 | 0.50 | 0.50 |
| Polysorbate 80 | 1.00 | — | — | 1.00 |
| Propylene glycol | 10.00 | 10.00 | 10.00 | 10.00 |
| Diethylene glycol monoethyl ether | 2.00 | 2.00 | 2.00 | 2.00 |
| Water Phase | | | | |
| Purified water | 53.23 | 49.23 | 53.43 | 53.23 |
| Sodium citrate dihydrate | 0.19 | 0.19 | 0.19 | 0.19 |
| Citric acid | 0.08 | 0.08 | 0.08 | 0.08 |
| Disodium EDTA | 0.10 | 0.10 | 0.10 | 0.10 |
| Oil Phase | | | | |
| Petrolatum white | 17.00 | 17.00 | 17.00 | 17.00 |
| Light mineral oil | 6.00 | 6.00 | 6.00 | 6.00 |
| Steareth 2 | 1.50 | 1.50 | 1.50 | 1.50 |
| Steareth 20 | 0.90 | 0.90 | 0.90 | 0.90 |
| Antioxidant | 0.05 | 0.05 | 0.05 | 0.05 |
| Preservative | 0.25 | 0.25 | 0.25 | 0.25 |
| Non-ionic emulsifying wax | 7.20 | 12.20 | 8.00 | — |
| Sodium cetostearyl sulphate and cetearyl alcohol (Kolliphor CS A) | — | — | — | 7.20 |
| | 100.00 | 100.00 | 100.00 | 100.00 |

Example 3—Additional Cream Compositions Comprising 0.5% w/w 3,5-Dihydroxy-4-Isopropyl-Trans-Stilbene

TABLE 3

| Ingredient | 6 % w/w | 7 % w/w | 8 % w/w | 9 % w/w |
|---|---|---|---|---|
| Active Phase | | | | |
| Active ingredient | 0.50 | 0.50 | 0.50 | 0.50 |
| Polysorbate 80 | 2.88 | 1.00 | — | 1.00 |
| Polysorbate 20 | — | — | 2.88 | — |
| Propylene glycol | 10.00 | 10.00 | 10.00 | 10.00 |
| Diethylene glycol monoethyl ether | 2.00 | 2.00 | 2.00 | 2.00 |
| Water Phase | | | | |
| Purified water | 54.23 | 59.43 | 54.23 | 52.93 |
| Sodium citrate dihydrate | 0.19 | 0.19 | 0.19 | 0.19 |
| Citric acid | 0.08 | 0.08 | 0.08 | 0.08 |
| Disodium EDTA | 0.10 | 0.10 | 0.10 | 0.10 |
| Oil Phase | | | | |
| Petrolatum white | 17.00 | 17.00 | 17.00 | 17.00 |
| Light mineral oil | 6.00 | 6.00 | 6.00 | 6.00 |
| Steareth 2 | 1.50 | 1.50 | 1.50 | 1.50 |
| Steareth 20 | 0.90 | 0.90 | 0.90 | 0.90 |
| Propyl gallate | 0.05 | 0.05 | 0.05 | 0.05 |
| Benzoic Acid | 0.25 | 0.25 | 0.25 | 0.25 |
| Cetearyl alcohol | 4.32 | — | 4.32 | — |
| Glyceryl stearate + PEG 100 stearate | — | — | — | 7.50 |
| PEG 40 hydrogenated castor oil | — | 1.00 | — | — |
| | 100.00 | 100.00 | 100.00 | 100.00 |

Example 4—Further Cream Compositions Comprising 0.5% w/w 3,5-Dihydroxy-4-Isopropyl-Trans-Stilbene Based on the findings from Examples 2 and 3, Formulations 10-14 were selected for further development. Formulations 10-14 are the same as each other with the exception that different levels of active ingredient are present (ranging from 0%-2% w/w) and the water level is adjusted accordingly.

TABLE 4

| Ingredient | 10 % w/w | 11 % w/w | 12 (tergus) % w/w | 13 % w/w | 14 % w/w |
|---|---|---|---|---|---|
| Active Phase | | | | | |
| Active ingredient | 0.00 | 0.10 | 0.50 | 1.00 | 2.00 |
| Polysorbate 80 | 1.50 | 1.50 | 1.50 | 1.50 | 1.50 |
| Propylene glycol | 10.00 | 10.00 | 10.00 | 10.00 | 10.00 |
| Diethylene glycol monoethyl ether | 2.00 | 2.00 | 2.00 | 2.00 | 2.00 |
| Water Phase | | | | | |
| Purified water | 53.18 | 53.08 | 52.68 | 52.18 | 51.18 |
| Sodium citrate | 0.19 | 0.19 | 0.19 | 0.19 | 0.19 |
| Citric acid | 0.08 | 0.08 | 0.08 | 0.08 | 0.08 |
| Disodium EDTA | 0.10 | 0.10 | 0.10 | 0.10 | 0.10 |
| Oil Phase | | | | | |
| BHT | 0.10 | 0.10 | 0.10 | 0.10 | 0.10 |
| Benzoic Acid | 0.25 | 0.25 | 0.25 | 0.25 | 0.25 |
| Non-ionic emulsifying wax | 7.20 | 7.20 | 7.20 | 7.20 | 7.20 |
| Petrolatum white | 16.50 | 16.50 | 16.50 | 16.50 | 16.50 |
| Light mineral oil | 6.00 | 6.00 | 6.00 | 6.00 | 6.00 |
| Steareth 2 | 1.80 | 1.80 | 1.80 | 1.80 | 1.80 |
| Steareth 20 | 1.10 | 1.10 | 1.10 | 1.10 | 1.10 |
| | 100.00 | 100.00 | 100.00 | 100.00 | 100.00 |

Example 5—Method of Preparation

The cream compositions described in Examples 1-4 were prepared using the following general method:

Oil Phase:
1. To a suitably sized vessel, add oil phase ingredients (e.g. white petrolatum, mineral oil, steareth 2 and steareth 20), initiate mixing and heat to 70-80° C.
2. Once the oil phase is at 70-80° C., slowly add POLA-WAX, CRODEX or cetearyl alcohol (as the case may be). Mix until all materials are melted/dissolved and the oil phase is uniform in appearance.

Active Phase:
3. To another suitably sized vessel, add active phase ingredients (e.g. propylene glycol and diethylene glycol monoethyl ether). Heat to 50-60° C. while mixing.
4. Once the temperature has been reached, slowly add the active ingredient to the active phase while mixing. Maintain temperature at 50-60° C. and mix until uniform and free of undissolved particles and the active phase is uniform in appearance.

Water Phase:
5. Add water phase ingredients to the main mixing vessel (e.g. water and buffer). Begin mixing and heat to 70-80° C. Mix until all materials are fully dissolved and the water phase is uniform in appearance.

Emulsification:
6. Once the water and oil phases are free of undissolved particles, uniform in appearance and at 70-80° C., slowly vacuum transfer the oil phase into the main vessel containing the water phase. Scrape down the oil phase vessel and transfer to the main vessel.
7. Once the transfer and scrape-down are complete, maintain mixer settings and mix for 5-10 minutes while maintaining product temperature between 70-80° C. Verify the product is uniform in appearance.
8. Once uniform, maintain mixing and cool to 50-60° C.
9. Once the product and active phase temperatures are at 50-60° C., increase mixing and slowly vacuum transfer the active phase into the main vessel. Scrape down and rinse the active phase vessel using the reserved propylene glycol and transfer to the main vessel.
10. Once the transfer and scrape-down are complete, increase vacuum level and maintain mixer settings and mix for 5-10 minutes while maintaining product temperature between 50-60° C. Verify the product is uniform in appearance.
11. Once mixing is complete, maintain mixing and cool the batch to 30° C. (25-35° C.).
12. Once the temperature has been reached, reduce mixing and cool the batch to <25° C.
13. Once the product temperature is <25° C., mix for 15 minutes at high speed. Maintain product temperature at <25° C.

14. Once mixing is complete, reduce mixing speeds and verify the product is uniform in appearance. If necessary, cool the product to <25° C. prior to initiating product discharge.
15. Once uniform and the product temperature is <25° C., discharge the product into appropriate storage containers taking samples as necessary.

An alternative process where the water phase is added to the oil phase (i.e. the opposite of the above-mentioned process) resulted in a product with an unsatisfactory physical appearance and inferior chemical stability.

Example 6—Chemical and Physical Stability

Samples of Formulations 2-5 were stored at 25, 30 and 40° C. for 3 months and were subjected to visual analysis. Formulations 2-4 presented no discoloration or physical separation over the 3-month period. Formulation 5 however had signs of non-homogeneity.

The samples were also subjected to chemical stability analysis by HPLC using the following conditions:

Zorbax Bonus reverse phase column: 150×4.6 mm, 3.5 μm particle size with 4.0 mm guard frit Column temp: 25° C.
Autosampler temp: ambient
Flow rate: 1.0 ml/min
Injection volume: 15 μl
Detection: 235 nm
Run time: 50 minutes
Mobile Phase A: 0.1% TFA in water
Mobile Phase B: Acetonitrile

TABLE 5

HPLC elution gradient

| Time (minutes) | % B |
| --- | --- |
| 0 | 5 |
| 40 | 100 |
| 45 | 100 |
| 45.1 | 5 |
| 50 | 5 |

Formulations 2-5 met chemical stability specifications when stored at standard ICH conditions for up to 3 months. Formulations 6-9 displayed similar chemical and physical stability. Based on these findings, Formulations 10-14 were selected for further development. However, during process development of Formulations 10-14 it was observed from microscopic analysis that the emulsion structure of these formulations was non-uniform and had wax-like material present. The non-uniform emulsion is illustrated in FIG. 1 and was determined to be dependent on the concentration of the active ingredient. In other words, there was no such observation in Formulation 10 (placebo) and increased levels of heterogeneity were observed with increasing levels of active ingredient.

To identify which semi-solid ingredient is responsible for forming the non-uniform emulsion, experiments were conducted where each semi-solid ingredient was systematically substituted as follows:

TABLE 6

| Remove | Substitute |
| --- | --- |
| Emulsifying wax NF | Water |
| Steareth-2 & Steareth-20 | Water |

TABLE 6-continued

| Remove | Substitute |
| --- | --- |
| White petrolatum | Mineral oil |
| White petrolatum | Water |
| Emulsifying wax NF & white petrolatum | Water |

The formulation that was free of petrolatum was observed to have a uniform emulsion. Additional characterization was conducted using hot stage optical microscopy, XRD, IR microscopy and fluorescent microscopy. These techniques confirmed that the wax-like material was comprised of petrolatum and was a function of the concentration of the active ingredient present. These observations suggested that the petrolatum was not adequately emulsified and that the active ingredient was not solubilized in either the water phase or the oil phase of the emulsion.

Example 7—Development of Final Physically and Chemically Stable Cream Formulation Comprising 0.5% w/w 3,5-Dihydroxy-4-Isopropyl-Trans-Stilbene for Clinical Development The solubility of the active ingredient in different solvents was determined. The active ingredient was observed to have good solubility in medium chain triglycerides (MCT), which was chosen to replace the white petrolatum and mineral oil in the oil phase of the emulsion composition. The following formulations were prepared with 5%, 10%, 15% and 20% MCT (Formulations 15-18). Two formulations (Formulations 19 and 20) were also prepared where POLAWAX (a proprietary blend of cetostearyl alcohol and emulsifiers) was replaced with cetostearyl alcohol and additional emulsifier.

TABLE 7

| | Formulation Number | | | | | |
| --- | --- | --- | --- | --- | --- | --- |
| | 15 | 16 | 17 | 18 | 19 | 20 |
| Ingredient | % w/w | % w/w | % w/w | % w/w | % w/w | % w/w |
| Water Phase | | | | | | |
| Purified water | 53.68 | 58.68 | 65.18 | 70.18 | 63.38 | 65.18 |
| Sodium citrate | 0.19 | 0.19 | 0.19 | 0.19 | 0.19 | 0.19 |
| Citric acid | 0.08 | 0.08 | 0.08 | 0.08 | 0.08 | 0.08 |
| Disodium EDTA | 0.10 | 0.10 | 0.10 | 0.10 | 0.10 | 0.10 |
| Oil Phase | | | | | | |
| Active ingredient | 2.00 | 2.00 | 0.50 | 0.50 | 0.50 | 0.50 |
| Propylene glycol | 10.00 | 10.00 | 10.00 | 10.00 | 10.00 | 10.00 |
| Diethylene glycol monoethyl ether | 2.00 | 2.00 | 2.00 | 2.00 | 2.00 | 2.00 |
| BHT | 0.10 | 0.10 | 0.10 | 0.10 | 0.10 | 0.10 |
| Benzoic Acid | 0.25 | 0.25 | 0.25 | 0.25 | 0.25 | 0.25 |
| POLAWAX | 7.20 | 7.20 | 7.20 | 7.20 | — | — |
| Cetostearyl alcohol | — | — | — | — | 7.20 | 5.40 |
| MCT | 20.00 | 15.00 | 10.00 | 5.00 | 10.00 | 10.00 |
| Polysorbate 80 | 1.50 | 1.50 | 1.50 | 1.50 | 2.10 | 2.10 |
| Steareth 2 | 1.80 | 1.80 | 1.80 | 1.80 | 2.50 | 2.50 |
| Steareth 20 | 1.10 | 1.10 | 1.10 | 1.10 | 1.60 | 1.60 |
| | 100.00 | 100.00 | 100.00 | 100.00 | 100.00 | 100.00 |

Figure 3:
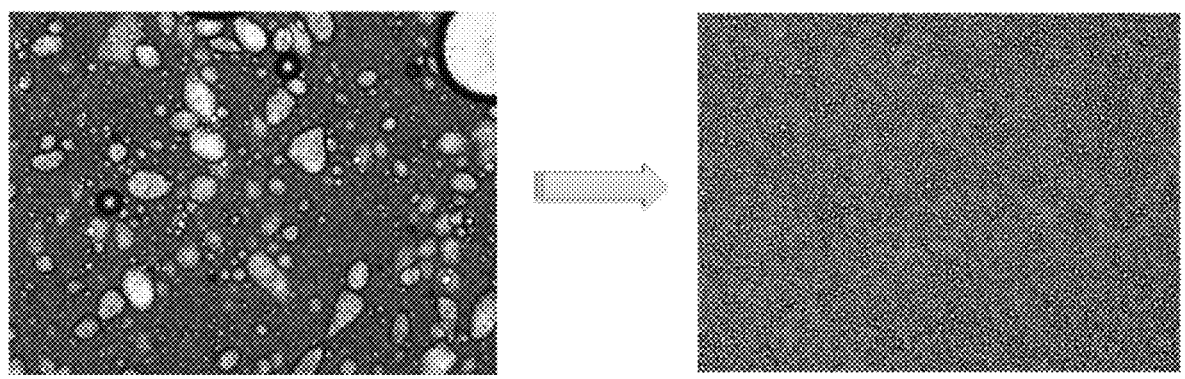
FIG. 3 illustrates the appearance of a non-uniform emulsion that was characteristic of Formulations 2-14 compared with the physically stable formulation characterized by Formulation 15-40.

Formulations 15-20 were subjected to microscopic analysis. All six formulations were found to be homogeneous and the dispersed oil phase had a small particle size and a uniform emulsion was observed. The difference in the appearance of a formulation with 10% MCT as the oil phase versus a formulation with larger amounts of white petrolatum and mineral oil as the oil phase is illustrated in FIG. 3. Without wishing to be bound by theory, it is thought that because the active ingredient is amphiphilic it has the potential to destabilize the emulsion, particularly when appropriate solvent selection is not made. It is thought that by using the appropriate solvent for the active ingredient in the oil phase, a more stable emulsion may be obtained.

Formulation 17 (0.5% active ingredient) was prepared, along with equivalent formulations containing 1% active ingredient, 2% active ingredient (Formulations 21 and 22, respectively) and 3% active ingredient (Formulation 26). Alternative formulations where 7.2% POLAWAX was replaced with 5.90% cetostearyl alcohol and increased surfactant levels were also prepared (Formulations 23 and 24). A variant of Formulation 17 but with 0.1% active ingredient is shown as Formulation 25. Formulation 17 met all chemical and physical stability specifications when stored at standard ICH conditions for up to 6 months. Thus, one embodiment of the invention is a chemically and physically stable pharmaceutical emulsion composition when stored at standard ICH conditions for up to 6 months comprising the active ingredient 3,5-Dihydroxy-4-isopropyl-trans-stilbene or a pharmaceutically acceptable salt thereof, an oil phase, a water phase, a surfactant, and an antioxidant, and wherein the active is solubilized in the oil phase of the emulsion composition. Another embodiment of the invention is a chemically and physically stable pharmaceutical emulsion composition when stored at standard ICH conditions for up to 6 months comprising the active ingredient 3,5-Dihydroxy-4-isopropyl-trans-stilbene or a pharmaceutically acceptable salt thereof, an oil phase, a water phase, a surfactant, and an antioxidant, and wherein the emulsion is homogenous. In another embodiment, the active is solubilized in the oil phase of the emulsion composition. In another embodiment, the average droplet size of the discontinuous phase is 1 micron or less.

Additional formulations were also made with changes to the co-solvents, e.g. Formulations 27 to 29. These data suggest that propylene glycol or Transcutol are not needed for physical stability of formulations, thus providing opportunities for alternative solvents for solubilization of the active ingredients to be used.

The formulations are shown in Table 8 below:

TABLE 8

| Ingredient | Formulation Number | | | | | | | | | |
|---|---|---|---|---|---|---|---|---|---|---|
| | 17 % w/w | 21 % w/w | 22 % w/w | 23 % w/w | 24 % w/w | 25 % w/w | 26 % w/w | 27 % w/w | 28 % w/w | 29 % w/w |
| Water Phase | | | | | | | | | | |
| Purified water | 65.18 | 64.68 | 63.68 | 63.18 | 61.18 | 65.58 | 62.68 | 75.18 | 67.18 | 77.18 |
| Sodium citrate | 0.19 | 0.19 | 0.19 | 0.19 | 0.19 | 0.19 | 0.19 | 0.19 | 0.19 | 0.19 |
| Citric acid | 0.08 | 0.08 | 0.08 | 0.08 | 0.08 | 0.08 | 0.08 | 0.08 | 0.08 | 0.08 |
| Disodium EDTA | 0.10 | 0.10 | 0.10 | 0.10 | 0.10 | 0.10 | 0.10 | 0.10 | 0.10 | 0.10 |
| Oil Phase | | | | | | | | | | |
| Active ingredient | 0.50 | 1.00 | 2.00 | 2.00 | 4.00 | 0.10 | 3.00 | 0.50 | 0.50 | 0.50 |
| Propylene glycol | 10.00 | 10.00 | 10.00 | 10.00 | 10.00 | 10.00 | 10.00 | — | 10.00 | — |
| Diethylene glycol monoethyl ether | 2.00 | 2.00 | 2.00 | 2.00 | 2.00 | 2.00 | 2.00 | 2.00 | — | — |
| BHT | 0.10 | 0.10 | 0.10 | 0.10 | 0.10 | 0.10 | 0.10 | 0.10 | 0.10 | 0.10 |
| Benzoic Acid | 0.25 | 0.25 | 0.25 | 0.25 | 0.25 | 0.25 | 0.25 | 0.25 | 0.25 | 0.25 |
| Emulsifying wax, NF | 7.20 | 7.20 | 7.20 | — | — | 7.20 | 7.20 | 7.20 | 7.20 | 7.20 |
| Cetostearyl alcohol | — | — | — | 5.90 | 5.90 | — | — | — | — | — |
| MCT | 10.00 | 10.00 | 10.00 | 10.00 | 10.00 | 10.00 | 10.00 | 10.00 | 10.00 | 10.00 |
| Polysorbate 80 | 1.50 | 1.50 | 1.50 | 2.10 | 2.10 | 1.50 | 1.50 | 1.50 | 1.50 | 1.50 |
| Steareth 2 | 1.80 | 1.80 | 1.80 | 2.50 | 2.50 | 1.80 | 1.80 | 1.80 | 1.80 | 1.80 |
| Steareth 20 | 1.10 | 1.10 | 1.10 | 1.60 | 1.60 | 1.10 | 1.10 | 1.10 | 1.10 | 1.10 |
| | 100.00 | 100.00 | 100.00 | 100.00 | 100.00 | 100.00 | 100.00 | 100.00 | 100.00 | 100.00 |

Example 8—Method of Preparation of Final Formulations

The cream compositions described in Example 7 were prepared using the following general method:

Oil Phase:
1. To a suitably sized vessel, add oil phase ingredients (e.g. MCT, POLAWAX NF, benzoic acid, BHT, propylene glycol, diethylene glycol monoethyl ether, polysorbate 80, steareth 2, steareth 20 and the active ingredient), initiate mixing and heat to 70-80° C., continue mixing until the active ingredient is dissolved and the phase is uniform in appearance.

Water Phase:
2. Add water phase ingredients to the main mixing vessel (e.g. water and sodium citrate, citric acid and Edetate disodium). Begin mixing and heat to 70-80° C. Mix until all materials are fully dissolved and the water phase is uniform in appearance.

Emulsification:
3. Once the water and oil phases are free of undissolved particles, uniform in appearance and at 70-80° C., slowly vacuum transfer the oil phase into the main vessel containing the water phase. Scrape down the oil phase vessel and transfer to the main vessel.
4. Once the transfer and scrape-down are complete, maintain mixer settings and mix for 5-10 minutes while maintaining product temperature between 70-80° C. Verify the product is uniform in appearance.

5. Transfer batch to holding vessel. Cool.

Thus, another embodiment of the present invention is a method of making an emulsion composition comprising
i) mixing and heating the oil phase ingredients and the active ingredient 3,5-Dihydroxy-4-isopropyl-trans-stilbene or a pharmaceutically acceptable salt thereof until dissolved;
ii) mixing the water phase ingredients until fully dissolved;
adding the oil phase ingredient of step (i) and the water phase ingredients of step (ii) and mixing until uniform in appearance. In one embodiment, the resulting emulsion composition is homogenous. In another embodiment, the active ingredient is solubilized in the oil phase. In another embodiment, the average droplet size of the discontinuous phase is about 35 microns or less. In another embodiment, the average droplet size of the discontinuous phase is less than about 25 microns. In another embodiment, the average droplet size of the discontinuous phase is less than about 15 microns. In another embodiment, the average droplet size of the discontinuous phase is less than about 10 microns. In another embodiment, the average droplet size of the discontinuous phase is less than about 5 microns. In another embodiment, the average droplet size of the discontinuous phase is about or is less than about 1 micron. In another embodiment, the average droplet size of the discontinuous phase is about 0.5 microns. In another embodiment, the average droplet size of the discontinuous phase is from about 0.05 to about 35 microns. In another embodiment, the average droplet size of the discontinuous phase is from about 0.05 to about 5 micron. In another embodiment, the average droplet size of the discontinuous phase is from about 0.05 to about 1 micron. In another embodiment, the average droplet size of the discontinuous phase is from about 0.1 to about 0.75 microns. In another embodiment, the average droplet size of the discontinuous phase is from about 0.05 to about 35 microns. In another embodiment, the average droplet size of the discontinuous phase (D50) is less than 5 microns. In another embodiment, the average droplet size of the discontinuous phase (D50) is less than 1 micron.

In another embodiment, there is a method of making an emulsion composition comprising
i) mixing and heating the oil phase ingredients and the active ingredient 3,5-Dihydroxy-4-isopropyl-trans-stilbene or a pharmaceutically acceptable salt thereof until dissolved;
ii) mixing the water phase ingredients until fully dissolved;
adding the oil phase ingredient of step (i) and the water phase ingredients of step (ii) and mixing until uniform in appearance, and the emulsion is homogenous and optionally has an average droplet size of the oil phase/discontinuous phase (D50) of less than 5 microns.

Example 9—Further Cream Compositions Comprising 1.0% w/w 3,5-Dihydroxy-4-Isopropyl-Trans-Stilbene To assist in identification of the semi-solid ingredients responsible for forming the non-uniform emulsion, additional experiments were conducted wherein petrolatum was kept in the formulation, mineral oil was removed and replaced by medium chain triglycerides (MCT) in the oil phase of the emulsion composition (see Table 9). In general, the variable for Formulations 30-32 was the % amount of petrolatum and the subsequent water concentrations. Formulations 33 and 37 demonstrate a lower level of petrolatum (4% and 2%) with 10% MCT. Formulation 34 demonstrates MCT and mineral oil together. Formulation 35 and 36 demonstrates a low level of mineral oil and petrolatum together with MCT, and lastly Formulations 38 and 39 demonstrate a low level of mineral oil and petrolatum together without MCT. Non-uniform emulsion characteristics were seen in formulations 34-37 of varying size. Formulations containing lower levels of petrolatum still lead to non-uniform emulsion characteristics with the active ingredient which might still be stable but are unknown at this time. Notably, mineral oil can be added in combination with MCT in the formulations.

TABLE 9

| | Formulation Number | | | | | | | | | | |
|---|---|---|---|---|---|---|---|---|---|---|---|
| Ingredient | 30 % w/w | 31 % w/w | 32 % w/w | 33 % w/w | 34 % w/w | 35 % w/w | 36 % w/w | 37 % w/w | 38 % w/w | 39 % w/w | 40 % w/w |
| Water Phase | | | | | | | | | | | |
| Purified water | 48.18 | 52.68 | 56.68 | 60.68 | 57.75 | 56.75 | 60.67 | 59.67 | 69.18 | 66.38 | 65.18 |
| Sodium citrate | 0.19 | 0.19 | 0.19 | 0.19 | 0.19 | 0.19 | 0.19 | 0.19 | 0.19 | 0.19 | 0.19 |
| Citric acid (anhydrous or monohydrate) | 0.08 | 0.08 | 0.08 | 0.08 | 0.09 | 0.09 | 0.09 | 0.09 | 0.08 | 0.08 | 0.08 |
| Disodium EDTA | 0.10 | 0.10 | 0.10 | 0.10 | 0.09 | 0.09 | 0.09 | 0.09 | 0.10 | 0.10 | 0.10 |
| Oil Phase | | | | | | | | | | | |
| Active ingredient | 1.00 | 1.00 | 1.00 | 1.00 | 2.00 | 2.00 | 2.00 | 2.00 | 0.50 | 0.50 | 0.50 |
| Propylene glycol | 10.00 | 10.00 | 10.00 | 10.00 | 10.00 | 10.00 | 10.00 | 10.00 | 10.00 | 10.00 | 10.00 |
| Diethylene glycol monoethyl ether | 2.00 | 2.00 | 2.00 | 2.00 | 2.00 | 2.00 | 2.00 | 2.00 | 2.00 | 2.00 | 2.00 |
| BHT | 0.10 | 0.10 | 0.10 | 0.10 | 0.10 | 0.10 | 0.10 | 0.10 | 0.10 | 0.10 | 0.10 |
| Benzoic Acid | 0.25 | 0.25 | 0.25 | 0.25 | 0.25 | 0.25 | 0.25 | 0.25 | 0.10 | 0.10 | 0.10 |
| Emulsifying wax, NF | 7.20 | 7.20 | 7.20 | 7.20 | 7.20 | 7.20 | 7.20 | 7.20 | 7.20 | 10.00 | 7.20 |
| White Petrolatum | 16.50 | 12.00 | 8.00 | 4.00 | — | 4.00 | 2.00 | 4.00 | 3.00 | 3.00 | — |
| MCT | 10.00 | 10.00 | 10.00 | 10.00 | 10.00 | 10.00 | 10.00 | 10.00 | — | — | — |
| Mineral Oil | — | — | — | — | 6.00 | 3.00 | 1.00 | — | 3.00 | 3.00 | 10.00 |

TABLE 9-continued

| Ingredient | Formulation Number | | | | | | | | | | |
|---|---|---|---|---|---|---|---|---|---|---|---|
| | 30 % w/w | 31 % w/w | 32 % w/w | 33 % w/w | 34 % w/w | 35 % w/w | 36 % w/w | 37 % w/w | 38 % w/w | 39 % w/w | 40 % w/w |
| Polysorbate 80 | 1.50 | 1.50 | 1.50 | 1.50 | 1.50 | 1.50 | 1.50 | 1.50 | 1.50 | 1.50 | 1.50 |
| Steareth 2 | 1.80 | 1.80 | 1.80 | 1.80 | 1.80 | 1.80 | 1.80 | 1.80 | 1.80 | 1.80 | 1.80 |
| Steareth 20 | 1.10 | 1.10 | 1.10 | 1.10 | 1.10 | 1.10 | 1.10 | 1.10 | 1.10 | 1.10 | 1.10 |
| | 100.00 | 100.00 | 100.00 | 100.00 | 100.00 | 100.00 | 100.00 | 100.00 | 100.00 | 100.00 | 100.00 |

Another aspect of the invention is to utilize the amphiphilic nature of the compound itself in formulating a more stable or homogenous composition, particularly between batches. As noted above, one hypothesis is that the drug molecule itself increases the packing parameters of the emulsion and thus destabilizes the emulsion possibly due to a decrease in droplet curvature. It is generally possible using a mixture of surfactants to estimate the average packing parameter from the molar quantities of the different surfactants in the composition. The packing parameters of the surfactants can help predict which surfactants will stabile o/w versus w/o emulsions.

It is believed that if you have too much of a material with similar packing parameters it changes the curvature of the droplets, destabilizing the emulsion. As such, Stearath-2, cetyl alcohol and stearyl alcohol are all similar in their critical packing parameter. Thus, one aspect of the invention is to decrease the amount of one of these surfactants, such as steareth 2 to better stabilize the emulsion. Other changes such as varying the molar ratios of Steareth 20, Tween 80 and the drug were also included. Using techniques such as microsopy, viscosity and conductivity the resulting compositions were assessed. The goal is to achieve a similar viscosity, e.g. 40-100 K, an absence of waxy regions and uniform distribution of the drug throughout the composition. Acceptable formulations were demonstrated. Table 10 below provides a representative set of examples of formulations using this approach.

TABLE 10

| Ingredients | # 41 | # 42 | # 43 | # 44 | #45 | # 46 | #47 | # 48 |
|---|---|---|---|---|---|---|---|---|
| | % w/w | | | | | | | |
| Active ingredient | 1.00% | 1.00% | 1.00% | 1.00% | 0.50% | 1.00% | 1.00% | 1.00% |
| Polysorbate 80 | 1.50% | 0.00% | 1.50% | 4.18% | 1.57% | 2.62% | 4.06% | 2.62% |
| Propylene Glycol | 10.00% | 10.00% | 10.00% | 10.00% | 10.00% | 10.00% | 10.00% | 10.00% |
| Transcutol | 2.00% | 2.00% | 2.00% | 2.00% | 2.00% | 2.00% | 2.00% | 2.00% |
| Water | 52.73% | 52.91% | 52.73% | 52.40% | 52.06% | 50.51% | 49.24% | 49.82% |
| Sodium Citrate | 0.19% | 0.19% | 0.19% | 0.19% | 0.19% | 0.19% | 0.19% | 0.19% |
| Citric Acid | 0.08% | 0.08% | 0.08% | 0.08% | 0.08% | 0.08% | 0.08% | 0.08% |
| EDTA Disodium | 0.10% | 0.10% | 0.10% | 0.10% | 0.10% | 0.10% | 0.10% | 0.10% |
| BHT | 0.10% | 0.10% | 0.10% | 0.10% | 0.10% | 0.10% | 0.10% | 0.10% |
| Benzoic Acid | 0.25% | 0.25% | 0.25% | 0.25% | 0.25% | 0.25% | 0.25% | 0.25% |
| Emulsfying Wax NF | 7.20% | 7.20% | 7.20% | 7.20% | 7.20% | 7.20% | 7.20% | 7.20% |
| White Petrolatum | 16.50% | 16.50% | 16.50% | 16.50% | 16.50% | 16.50% | 16.50% | 16.50% |
| Mineral Oil, light | 6.00% | 6.00% | 6.00% | 6.00% | 6.00% | 6.00% | 6.00% | 6.00% |
| Steareth 2 | 0.00% | 0.00% | 0.00% | 0.00% | 0.00% | 0.00% | 0.00% | 0.00% |
| Steareth 20 | 2.35% | 3.67% | 2.35% | 0.00% | 3.45% | 3.45% | 3.28% | 4.14% |

| Ingredients | #49 | #50 | # 51 | #52 | #53 | #54 | #55 | #56 |
|---|---|---|---|---|---|---|---|---|
| | % w/w | | | | | | | |
| Active ingredient | 0.00% | 1.00% | 1.00% | 1.00% | 1.00% | 1.00% | 1.00% | 1.00% |
| Polysorbate 80 | 4.06% | 2.79% | 2.75% | 4.06% | 4.06% | 6.68% | 4.06% | 7.86% |
| Propylene Glycol | 10.00% | 10.00% | 10.00% | 10.00% | 10.00% | 10.00% | 10.00% | 10.00% |
| Transcutol | 2.00% | 2.00% | 2.00% | 2.00% | 2.00% | 2.00% | 2.00% | 2.00% |
| Water | 49.38% | 52.56% | 51.41% | 50.10% | 48.38% | 45.76% | 46.08% | 41.82% |
| Sodium Citrate | 0.19% | 0.19% | 0.19% | 0.19% | 0.19% | 0.19% | 0.19% | 0.19% |
| Citric Acid | 0.08% | 0.08% | 0.08% | 0.08% | 0.08% | 0.08% | 0.08% | 0.08% |
| EDTA Disodium | 0.10% | 0.10% | 0.10% | 0.10% | 0.10% | 0.10% | 0.10% | 0.10% |

TABLE 10-continued

| | | | | | | | | |
|---|---|---|---|---|---|---|---|---|
| BHT | 0.10% | 0.10% | 0.10% | 0.10% | 0.10% | 0.10% | 0.10% | 0.10% |
| Benzoic Acid | 0.25% | 0.25% | 0.25% | 0.25% | 0.25% | 0.25% | 0.25% | 0.25% |
| Emulsfying Wax NF | 7.20% | 7.20% | 7.20% | 7.20% | 7.20% | 7.20% | 7.20% | 7.20% |
| White Petrolatum | 16.50% | 16.50% | 16.50% | 16.50% | 16.50% | 16.50% | 16.50% | 16.50% |
| Mineral Oil, light | 6.00% | 6.00% | 6.00% | 6.00% | 6.00% | 6.00% | 6.00% | 6.00% |
| Steareth 2 | 0.00% | 0.00% | 0.00% | 0.00% | 0.00% | 0.00% | 0.00% | 0.00% |
| Steareth 20 | 4.14% | 1.23% | 2.42% | 2.42% | 4.14% | 4.14% | 6.44% | 6.90% |

It has been noted that Example 3 of U.S. Pat. No. 7,868,047 contained an active in a "Galax" cream base which does not appear to be a compendial nor commercially available base. There a commercial product is available from WellSpring Pharmaceuticals, Fla., USA entitled "Glaxal" cream base that comprises water, petrolatum, cetearyl alcohol, paraffinum liquidum, cereareth-20, sodium phosphate and p-chloro-m-cresol.

Using Example 3 as a guide, two formulations were made using the WellSpring Glaxal base. The active ingredient 3,5-Dihydroxy-4-isopropyl-trans-stilbene was dissolved in ethanol and then added to the Glaxal base while mixing. Mixing was continued for 15 min until the formulations looked homogenous and then analyzed with microscopy.

Formulation 41 with 1% active ingredient and 42 with 2% active ingredient were made with the following compositions:

| Ingredient | % w/w |
|---|---|
| 3,5-Dihydroxy-4-isopropyl-trans-stilbene | 1-2 |
| Ethanol | 10 |
| Glaxal base | q.s. 100 |

As evidenced by microscopy, droplet/particle size increases as soon as active ingredient is added to the base and is dependent on the amount of active added. This is similar to observations seen with formulations similar to Formulation 12 which also contained both mineral oil and petrolatum.

Example 10—Effects of the Cream Compositions Comprising 3,5-Dihydroxy-4-Isopropyl-Trans-Stilbene on Skin Penetration Properties The object of this study was to determine the in-vitro skin penetration of 3,5-Dihydroxy-4-isopropyl-trans-stilbene.

In particular, Formulations 17 and 21-24 were tested for their ability to deliver the active ingredient into the epidermis and dermis, and were compared against Formulations 1 and 12.

Briefly, Formulations 1, 12, 17 and 21-24 comprising 3,5-Dihydroxy-4-isopropyl-trans-stilbene were evaluated using a skin penetration assay. This study was designed to determine drug permeation into the epidermis, dermis and receiving fluid. Freshly excised human abdominal skin was dermatomed to a thickness of 500±100 μm and mounted on flow-through diffusion cells using donor blocks to provide a leak proof seal, exposing a surface area of 1.0 cm². Diffusion cells were connected to multi-channel pumps with a flow rate of approximately 0.6 mL/hr with PBS. Each cell was then equilibrated in a heating manifold to ensure a skin surface temperature of 32° C. (for at least 30 min prior to dosing). Test articles were applied at a dose of 10 μl per skin section (10 mg test article/cm²). Test articles were applied to two separate donors to capture inter-individual variation and to at least seven skin sections per donor to capture intra-individual variation. At 15 hours, post-application, the skin surface was wiped with cotton swabs, and tape-stripped three times to remove any residual test article. The washed skin was heat split at the epidermal and dermal junction. The skin layers were placed in separate homogenization vials and the drug was extracted. The extraction of active ingredient from separate test articles served to assess the efficiency of the extraction solvent. The recovered drug concentrations were used to calculate skin penetration into the epidermis and dermis as a percentage of applied doses. 3,5-Dihydroxy-4-isopropyl-trans-stilbene was detected using a liquid chromatography/mass spectrometry.

The amount of 3,5-Dihydroxy-4-isopropyl-trans-stilbene delivered into the epidermis, dermis (15 hours post application) from Formulations 1, 12, 17 and 21-24 is shown in FIG. 4.

Error bars represent the standard error of the mean (SEM) of 8 to 14 replicates per formulation (four skin donors). Note: Since the dosing area of the diffusion cell was 1 cm², the amounts of 3,5-Dihydroxy-4-isopropyl-trans-stilbene illustrated in FIG. 4 represent μg/cm².

When comparing the 0.5% w/w 3,5-Dihydroxy-4-isopropyl-trans-stilbene formulations, it was observed the amount of 3,5-Dihydroxy-4-isopropyl-trans-stilbene delivered into the epidermis were similar for Formulation 17, Formulation 1 and Formulation 12. However, Formulation 17 delivered approximately 3-fold more 3,5-Dihydroxy-4-isopropyl-trans-stilbene to the dermis compared to Formulation 12 and Formulation 1. In addition, it was observed from the data for Formulations 17, 21 and 22 that the active ingredient was delivered in a dose dependent manner. Similarly, it was observed from the data for Formulations 23 and 24 that the active ingredient was delivered in a dose dependent manner.

There appeared to be an inverse relationship in the amount of 3,5-Dihydroxy-4-isopropyl-trans-stilbene delivered into the receiving fluid over fifteen hours, where Formulation 17 showed a 2-4-fold lower amount compared to Formulation 12 and Formulation 1. Similar to the amounts delivered to the skin layers (epidermis and dermis), it was observed from the data for Formulations 17, 21 and 22 that the active ingredient was delivered in a dose dependent manner into the receiving fluid. Similarly, it was observed from the data for Formulations 23 and 24 that the active ingredient was delivered in a dose dependent manner into the receiving fluid.

Example 11—Effects of the Cream Compositions Comprising 3,5-Dihydroxy-4-Isopropyl-Trans-Stilbene on Skin Deposition Previous studies, showed Formulation 17 delivered higher amounts of 3,5-Dihydroxy-4-isopropyl-trans-stilbene to the dermis with lower amounts partitioning into the receiving fluid compared to Formulation 12. To further explore this observation, a study was conducted in human ex vivo skin to measure dermal levels every three hours (0-15 hours) and at 24 hours and compared to the concentrations measured in the receiving fluid.

Formulations 12 and 21 comprising 0.5% and 1.0% 3,5-Dihydroxy-4-isopropyl-trans-stilbene respectively were evaluated using an ex vivo human skin penetration assay. This study was designed to determine drug permeation into the epidermis, dermis and receiving fluid with more additional sampling for skin deposition. Freshly excised human abdominal skin was dermatomed to a thickness of 500±100 μm and mounted on flow-through diffusion cells using donor blocks to provide a leak proof seal, exposing a surface area of 1.0 $cm^2$. Diffusion cells were connected to multi-channel pumps with a flow rate of approximately 0.6 ml/hr with PBS. In order to keep the skin integrity and prevent bacterial growth, the seventy-two hour study receiving fluid contained 1% antibiotic-antimycotic. Each cell was then equilibrated in a heating manifold to ensure a skin surface temperature of 32° C. (for at least 30 min prior to dosing). Test articles were applied at a dose of 10 μl per skin section (10 mg test article/$cm^2$). Test articles were applied to two separate donors to capture inter-individual variation and to at least seven skin sections per donor to capture intra-individual variation. Receiving fluid was collected hourly for 72 hours as a measurement of active ingredient penetrating through the skin. At 3, 6, 9, 12, and 15 hours post-application, the skin surface was wiped with a cotton swab and tape-stripped three times to remove any residual test article considered not penetrating the skin. The washed skin was heat split at the epidermal and dermal junction. The skin layers were placed in separate homogenization vials and the drug was extracted using an Omni bead homogenizer. The recovered drug concentrations were used to calculate skin penetration into the epidermis and dermis as a percentage of applied doses. 3,5-Dihydroxy-4-isopropyl-trans-stilbene was detected using a liquid chromatography/mass spectrometry method described previously.

Formulation 21 showed the same trend observed previously, where the concentrations of 3,5-Dihydroxy-4-isopropyl-trans-stilbene delivered to the dermis were higher compared to Formulation 12. See FIG. 6. The trend for increased dermal deposition or tissue residency from Formulation 21 appeared as early as 3 hours post application and continued over the 15 hours of dosing.

Later time points (i.e. greater than 15 hours) were not considered for tissue analysis (epidermis and dermis) as the skin started losing its integrity, which could potentially result in inaccurate measured levels of active ingredient.

The same inverse relationship in the amount of 3,5-Dihydroxy-4-isopropyl-trans-stilbene delivered into the receiving fluid was observed, where Formulation 21 showed a 1.4 fold lower amount compared to Formulation 12 (FIG. 7). This trend for lowered delivery to the receiving fluid was consistent over the entire 72 hours of dosing as both formulations appeared to be in a steady state after 12 hours (lag phase). Despite Formulation 21 (1% w/w) having double the concentration of active ingredient as Formulation 12 (0.5% w/w), Formulation 21 was not able to deliver equivalent amounts into the receiving fluid. This suggests Formulation 21 is able to alter tissue residence preventing the active ingredient from partitioning from the skin into the receiving fluid.

In one embodiment of the invention is the use of a formulation such as described above which can provide lower systemic exposure of the active ingredient to the patient during use. In another embodiment, the dosing frequency to the affected area(s) may be now be dosed less frequently than previously envisioned. Application of a composition of the present invention may be applied to affected areas twice daily, once daily, once every other day; twice weekly; three times weekly, or once weekly, with the dose represented by any of the embodiments herein. In another embodiment, the treatment may be administered in two phases, an initial dosage frequency such as once or twice daily, followed by a maintenance phase, such as every other day; twice weekly; three times weekly, or once weekly.

Example 12—Biological Activity in Ex Vivo Human Skin from Cream Compositions Comprising 3,5-Dihydroxy-4-Isopropyl-Trans-Stilbene Target profiling revealed 3,5-Dihydroxy-4-isopropyl-trans-stilbene to be an activator of the AhR pathway in intestinal human colon adenocarcinoma. BioMAP®, a system that can offer physiologically relevant insights about a compound prior to lengthy and expensive animal or clinical studies, confirmed that Ahr is likely to be a primary target of 3,5-Dihydroxy-4-isopropyl-trans-stilbene. 3,5-Dihydroxy-4-isopropyl-trans-stilbene has also been shown to induce the expression of the AhR target gene, cyp1a1, in primary human keratinocytes, and human or rodent leukocytes. A model using freshly excised human skin has been developed to explore intrinsic efficacy of active ingredients (i.e., target engagement). This model allows topical formulations to be applied to explore pharmacodynamic activity in the skin. This study compares the biological activity of 3,5-Dihydroxy-4-isopropyl-trans-stilbene through Cyp1A1 induction from Formulations 17, 21 and 22 as compared to Formulation 12.

Tissue Culture Using Static Cells:

Freshly excised healthy human skin was dermatomed to 750 um and cleaned with antibiotic/antimycotic solution made up as 1% GIBCO™ Antibiotic-Antimycotic (100×), 0.1% Gentamicin in 1×Dulbecco's Phosphate Buffered Saline. Twelve mm diameter biopsies were cut using disposable single-use biopsy punches and washed in antibiotic/antimycotic solution for 5-10 minutes. Skin biopsies were placed on autoclaved 7 mm (0.38 $cm^2$) unjacketed static cells with 2 ml receptor volume and leak proof seal was maintained using metal clamps and donor chamber. Receptor chamber was filled with cornification media using pastuer pipette to dispense in sampling port. Static cells were then placed in a humidified incubator at 37° C. Test articles were applied topically (to the exposed/dry epidermis) on Day 1. (Day−1). Twenty-four hours later (Day 0), media in the receptor chamber was replaced with an activation cocktail designed to stimulate skin-resident immunocompetent cells. Twenty-four hours later (Day 1) the tissue was removed, minced to less than 1×1×1 mm pieces and stored in 10× volume of RNA later with 300 μl of RNeasy Lysis Buffer supplemented with 1% 2-Beta-Mercapto-Ethanol for RNA isolation.

Cornification Media:

Media consisted of 237 ml of Dulbecco's Modified Eagle Medium (DMEM), 237 ml Ham's F-12K Medium, 1 ml 90 mM Adenine, 1 mL 0.94M CaCl, 1 ml 10 nM Tri-iodothyronine, 1 ml Insulin-Transferrin-Selenium-Ethanolamine (ITS-X) (100×), 5 ml Antibiotic-Antimycotic (100×), 10 ml Fetal Bovine Serum (FBS), 5 ml GlutaMAX™ Supplement, 0.1 ml 50 mg/ml Gentamicin.

Activation Cocktail:

An ex vivo human skin target engagement model was originally developed to mimic the pro-inflammatory state of lesional psoriatic skin. The model may be found in Smith et al., PLOS ONE, DOI:10.1371/journal.pone.0147979; Feb. 12, 2016 and is referenced herein as the sRICA (skin-resident immune cell activation) assay. As such, skin resident immunocompetent cells were activated in situ with a combination of 1 ug/ml purified NA/LE Mouse anti-human CD3, 2 ug/ml CD28, 1 ug/ml anti-human IFN-gamma, 1 ug/ml anti-human IL-4 antibodies and 10 ng/ml recombinant human (rh) IL-1b/IL-1F2, 10 ng/ml rh IL-6 (R&DSystems, 1 ng/ml rh TGF-b1, and rh IL-21. All components incorporated in a single mixture with the cornification media (i.e., activation cocktail).

RNA Isolation & Quantitation:

Approximately 40 mg of minced tissue was added to homogenization tubes containing 2.8 and 1.4 mm ceramic beads. The tissue was disrupted using high-throughput bead mill homogenizer machine at 6300 rpm for 30 seconds and 10 cycles with a 2-minute ice break. The homogenate was digested by adding 490 µl of water containing 10 ul Proteinase K at 55° C. for 15 minutes. Digested tissue was spun down for 3 minutes at 10,000×g to pellet cell debri and the supernatant was used for RNA isolation using Qiagen's Mini RNA Isolation kit according to manufacturer's protocol. Total RNA was quantified using Nanodrop 2000. Isolated RNA (1.4 ug) from skin tissue was used as a template in a 20 ul PCR volume using Invitrogen SuperScript VILO cDNA Synthesis kit to create cDNA template. The cDNA was diluted 1:25 for subsequent qPCR with the specific TaqMan probe for each gene to be quantified. Life Technologies AVii7 PCR machine was used for the qPCR 40 amplification cycles. RNA levels of Cyp1a1 relative expression were calculated using the Delta CT formula and normalized to untreated skin sections.

Formulations 17, 21 and 22 and Formulation 12 showed biological activity for 3,5-Dihydroxy-4-isopropyl-trans-stilbene in human skin as measured indirectly by Cyp1A1 mRNA. There were no differences in the biological activity between these formulations. The lack of dose response from Formulations 17, 21 and 22 suggests this upregulation has reached a max or plateau that is likely achieved with formulations containing 0.5% 3,5-Dihydroxy-4-isopropyl-trans-stilbene or below. These data confirm the concentrations quantified in the in vitro skin penetration studies are bioavailable and capable of engaging targets within human skin. What has been found is that this assay does not provide statistically significant differences between formulations and/or concentrations of active in the formulations.

Example 13—Systemic Exposure and Skin Concentrations of 3,5-Dihydroxy-4-Isopropyl-Trans-Stilbene Following 7-Day Topical Administration to Gottingen Minipigs To assess tissue concentrations and systemic exposure, a toxicokinetics study in Gottingen minipigs was conducted with repeat topical administration of 3,5-Dihydroxy-4-isopropyl-trans-stilbene over 7 days. To compare systemic exposure to local skin tissue levels, tissue biopsies were collected, sectioned, and analyzed for active ingredient and compared to plasma concentrations on Day 1 and Day 7. A similar methodology for skin biopsies in minipigs is described in the literature such as by Mitra A, et al., Use of Minipig Skin Biopsy Model as an Innovative Tool to Design Topical Formulation to Achieve Desired Pharmacokinetics in Humans. *J Pharm Sci.* 2015, Feb. 17.

Formulation 22 (2% of active ingredient) and Formulation 12 (2.0%, e.g. formulation 14) were applied to the non-abraded skin of minipigs (3 males/group) at a dose of 2% daily (for a period of approximately 23 hours) for 7 days. Dermal application sites for these groups were 10% of the total body surface area. The dose weight was 2 g/kg/day, as determined by formulation feasibility testing conducted prior to the start of dosing (the appropriate vehicle was applied to 10% of the total body surface area of the first minipig in each of the aforementioned dose groups for approximately 23 hours). Hair was removed from the back and flanks of each animal on Days 1, 7 and 14, and as needed during the study. Application sites were semi-occluded with gauze patches held in place with tape and tubular netting. At the end of the exposure period, the netting and patches were removed, and all sites were wiped with warm reverse osmosis-treated water and cotton gauze.

The following endpoints/parameters were evaluated: clinical observations, dermal irritation (scored using the Draize method, body weights, and macroscopic and microscopic observations (treated and untreated skin). Toxicokinetic evaluation was performed on samples collected on Days 1 and 7 for plasma and skin concentrations.

On Day 7, the minipigs were euthanized and the surface of the skin was cleaned through a combination of several wash steps including mild cleansers, solvents, shaving, and tape stripping to ensure residual formulation was removed from the surface of the skin. The skin was then excised and skin was placed epidermis side down on a clean surface. Skin biopsies (8 mm) were harvested from the dosing areas, placed in cryotubes, and immediately frozen until analysis. While still frozen, the hypodermis was removing using a razor blade and the upper section of the sample (epidermis and upper dermis, section from 0 to 500 µm) was then cut away from the dermis. Therefore, epidermis refers to the upper section of the skin sample consisting of stratum corneum, epidermis, and upper dermis (approximately 500 µm) and dermis represents deeper dermis (approximately 1,500 µm meaning a cut of middle dermis to subcutaneous fat). The epidermis and dermis sections were then weighed and homogenized in 1 ml of a 75:25 water:acetonitrile solution containing 0.1% formic acid. The homogenate was further processed by protein precipitation using a solution of 100% acetonitrile with 0.1% formic acid and an internal standard (5 ng/ml). The supernatant from the protein precipitation was passed through an Ostro 96 well plate to remove phospholipids.

Formulation 22 resulted in higher skin deposition of 3,5-Dihydroxy-4-isopropyl-trans-stilbene, in the upper 500 µm and lower 1,500 pm sections, compared to Formulation 12 (with 2% active ingredient, also referred to herein as Formulation 14). The increase in the skin loading was observed on Day 1 and continued after 7 days of repeat dosing. This data suggests Formulation 22 has the capability of changing the skin microenvironment after a single application but can also maintain this effect over longer dosing periods.

Surprisingly, the systemic exposure as measured by AUC on Day 1 and Day 7 was lower for Formulation 22 compared to Formulation 12 (with 2% active ingredient, e.g. Formulation 14). The plasma concentrations seemed to decrease further for Formulation 22 by Day 7, where the levels were approximately 2.5 fold lower for Formulation 22 compared to Formulation 12 (with 2% active ingredient, e.g. Formulation 14). The data correlates with what was observed in the in vitro human skin penetration studies where Formulation 22 showed higher skin deposition with lower concentrations of 3,5-Dihydroxy-4-isopropyl-trans-stilbene delivered to the receiving fluid. The combination of this data suggests that Formulation 22 is capable of delivering higher tissue amounts to the target site, while minimizing systemic exposure.

Based on in vitro skin penetration flux and human data, predicted human AUCs are expected be below 50 ng*h/mL, or below 42.5 ng*h/mL and the predicted $C_{max}$, is expected to be below 15 ng/ml or 12.5 ng/mL.

Example 14—Systemic Exposure and Skin Concentrations of 3,5-Dihydroxy-4-Isopropyl-Trans-Stilbene Following 28-Day Topical Administration to Gottingen Minipigs The 7-day topical administration of 3,5-Dihydroxy-4-isopropyl-trans-stilbene in Formulation 22 showed significant concentrations of 3,5-Dihydroxy-4-isopropyl-trans-stilbene in the skin of Gottingen minipigs. The systemic levels from this study decreased from Day 1 to Day 7, suggesting Formulation 22 is capable of delivering higher tissue amounts to the target site, while minimizing systemic exposure. To see if this trend would continue over a longer dosing period, a repeat dosing of topical administration of 3,5-Dihydroxy-4-isopropyl-trans-stilbene over 28 days was conducted to assess the tissue concentrations, dermal toxicity, dermal irritancy and toxicokinetics from Formulation 22.

TABLE 10

| | AUC | | | Cmax | | |
|---|---|---|---|---|---|---|
| Nonclinical Study | NOAEL (ng · h/mL) | Predicted (ng · h/mL) | Margin of safety | NOAEL (ng/mL) | Predicted (ng/mL) | Margin of safety |
| Dermal 4% cream, BID, Minipig, 13 weeks | 99 | 42.5 | 2 | 7.13 | 12.5 | <1 |
| Subcutaneous 3 mg/kg/day, Rat, 13 weeks | 99 | 42.5 | 2 | 31.6 | 12.5 | 2.5 |

Based on in vivo minipig data and human data, the predicted human AUCs are expected to be below 30.0 ng*h/mL, or below 23.5 ng*h/mL administered at a 2% w/w strength of active to the human skin. Based on in vivo minipig data and human data, the predicted $C_{max}$ is expected to be below 15 ng/ml or below 11.3 ng/mL administered at a 2% w/w strength of active to the human skin.

Based now upon limited human data, human AUCs (0-8 h) are expected to be below 16.0 ng*h/mL, or below 14 ng*h/mL, or below 11 ng*h/mL administered at a 1% w/w strength of active to the human skin. In another embodiment, the $C_{max}$ is expected to be below 5 ng/ml, or below 4 ng/ml, or below 3 ng/ml, administered at a 1% w/w strength of active to the human skin.

The formulations were administered as a twice daily (10±1 hours apart) topical application to the dorsal skin (~10% of total body surface area) of Gottingen minipigs (3/sex/group) for 28 days and the dermal toxicity, dermal irritancy and of 3,5-Dihydroxy-4-isopropyl-trans-stilbene was determined. The initial daily doses were 0 (vehicle), 10, 20 or 60 mg/kg/day 3,5-Dihydroxy-4-isopropyl-trans-stilbene (concentrations at 0, 0.5, 1.0 and 3.0% w/w, respectively) at a dose formulation weight of 1 g/kg/dose (2 g/kg/day). Following dose application on each dosing day, the dose sites were semi-occluded for approximately 20±1 hours from the first dose and then gently washed before the next dose was applied.

TABLE 11

| | AUC | | | Cmax | | |
|---|---|---|---|---|---|---|
| Nonclinical Study | NOAEL (ng · h/mL) | Predicted (ng · h/mL) | Margin of safety | NOAEL (ng/mL) | Predicted (ng/mL) | Margin of safety |
| Dermal 4% cream, BID, Minipig, 13 weeks | 99 | 23.5 | 4 | 7.13* | 11.3 | ~1 |
| Subcutaneous 3 mg/kg/day, Rat, 13 weeks | 99 | 23.5 | 4 | 31.6 | 11.3 | 3 |

TABLE 12

Mean Plasma and Skin Toxicokinetic Parameters Following Twice Daily Dermal Administration of 3,5-Dihydroxy-4-isopropyl-trans-stilbene in Formulation 22 to Male and Female Göttingen Minipigs

|  |  | Male | | | | Female | | | |
|---|---|---|---|---|---|---|---|---|---|
|  |  | Daily Dose (mg/kg/day)$^a$ | | | | | | | |
|  |  | 0 | 10 | 20 | 60 | 0 | 10 | 20 | 60 |
| Numbers of Animals: | | 3 | 3 | 3 | 3 | 3 | 3 | 3 | 3 |
| AUC$_{(0-t)}$ (ng · h/mL) | Day 1 | NA | NA | NA | NR | NA | NR | NA | NR |
|  | Day 28 | NA | NA | NA | NR | NA | NR | NA | 4.84 |
| C$_{max}$ (ng/mL) | Day 1 | NA | NA | NA | 0.376 | NA | NR | NA | 0.408 |
|  | Day 28 | NA | NA | NA | 0.845 | NA | 0.395 | NA | 0.830 |
| Skin Concentration (Day 29; ng/g) | | | | | | | | | |
| Epidermis/Upper Dermis | | — | 4830 | 3950 | 10000 | — | 2540 | 2270 | 6530 |
| Lower Dermis | | — | 166 | 615 | 3660 | — | NQ | 305 | 3.04 |

NA: Not Applicable.
NR: Not reported due to the limited data;
NQ: Not quantifiable, the concentration below the limit of quantitation (0.300 ng/mL for plasma and 0.25 ng/mL for skin)
$^a$Doses expressed in terms of parent compound.

On Days 1 and 28, 3,5-Dihydroxy-4-isopropyl-trans-stilbene was not quantifiable in plasma at 5 and 10 mg/kg/dose (10 and 20 mg/kg/day) except for 2 time points on Day 28 (3 and 24 hours post first dose) which had 1 concentration value at each time point for females at 5 mg/kg/dose (10 mg/kg/day). At 30 mg/kg/dose (60 mg/kg/day), 3,5-Dihydroxy-4-isopropyl-trans-stilbene was quantifiable in plasma up to 3 hours after dosing (either first or second dose) on Days 1 and 28.

The T$_{max}$ values ranged from 1 to 3 hours post-dose (either first or second dose) on Days 1 and 28 at the 60 mg/kg/day dose level. The C$_{max}$ values ranged from 0.306 to 1.81 ng/ml for males and females. Generally, AUC$_{0-t}$ could not be reported due to the majority of the concentrations values being lower than the limit of quantification.

3,5-Dihydroxy-4-isopropyl-trans-stilbene concentrations were generally higher in the epidermis/upper dermis of both males and females than those in the lower dermis. The gender-averaged individual animal skin concentrations at necropsy were highest in the 60 mg/kg/day group at 8265 ng/g in the epidermis/upper dermis and 1830 ng/g in the lower dermis. Comparison of the concentrations in the skin to those in the plasma could not be assessed since the Day 28 24-hour plasma concentrations were below the limit of quantification.

All animals survived to their scheduled necropsy. There was no test article-related dermal irritation based on dermal evaluation of the dose site. There was no systemic toxicity based on clinical observations, cardiovascular (ECG) and ophthalmoscopic evaluations, body weight, food consumption, clinical pathology and post-mortem evaluations (organ weights, macroscopic and microscopic pathology). Thus, one embodiment of the invention is a non-irritating or reduced irritating pharmaceutical composition comprising 3,5-Dihydroxy-4-isopropyl-trans-stilbene or a pharmaceutically acceptable salt thereof, as compared to a formulation having a composition of 1 or 12 (with comparable % w/w active).

In conclusion, following twice daily topical administration of 3,5-Dihydroxy-4-isopropyl-trans-stilbene at doses of 0 (vehicle), 0.5, 1.0 and 3.0% w/w (animal study) in the present inventive formulations described in Example 7 (10, 20 mg/kg/day) and Example 8 (60 mg/kg/day, respectively) onto ~10% of total body surface area of minipigs (n=3/sex/group) for 28 days, resulted in no dermal irritation or systemic toxicity. Therefore the "No Observed Adverse Effect Level" (NOAEL) for dermal irritation or systemic toxicity was 3% (w/w) or 60 mg/kg/day, the highest dose tested. 3,5-Dihydroxy-4-isopropyl-trans-stilbene achieved a peak average concentration of 8265 ng/g in the skin (epidermis/upper dermis) in the 60 mg/kg/day group while systemic exposures were relatively much lower or often below the limit of quantitation in all treatment groups.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A chemically and physically stable topical pharmaceutical oil-in-water emulsion composition consisting of:
   an active ingredient 3,5-Dihydroxy-4-isopropyl-trans-stilbene or a pharmaceutically acceptable salt thereof in an amount of about 0.5% to about 2% by weight, based on the total weight of the composition,
   an oil phase in an amount of about 5% to about 25% by weight, based on the total weight of the composition, wherein the oil phase is selected from the group consisting of a fatty acid, an ester, an ester of glycerin, a fatty alcohol, a wax, a sterol, a siloxane, a silane, a hydrocarbon, an essential oil, a vegetable oil, a mineral oil, an animal oil, an edible oil and mixtures thereof,
   a water phase in an amount of about 30% to about 80% by weight, based on the total weight of the composition,
   a total surfactant content in an amount of greater than 5% to about 15% by weight, based on the total weight of the composition, wherein the total surfactant content consists of one or more non-ionic surfactants, and
a dermatologically acceptable excipient selected from the group consisting of an antioxidant, a pH adjusting agent, a preservative, a co-solvent, a chelating agent, a penetration enhancer, a humectant, a viscosity building agent, a fragrance, a colorant and combinations thereof;
wherein the oil phase contains <3% of petrolatum;
wherein the D90 of the average droplet size of the oil phase is from about 0.5 micron to about 1 micron;
wherein the topical pharmaceutical oil-in-water emulsion composition is chemically and physically stable when stored at standard ICH conditions for up to 6 months, achieves delivery to the skin and minimizes systemic exposure of the 3,5-Dihydroxy-4-isopropyl-trans-stilbene or a pharmaceutically acceptable salt thereof, and
wherein the topical pharmaceutical oil-in-water emulsion composition is formulated as a cream, an ointment, a foam, or a lotion.

2. The topical pharmaceutical oil-in-water emulsion composition according to claim 1, wherein when the oil phase contains either mineral oil or petrolatum, then a second oil phase component is present, or wherein when the oil phase contains both mineral oil and petrolatum, then a third oil phase component is present.

3. The topical pharmaceutical oil-in-water emulsion composition according to claim 1, wherein the oil phase contains ≤2% petrolatum.

4. The topical pharmaceutical oil-in-water emulsion composition according to claim 1, wherein the active ingredient is present in an amount from-about 0.1% to about 1% by weight, based on the total weight of the composition.

5. The topical pharmaceutical oil-in-water emulsion composition according to claim 1, wherein the antioxidant is present and is selected from the group consisting of propyl gallate, butylated hydroxytoluene, tocopherol, and combinations thereof.

6. The topical pharmaceutical oil-in-water emulsion composition according to claim 1, wherein the oil phase comprises at least one oil or fat, and wherein the at least one oil or fat is an ester or an ester of glycerin.

7. The topical pharmaceutical oil-in-water emulsion composition according to claim 6, wherein the ester of glycerin is a medium chain triglyceride of a carbon length from six to twelve carbons.

8. The topical pharmaceutical oil-in-water emulsion composition according to claim 1, wherein the one or more non-ionic surfactants is selected from the group consisting of ethoxylated fatty alcohol ethers, PEG castor oils, PEG esters, propylene glycol esters, glyceryl esters and derivatives, polymeric ethers, sorbitan derivatives, fatty alcohols, emulsifying waxes, and mixtures thereof.

9. The topical pharmaceutical oil-in-water emulsion composition according to claim 8, wherein the one or more non-ionic surfactants includes at least one ethoxylated fatty alcohol ether.

10. The topical pharmaceutical oil-in-water emulsion composition according to claim 9, wherein the ethoxylated fatty alcohol ether is a mixture of steareth-2 and steareth-20.

11. The topical pharmaceutical oil-in-water emulsion composition according to claim 8, wherein the one or more non-ionic surfactants is a mixture of an ethoxylated fatty alcohol ether and a sorbitan derivative.

12. The topical pharmaceutical oil-in-water emulsion composition according to claim 11, wherein the mixture of an ethoxylated fatty alcohol ether and a sorbitan derivative is a mixture of steareth-2, steareth-20, and polysorbate 80.

13. The topical pharmaceutical oil-in-water emulsion composition according to claim 8, wherein the one or more non-ionic surfactants is a mixture of an ethoxylated fatty alcohol ether, a sorbitan derivative, and a fatty alcohol.

14. The topical pharmaceutical oil-in-water emulsion composition according to claim 13, wherein the mixture of an ethoxylated fatty alcohol ether, a sorbitan derivative and a fatty alcohol is a mixture of steareth-2, steareth-20, polysorbate 80, and cetearyl alcohol.

15. The topical pharmaceutical oil-in-water emulsion composition according to claim 8, wherein the one or more non-ionic surfactants is a mixture of an ethoxylated fatty alcohol ether, a sorbitan derivative, and a non-ionic emulsifying wax.

16. The topical pharmaceutical oil-in-water emulsion composition according to claim 15, wherein the mixture of an ethoxylated fatty alcohol ether, a sorbitan derivative, and a non-ionic emulsifying wax is a mixture of steareth-2, steareth-20, polysorbate 80, and emulsifying wax NF.

17. The topical pharmaceutical oil-in-water emulsion composition according to claim 1, wherein the pH adjusting agent is present in an amount of from about 0.01% to about 10% by weight, based on the total weight of the composition.

18. The topical pharmaceutical oil-in-water emulsion composition according to claim 1, wherein D90 of the average droplet size of the oil phase is about 0.5 micron.

19. The topical pharmaceutical oil-in-water emulsion composition according to claim 1, wherein the composition is a cream.

20. The topical pharmaceutical oil-in-water emulsion composition according to claim 1, wherein the oil phase contains ≤1% of petrolatum.

21. The topical pharmaceutical oil-in-water emulsion composition according to claim 1, wherein the oil phase contains less than 1% of petrolatum.

22. The topical pharmaceutical oil-in-water emulsion composition according to claim 1, wherein the oil phase is free of petrolatum.

23. The topical pharmaceutical oil-in-water emulsion composition according to claim 1, wherein the composition has a uniform emulsion under microscopy.

24. The topical pharmaceutical oil-in-water emulsion composition according to claim 1, wherein the 3,5-dihydroxy-4-isopropyl-trans-stilbene or a pharmaceutically acceptable salt thereof is present in an amount of about 1% by weight of the composition.

25. The topical pharmaceutical oil-in-water emulsion composition according to claim 1, wherein the 3,5-dihydroxy-4-isopropyl-trans-stilbene or a pharmaceutically acceptable salt thereof is present in an amount of about 0.50% by weight of the composition.

26. The topical pharmaceutical oil-in-water emulsion composition according to claim 1, wherein the oil phase is selected from the group consisting of an ester, an ester of glycerin, an essential oil, a vegetable oil and mixtures thereof.

27. The topical pharmaceutical oil-in-water emulsion composition according to claim 1, wherein the oil phase is present in an amount of about 5% to about 15% by weight, based on the total weight of the composition.

28. The topical pharmaceutical oil-in-water emulsion composition according to claim 1, wherein the water phase is present in an amount of about 55% to about 75% by weight, based on the total weight of the composition.

29. The topical pharmaceutical oil-in-water emulsion composition according to claim 8, wherein the non-ionic surfactant is a mixture of cetearyl alcohol, polysorbate 60, steareth-2, steareth-20, and polysorbate 80.

30. The topical pharmaceutical oil-in-water emulsion composition of claim 1, wherein the pH adjusting agent is present and is a buffer.

31. The topical pharmaceutical oil-in-water emulsion composition of claim 30, wherein the buffer is selected from the group consisting of citrate/citric acid, acetate/acetic acid, phosphate/phosphoric acid, propionate/propionic acid, lactate/lactic acid, ammonium/ammonia, and edetate/edetic acid.

32. The topical pharmaceutical oil-in-water emulsion composition of claim 1, wherein the preservative is present in an amount of about 0.01% to about 2% by weight, based on the total weight of the composition.

33. The topical pharmaceutical oil-in-water emulsion composition of claim 1, wherein the preservative is present and is selected from the group consisting of benzyl alcohol, imidazolidinyl urea, diazolidinyl urea, dichlorobenzyl alcohol, chloroxylenol, methyl paraben, ethyl paraben, propyl paraben, butyl paraben, phenoxyethanol, sorbic acid, benzoic acid, salts thereof, and mixtures thereof.

34. The topical pharmaceutical oil-in-water emulsion composition of claim 1, wherein the co-solvent is present in an amount of about 1% to about 30% by weight, based on the total weight of the composition.

35. The topical pharmaceutical oil-in-water emulsion composition of claim 1, wherein the co-solvent is present in an amount of about 5% to about 20% by weight, based on the total weight of the composition.

36. The topical pharmaceutical oil-in-water emulsion composition of claim 1, wherein the co-solvent is present and is selected from the group consisting of propylene glycol, diethylene glycol monoethyl ether, and a combination thereof.

37. The topical pharmaceutical oil-in-water emulsion composition of claim 1, wherein the antioxidant is present in amount of about 0.001% to about 5% by weight, based on the total weight of the composition.

38. The topical pharmaceutical oil-in-water emulsion composition of claim 1, wherein the antioxidant is present and is selected from the group consisting of butylated hydroxytoluene, butylated hydroxyanisole, tocopherol, propyl gallate, tocopherol polyethylene glycol 1000 succinate, tert-butylhydroquinone, and mixtures thereof.

39. The topical pharmaceutical oil-in-water emulsion composition of claim 1, wherein the one or more non-ionic surfactants includes an emulsifying wax optionally in combination with one or more of ethoxylated fatty alcohol ethers, PEG castor oils, PEG esters, propylene glycol esters, glyceryl esters and derivatives, polymeric ethers, sorbitan derivatives, and fatty alcohols.

40. The topical pharmaceutical oil-in-water emulsion composition according to claim 2, wherein the oil phase contains either mineral oil or petrolatum and a second oil phase component is present, and the second oil phase component is selected from an ester and an ester of glycerin.

41. The topical pharmaceutical oil-in-water emulsion composition according to claim 2, wherein the oil phase contains mineral oil and petrolatum and a third oil phase component is present, and wherein the third oil phase component is selected from an ester and an ester of glycerin.

42. The topical pharmaceutical oil-in-water emulsion composition of claim 1, wherein the co-solvent is present and is selected from the group consisting of alcohols, carboxylic acids, diols, polyols, and esters.

43. The topical pharmaceutical oil-in-water emulsion composition of claim 1, wherein the co-solvent is present and is selected from the group consisting of ethanol, isopropanol, t-butyl alcohol, benzyl alcohol, hexyl alcohol, diethylene glycol monoethyl ether, butylene glycol, diethylene glycol, dipropylene glycol, ethylene glycol, hexylene glycol, pentylene glycol, propylene glycol, tetraethylene glycol, triethylene glycol, tripropylene glycol, polyethylene glycol, glycerol, caprylic/capric triglyceride, cetyl palmitate, coco-caprylate/caprate, cocoglycerides, dibutyl adipate, diisopropyl adipate, ethyl oleate, ethylhexyl cocoate, ethylhexyl hydroxystearate, ethylhexyl palmitate, isopropyl myristate, isopropyl palmitate, lauryl lactate, myristyl lactate, myristyl myristate, octyldodecyl stearoyl stearate, oleyl oleate, propylene glycol dicaprylate/dicaprate, propylene glycol isostearate, propylheptyl caprylate, and propylene carbonate.

44. The topical pharmaceutical oil-in-water emulsion composition according to claim 39, wherein at least about 90% of droplets of the oil phase have a droplet size of 0.5 micron to 0.75 micron.

45. The topical oil-in-water emulsion composition according to claim 1, wherein topical administration of said composition results in an AUC (from time 0 to end of the dosing interval) below 30 ng·h/mL.

46. The topical oil-in-water emulsion composition according to claim 1, wherein topical administration of said composition results in Cmax below 15 ng/ml.

* * * * *